(12) United States Patent
Romano et al.

(10) Patent No.: US 8,920,396 B2
(45) Date of Patent: *Dec. 30, 2014

(54) NUCHAIN NUPURPOSE CONTAINER CONDITIONING METHOD AND APPARATUS

(71) Applicant: Jack W. Romano/Medindica-Pak, Inc., Kirkland, WA (US)

(72) Inventors: Jack W. Romano, Kirkland, WA (US); Adam L. Smith, Palm Desert, CA (US)

(73) Assignee: Medindica-Pak, Inc., Kirkland, WA (US)

( * ) Notice: Subject to any disclaimer, the term of this patent is extended or adjusted under 35 U.S.C. 154(b) by 1 day.

This patent is subject to a terminal disclaimer.

(21) Appl. No.: 13/958,606

(22) Filed: Aug. 5, 2013

(65) Prior Publication Data

US 2014/0034190 A1    Feb. 6, 2014

Related U.S. Application Data

(63) Continuation of application No. 13/068,243, filed on May 6, 2011, now Pat. No. 8,540,689.

(60) Provisional application No. 61/395,689, filed on May 14, 2010.

(51) Int. Cl.
*A61M 1/00* (2006.01)
*A61J 1/20* (2006.01)
*B09B 3/00* (2006.01)

(52) U.S. Cl.
CPC ............... *A61J 1/20* (2013.01); *A61M 1/0001* (2013.01); *B09B 3/0075* (2013.01); *A61M 1/008* (2013.01)

USPC ........................ 604/319; 604/318; 604/540

(58) Field of Classification Search
USPC ................. 604/8–10, 39, 317–322, 404, 411, 604/540–544
See application file for complete search history.

(56) References Cited

U.S. PATENT DOCUMENTS

| | | |
|---|---|---|
| 3,032,037 A | 5/1962 | Huber |
| 3,661,143 A | 5/1972 | Henkin |
| 4,178,976 A | 12/1979 | Weiler |
| 4,388,922 A | 6/1983 | Telang |
| 4,397,643 A | 8/1983 | Rygiel |
| 4,620,846 A | 11/1986 | Goldberg et al. |
| 4,886,504 A | 12/1989 | Arvidson |
| 4,976,707 A | 12/1990 | Bodicky et al. |
| 5,269,924 A | 12/1993 | Rochat |
| 5,364,384 A | 11/1994 | Grabenkort |
| 5,382,244 A | 1/1995 | Telang |

(Continued)

OTHER PUBLICATIONS

U.S. Appl. No. 13/958,601, Romano et. al.

(Continued)

*Primary Examiner* — Philip R Wiest

(57) ABSTRACT

NuChain supply chain and disposal chain apparatus are created by NuPurposing containers, conditioning and transforming such containers from fluent material delivery containers into waste collection containers. Novel structural features of the waste collection systems allows bottle docking for the ingress of collection material into fluent material distribution containers as well as operation as a canister waste ingress collection system. The application of counter opposing forces on a canister and a lid operates in sealing and the unsealing and assembly and disassembly. A reduced pressure configured to be drawn away from said container inducing ingress of air into said container by a source of reduced pressure.

20 Claims, 39 Drawing Sheets

(56) References Cited

U.S. PATENT DOCUMENTS

| | | | |
|---|---|---|---|
| 5,514,123 | A | 5/1996 | Adolf |
| 5,586,973 | A | 12/1996 | Lemaire et al. |
| 6,318,417 | B1 | 11/2001 | Moore |
| 6,942,123 | B2 | 9/2005 | Wertenberger |
| 7,329,250 | B2 | 2/2008 | Romano et al. |
| 7,798,181 | B2 | 9/2010 | Romano |
| 7,854,729 | B2 | 12/2010 | Romano et al. |
| 8,118,795 | B2 | 2/2012 | Romano et al. |
| 8,137,329 | B2 | 3/2012 | Romano et al. |
| 8,353,885 | B2 | 1/2013 | Romano et al. |
| 8,540,689 | B2 * | 9/2013 | Romano et al. ............... 604/319 |
| 2002/0128584 | A1 | 9/2002 | Brown et al. |
| 2002/0128612 | A1 | 9/2002 | Andersson |
| 2004/0149348 | A1 | 8/2004 | Wertenberger |
| 2009/0057374 | A1 | 3/2009 | Leys |

OTHER PUBLICATIONS

U.S. Appl. No. 13/373,523, filed May 24, 2012, Romano et. al.

U.S. Appl. No. 13/373,454, filed May 24, 2012, Romano et. al.

U.S. Appl. No. 13/348,074, filed May 3, 2012, Romano et. al.

U.S. Appl. No. 13/345,631, filed May 3, 2012, Romano et. al.

U.S. Appl. No. 13/068,393, filed Nov. 17, 2011, Romano et. al.

U.S. Appl. No. 13/068,243, filed Nov. 17, 2011, Romano et. al.

U.S. Appl. No. 13/068,012, filed Nov. 17, 2011, Romano et. al.

U.S. Appl. No. 12/932,143, filed Jul. 28, 2011, Romano, Jack W.

U.S. Appl. No. 12/932,104, filed Jul. 14, 2011, Romano, Jack W.

U.S. Appl. No. 12/297,373, filed May 19, 2011, Romano et. al.

U.S. Appl. No. 12/927,049, filed May 19, 2011, Romano et. al.

U.S. Appl. No. 12/800,909, filed Dec. 30, 2012, Romano, Jack W.

* cited by examiner

CURRENT ENTERPRISE RESOURCE MANAGEMENT

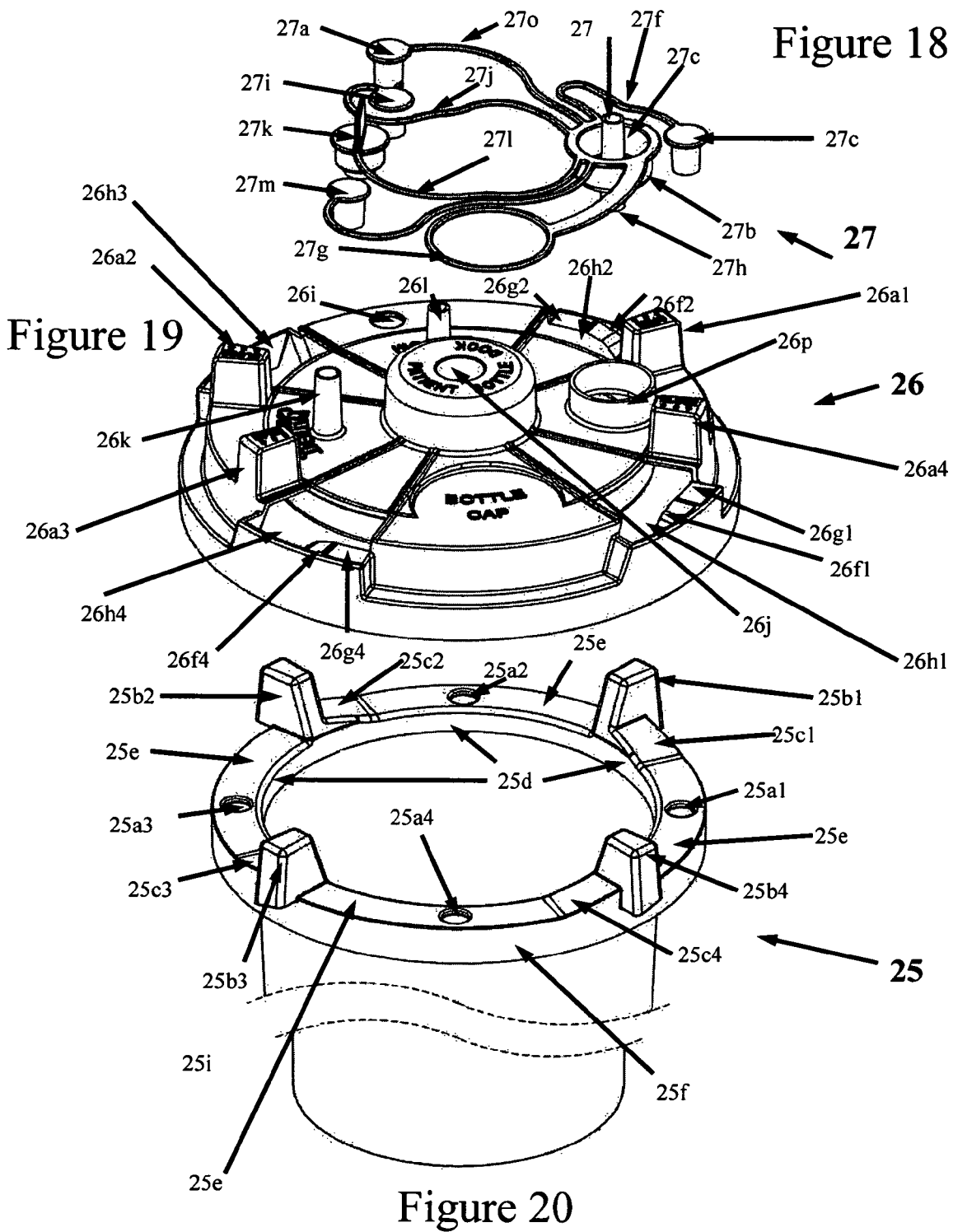

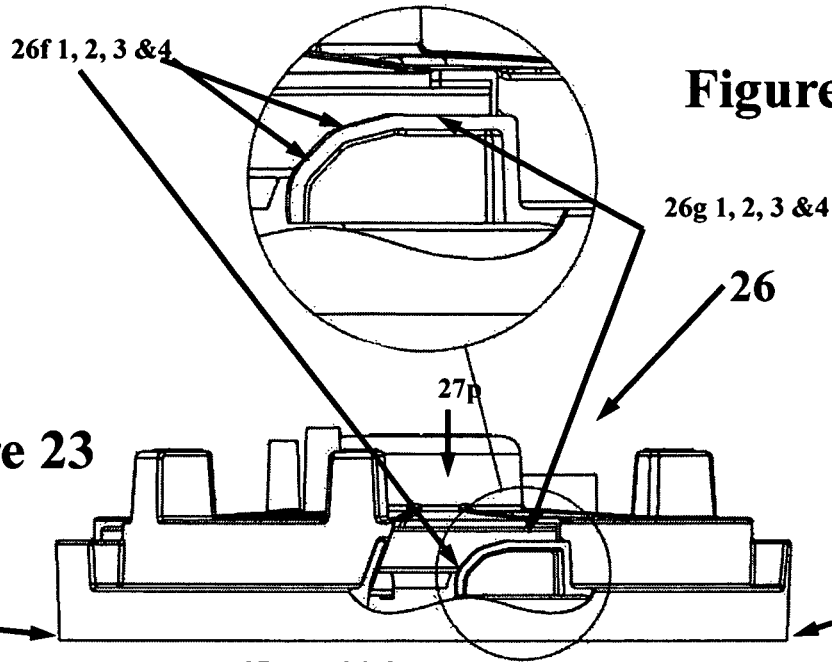
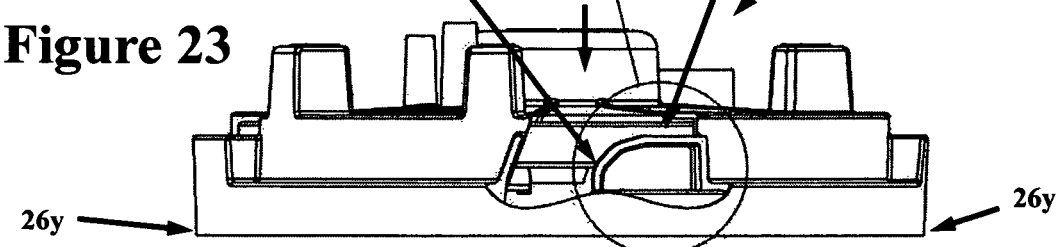
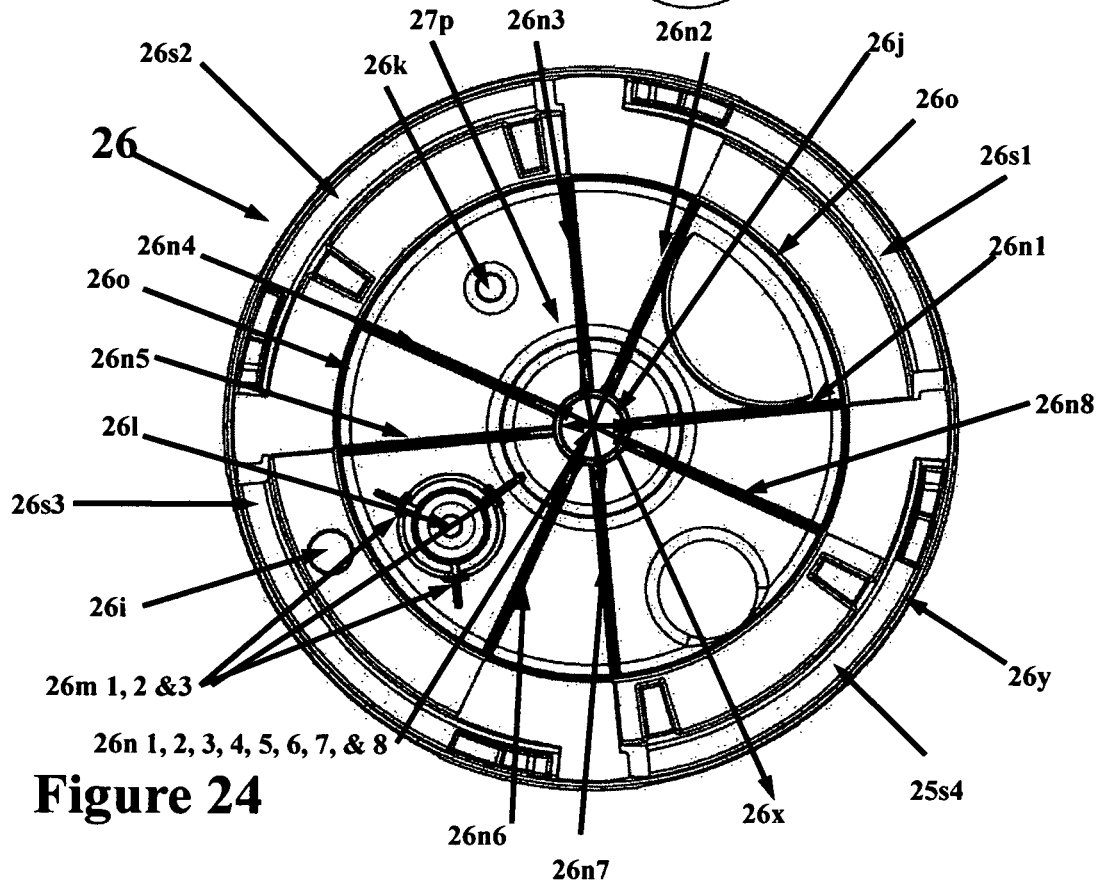
Figure 22
Figure 23
Figure 24

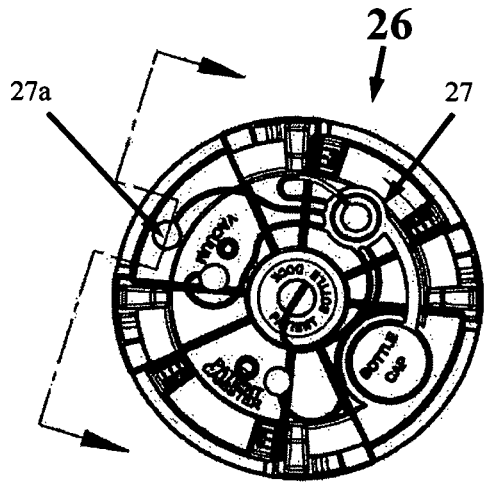
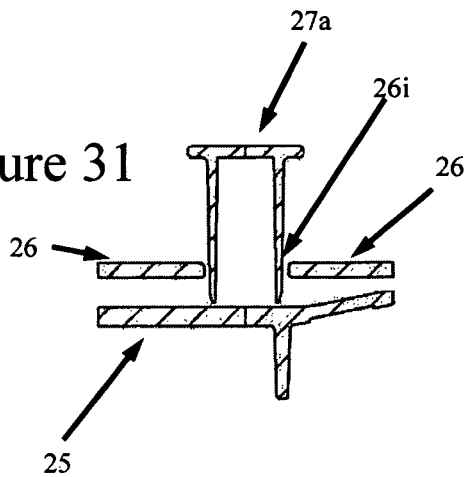
Figure 31
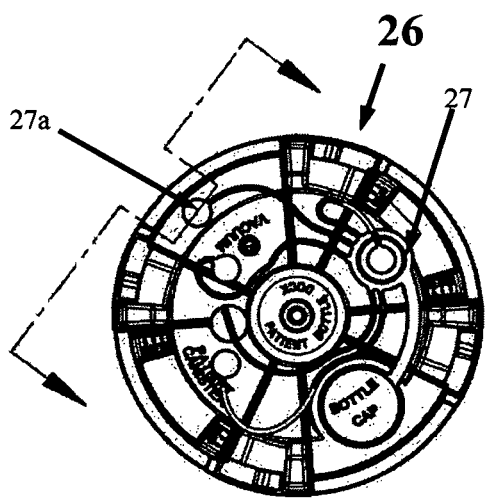
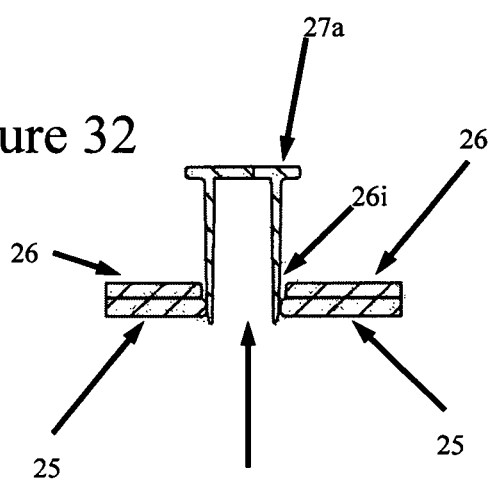
Figure 32
25a1, 2, 3, & 4
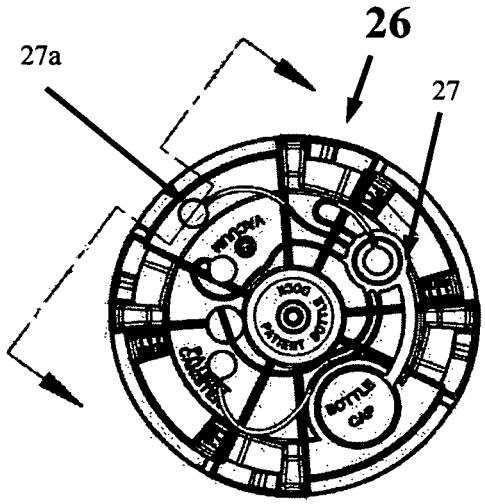
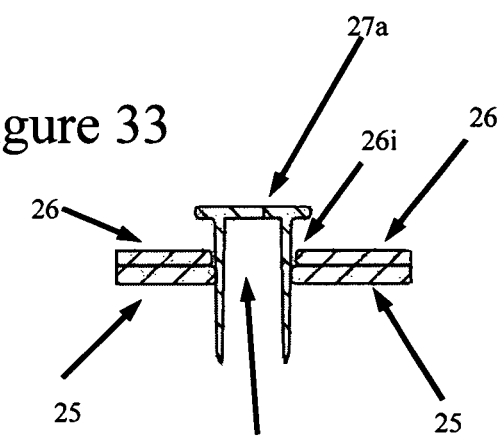
Figure 33
25a1, 2, 3, & 4

25 and 26 function

25 and 26 function

25 & 26 function

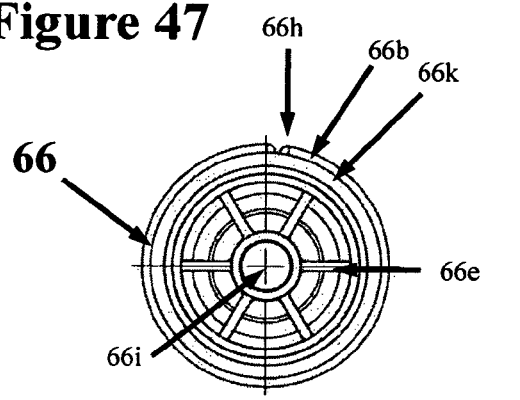
Figure 47
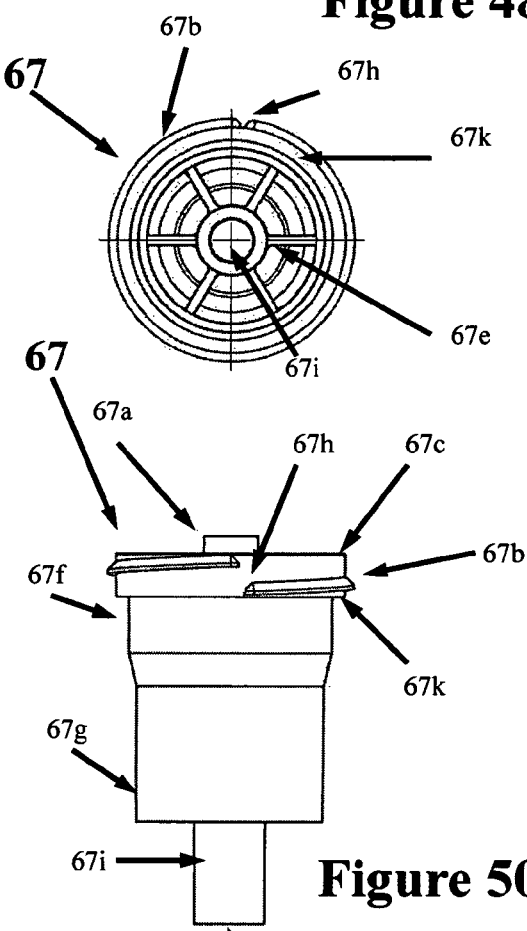
Figure 48
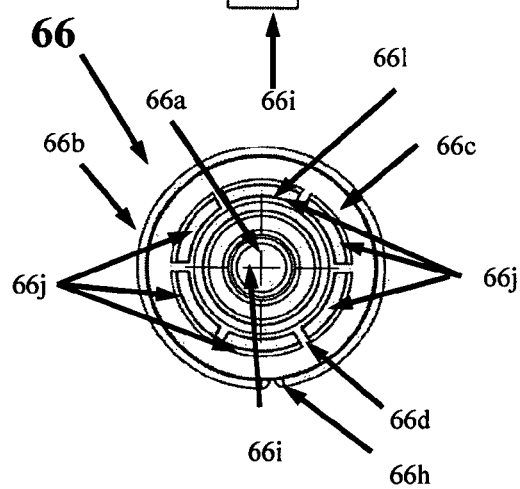
Figure 49
Figure 51
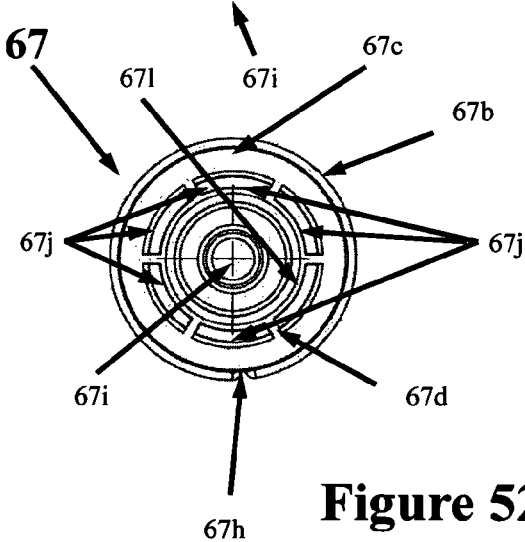
Figure 50
Figure 52

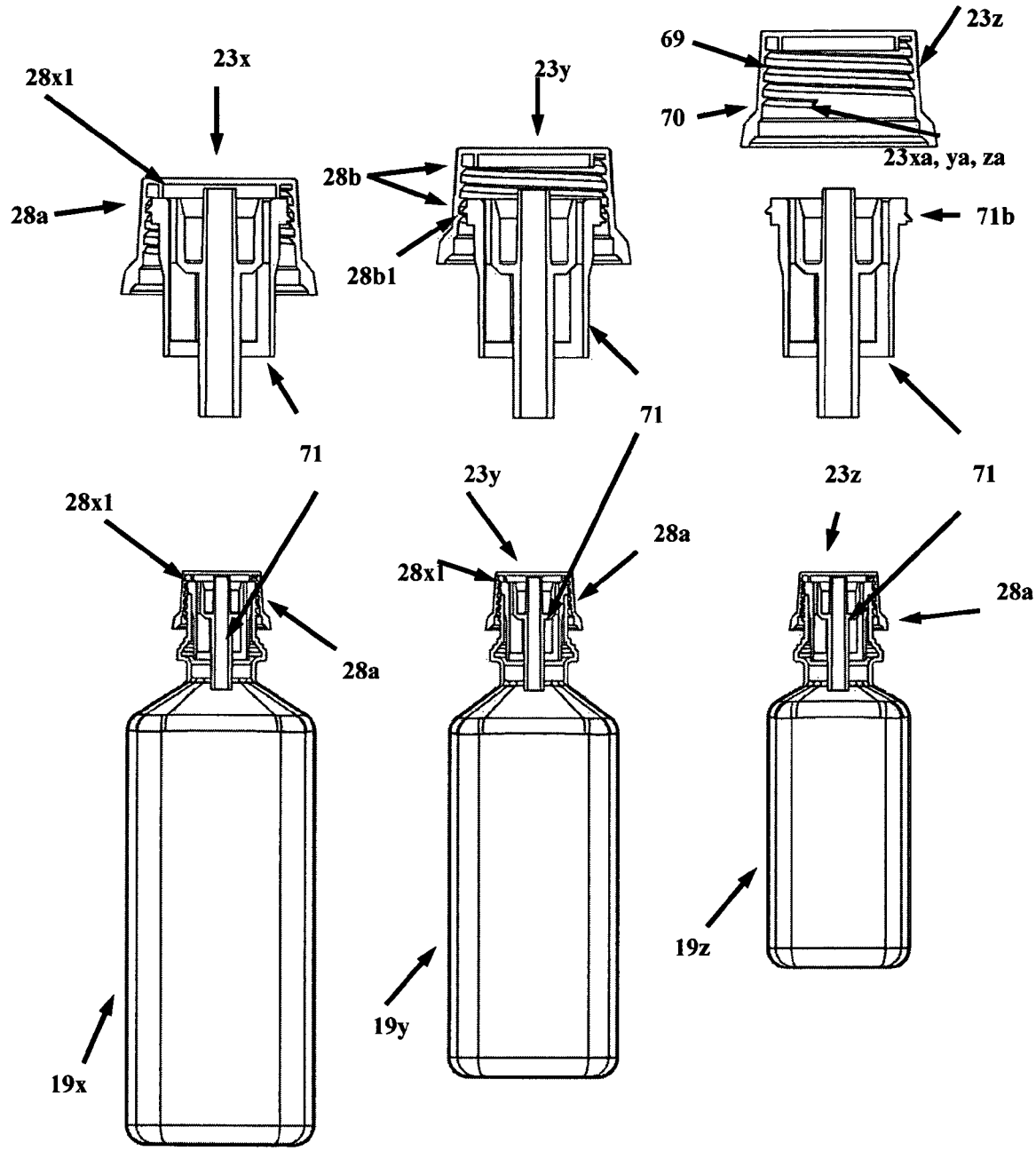
Figure 53 Figure 54 Figure 55

NUCHAIN NUPURPOSE CONTAINER CONDITIONING METHOD AND APPARATUS

CROSS REFERENCE TO RELATED APPLICATION

This non-provisional patent application claims the priority benefit under 35 USC 120 of U.S. patent application Ser. No. 13/068,243 filed on May 5, 2011, which claimed the priority benefit, under 35 USC 119(e) of U.S. Provisional Patent Application Ser. No. 61/395,689 filed on May 14, 2010.

INCORPORATION BY REFERENCE

This non-provisional patent application incorporates by reference herein U.S. Provisional Patent Application Ser. No. 61/395,689. This non-provisional patent application incorporates by reference herein U.S. Pat. No. 7,185,681.

FIELD OF THE SYSTEM

This invention relates to the field of reducing the waste stream burden in the medical field, but not limited to that.

BACKGROUND OF THE SYSTEM

In particular, this application relates to systems used in the collection and disposal of certain medical wastes. The collection of fluent waste material is a common procedure in the medical field. Most methods of surgical waste collection are carried out using vacuum suction. Some methods use gravity, while some use impelling devices which produce suction vacuum.

Examples of such impelling devices may comprise a meniscus shaver, a lipo-suction system, an arthroscopic fluid pump, a tissue ablator, an endoscopic irrigation and aspiration wand and the like. Surgical fluid waste is collected in containers commonly referred to as canisters and/or canister liners. These waste collection devices are generally disposable, some are re-cycled, re-processed, or rewashed. Some collection devices are re-used. Some are partially reused while some are intermittently re-used. Some are disposable or partially disposable. Some are used in conjunction with servicing units while some are used with additive agents for treating the waste material. Some are used multiple times on multiple patients without the preferable cleaning in between treatment of different patients. In certain instances reused devices are cleaned, reprocessed, sterilized, re-sterilized and or recycled and or prepared for reuse. There are disadvantages to the use of disposable collection canisters and canister liners. One problem is that disposable collection canisters and disposable collection liners contribute contaminated infectious plastic waste to the medical waste stream which is undesirable for the environment. Reuse of disposable collection devices by recleaning, re-labeling or reprocessing or recycling and or sterilizing, has the disadvantages of adding costly labor and requiring additional labor costs for sorting, containing transporting and handling of contaminated medical waste containers, and then the added costs of product re-entry into the internal/external product re-sterilization internal/external distribution system. There is a significant need to reduce medical waste. The need to reduce medical waste is a serious common goal of the United States and Internal Agencies. The Environmental Protection Agency (EPA) and the American Hospital Association has entered into a landmark Memorandum of Understanding (MOU) formally establishing the goals to reduce medical waste 50% by the year 2010. Hospitals for Healthy Environment (www.H2E-Online.org), now Practice Greenhealth and is the name of the aforementioned alliance for waste reduction, supported by formidable organizations and companies such as the American Nurses Association, Healthcare Without Harm, the EPA, plus Group Purchasing Organizations, leading health care organizations, federal, state and local government agencies and health care associations and the like.

It is important in the health care field to have good quality sturdy and reliable products. This is true especially in the field of collection of contaminated biological waste material. Containers for these purposes must be easy to use, and be designed with good human factors and ergonomics for the operators of such devices. One key important ergonomic feature is that the systems for collection of biological waste must be easy to use, and the amount of effort and strength required to assemble such systems should be easy and require little effort by the operators. Embodiments of the instant case provide for such ease of use. In addition other useful features which represent good quality standards for collection containers and systems and methods involve stability so that when containers are placed on a horizontal surface they are stable. The container should be puncture, leak and impact resistant and be stable and secure if dropped. It should be manufactured out of materials which function for the intended purposes, and if made form a polymer, have a durometer that should not crack or break if dropped. Labels and brackets should be made durable. The system should be autoclavable, so that if desired by the customer, it may be reused. The systems should be available in various sizes to accommodate a variety of patient populations as well as be effective to operate in a number of different treatment situations and locations. The system should not have any parts that are sharp, that might compromise the operator's personal protection, and not tear gloves, or other personal protective equipment such as gowns, gloves, masks, etc. Designs of systems of this sort should promote safe clinical care and perform according to those safe clinical standards. The design should promote resistance to opening after final sealing for disposal, as well as promote easy assembly and easy opening (in this case easy sealing and unsealing) with good ergonomic and human factor attributes. All closure seals should function tightly and maintain the leak proof seal during use, handling and transport. The design should accommodate easy carrying and handling so that transport of the systems may be done safely without contaminating the surrounding environment. Grips and handles should be designed for ease of access and use. Parts should be designed for ease of decontamination, and be rugged to withstand multiple autoclaving if desired. Openings must be free of obstruction, entanglement and sub-assembly parts must be able to attach and dis-attach without requiring undue hand work strength or significant effort.

In addition various scenarios that occur during health care are supply chain efficiency and supply management require unique features to products that encounter such scenarios. Some scenarios occur in the operating room. For example, collection systems should be designed to be easy to use during room turnover. They should be easy to use during intra-operative system changing. They should be easy to use after terminal sterilization and room setup. And they should be easy to use when preparing an operating room at the beginning of the operating day. Such collection systems should be easy to check/test to make sure they are operating correctly. Especially in a vacuum suction collection system, testing suction and checking seals must be easy and without undue fiddling or parts manipulation. This is especially significant whereas many time the individual who may be preparing the collection system for use, may do so prior to and at time different than actual use, which means the operator setting up the system for use is not the same operator using the system to collect waste. Ease of checking/testing, especially of the seals becomes important if, for example the prior individual does not properly assemble or prepare the system for subsequent use and the operator must then insure the system is in intended working condition at a later time. It is also desirable, when dealing with contaminated biological waste that handling of unsealed containers holding biological waste material is kept to a minimum, and that containers are sealed prior to handling and transport. It is also important that a minimum of handling be required during the various scenarios mentioned above and that hand and hand coordination may be achieved to carry out the aforementioned clinical safety features. It is understood that the aforesaid features for the aforesaid scenarios do not only apply to the operating room. Other settings as further defined by the instant application are all applicable. Another example is that safe sealing of containers containing biological waste must be achievable with one handed technique as provided by the instant system. These practical features bring good ergonomic and human factors to the instant system while providing a good clinically safe system into the health care setting.

DESCRIPTION OF THE PRIOR ART

Certain disadvantages of the prior art in these regards will become better understood with the explanations of the following references. U.S. Pat. No. 5,792,126 to Tribastone, et. al., discloses a collection canister system comprising canister interior of preferably 5000, 10000, and 15000 cubic centimeters and is taught to be effective for all procedures. A container of this size has disadvantages because it is too big for many collection applications. For example, suction collection for anesthesia where it is convenient to have a small collection canister attached to an anesthesia machine is preferable, especially in that most anesthesia suction volumes constitute just a few cubic centimeters of sputum or pharyngeal throat saliva most of the time. Larger equipment is also inconvenient in smaller rooms where suction collection equipment is found such as in the emergency room, the intensive care unit, the coronary care unit, patient hospital rooms, the neo-natal infant care units, physician offices, physician owned surgery suites, physician office surgery and procedure rooms, outpatient surgery centers, ambulatory surgery center, ambulances and other kinds of treatment rooms beside operating rooms, which require smaller apparatus for smaller more confined spaces. There are also concerns with cross contamination in any system where contaminated waste material remains in a room during the presence of subsequent multiple patients. Another disadvantage of the larger 5000, 10000, 15000 cc containers is weight and mobility. Such weight in the extremely large heavy volumes are sometimes embody difficult ergonomics imposing risk of injury to personnel such as back pain, and other injuries whereby by seams in floors and door jams which are not smooth may induce tipping over and spillage of large volumes of medical waste. Another disadvantage of such large heavy containers is its size. Such large containers are more difficult to keep clean and cumbersome to handle, and because of the awkward size, and could cause ergonomic strain as related to the U.S. Pat. No. 5,792,126 reference. U.S. Pat. No. 5,960,837 to Cude et. al., discloses a suction canister and lid combination whereby only a destructive force will only separate the parts which renders the Cude invention to be an only disposable product which is costly whereby each time a canister is used another is purchase to replace it. A purchase is made and is costly to the customer and each plastic disposable product enters the disposal chain waste stream and another piece of garbage enters the land fills or incinerators which are disadvantages. This is expensive, and requires 'ongoing inventory space and inventory handling. Another disadvantage is a lack of choice for the customer to re-process, re-sterilize or re-use which options are beneficial but not available with the U.S. Pat. No. 5,960,837 reference. U.S. Pat. No. 5,901,717 to Dunn et. Al., discloses a canister and flushing system. This system comprises a complex system for handling a collection canister. The disadvantages of this system are expensive equipment is required and it is complex equipment. These expenses and maintenance plus require periodic inspection by biomedical engineering which increases labor costs associated with its presence. In addition the equipment must be kept clean which is an additional requirement for daily operations. An other disadvantage is that a reusable canister which requires costly labor for internal processing, reprocessing, resterilization and reusing. In most institutions, volume of such collection systems is quite high imposing internal/external processing costs. The system discloses the disposable flush kit which maintains higher disposable costs along with the higher costs associated with internal distribution, inventory handling and higher disposable waste removal costs. U.S. Pat. No. 4,419,093 to Deaton discloses a reusable canister having a disposable lid and liner. This system is delivered in pieces and requires subassembly by the customer prior to operation. This requires additional labor which is costly and involves the inventory tracking of a plurality of pieces to a system in sets and often times lids and liners can become separated and when out of numeral matching balance one cannot be use with out the other, whereas resulting in an incomplete set and a unusable subassembly. This disadvantage complicates the ongoing internal/external distribution and tracking of pieces which adds costly labor, inventory management and excess handling. The U.S. Pat. No. 4,419,093 reference also discloses contribution of garbage to the waste stream which is a serious environmental concern. Other disadvantages of disposable collection containers and canister liners include the difficulty in which to assemble a lid to a container body. Many disposable canister systems have a container body which is stackable. This stack ability allows the container bodies to be nested on each other with one container resting substantially within the other with the exception of about one to two inches of body length. This stack ability feature is desirable whereas the volume of containers handling in the disposable application is very high. For example a busy institution may process anywhere between 10,000 or less and 50,000 or more disposable canisters and/or disposable canister liners per year. The stack ability feature makes these canisters easier to transport in volume. One problem with the assembly of such stackable canister and it's associated lid, is that the snap on feature of the lid must be very tight in order to be fluid leak proof in the event of tip over. In order for these canister lid interfaces to be leak proof they must fit very tightly making for a very difficult assembly. The force required to assemble the canisters and lids of this nature is greater than a force which would normally be deemed easy to use. In fact they are very difficult to use. Good ergonomic systems include assembly and dis-assembly features that do not require undue finger, hand and/or upper body strength. Many of the prior art collection systems have snap together assembly features that, due to their seal design, require more force to assemble, than most operators can easily of effortlessly provide. This is because of the force required to snap together lids and canisters that are not manufactured or easy to dis-assemble, must remain tight enough to stay sealed during transport, handling and tipping over in order to meet product safety requirements. The applicant believes that if a system cannot be assembled with much less force than an easy amount upper body strength of the average operator, then there are human factors and ergonomics design issues related to such canister and lid assemblies that need to be resolved. The Applicant believes that the snap fit force utilized to keep a lid and canister housing together during transport and tipping is not the same force that provides for good human factor/ergonomic and good clinical handling. Applicant contents that when snap fit forces are greater than the average upper body strength of the average operator, then clinical safety is in jeopardy and personal protective equipment such as protective gloves are at risk for tearing or hole.

DESCRIPTION OF THE SYSTEM

The instant embodiments provides methods and systems for establishing and managing NuChain ERP Systems by NuPurposing products and containers into uses and applications that provide additional value, rather than just throwing spent containers into the garbage. The embodiments of the instant case solve problems by NuPurposing containers. For example, when pour bottles are NuPurposed, it becomes a cost competitive practice. Also, without the embodiments teachings of the instant case, easy human factors and ergonomics involving exchanging filled NuPurposed containers is less smooth. Switching out bottles with respect to a permanent canister system requires a minimum amount of complexity of hand movement and hand strength. The instant case solves a problem of degree of ergonomic hand strength. The instant case solves a problem of human factors and ergonomics. The instant case solves the problem of cost competitively manufacturing a lid, canister and capping member designs that only require single pull tooling which will operate not only as a canister, but as a bottle docking system.

The instant case solves a problem by using single pull tooling that can manufacture systems out of cost effective materials so the system functions as a disposable. The instant case solves the problem of cost competitive manufacturing by a lid, canister, and capping member design that only requires a single pull tooling for manufacturing permanent systems out of more durable and heat resistant materials for permanent autoclavable systems. The Instant case also solves the problem of what to do in a scenario whereby there are no bottles for bottle docking therefore leaving a consumer without the bottles to NuPurpose. The instant case also solves a problem by teaching a functional ergonomic system having a low parts count requiring only a few number of single pull injection molding tools for both bottle docking and for non-bottle docking collection systems being the same tools that produce both. The instant case embodiments comprise utilizing fluid enclosing product transfer delivery containers which do not embody the self inherent physical construct capacity to maintain shape under extreme negative vacuum pressures up potentially minus 1 atmosphere. Examples of cost effectively fabricated fluid enclosing containers made for delivery of fluids which may not embody inherent implosion resistant structural strength and rigidity needed for suction vacuum collection, may include plastic delivery containers such as plastic pour bottles and intravenous containers. The present system discloses cost effective practical solutions for reducing waste, reducing labor, reducing inventory, reducing receiving, reducing internal distribution, and reducing inventory handling costs and space required to carry inventory all involved with the collection waste materials. These achievements are carried out by the instant embodiment. Successful suction vacuum collection may be realized using, in a flexible manner, cost effectively fabricated fluid enclosing distribution, commercialization, and transfer delivery and fluid administration containers. This patent application discloses collection systems that teach a use of fluid enclosing product supply containers for collection, removal and disposal of waste material into the disposal chain. In particular, delivery containers for general distribution, transfer and administration of pour bottle solutions and intravenous solutions, parenteral and enteral solutions and the like are converted into the waste collection and disposal chain containers. This application also teaches use of a common fluid enclosing container for both the supply and the disposal chain. The instant application also teaches use of containers found in inventory for supply and delivery of fluids and then transforming them for the collection removal, and disposal utility found in the disposal chain. This application teaches the use of a common fluid enclosing container for the product transfer and then integrates the container into systems for the collection and the removal of waste material. The instant application teaches waste reduction methods by integrating delivery container fabrication and the collecting and disposing of waste materials. Potential container fabrication processes applicable to the applicable to the instant case comprise blow fill seal manufacturing, blow molding or continuous blow molding. Another type of container fabrication process applicable to the instant application is a blow fill seal fabrication whereby a container is formed, filled with fluid and hermetically closed within one machine. The instant application teaches the waste reduction methods by using manufacturing methods as mentioned such as blow molding, blow fill sealing, laminating sheets such as in intravenous solution container manufacturing methods to form enclosures. One purpose of the instant case is to transform these containers which are derived from a fluid delivery mode, from product transfer and administration, and then, converting the container to collection removal and disposal of waste materials.

The embodiments of the instant case provides container utility options for the transfer and administration of products, consumption of products and for the waste collection removal and disposal options. The embodiments of this instant case discloses the utilization of fluid filled product transfer containers such as pour bottles and/or intravenous solution containers (IV bags) (and/or other product/fluid containing enclosures used for intravenous therapeutics and the administration of anesthetic agents as well as other medicaments) for the receiving, collecting, containment and disposal of waste. Using fluid enclosing product distribution transfer/administration containers also for the handling of waste results in optimal reduction of waste, reduction of inventory, reduction in labor, reduction of internal/external inventory distribution/processing/re-processing/re-using/re-cycling, reduction of inventory handling and waste disposal costs (brought by the unnecessary the need for separate supply and disposal containers in certain circumstances), all are reduced by eliminating the supply chain costs with the fabrication of the said separate supply and disposal/collection containers. The question arises why pay for the manufacturing and distribution of unnecessary empty disposable containers, if a fluid delivery container can be derived from the supply side and then be converted into a collection and removal/disposal container for the collection and disposal of waste materials. Such container are supplied clean/sterile and are made to meet certain sterility assurance levels (SAL). The instant embodiments confer options allowing consumer choices for the reduction of waste. Plastic transfer containers such as blow molded containers, continuous blow molded containers, blow fill seal containers, intravenous solution containers, containers made of laminated sheets of polymers and of foils, are commonly used for the distribution transfer and administration of fluid products and other product such as sterile water, sterile saline solution intravenous solutions for IV therapeutics, IV solutions for administration of anesthetic agents and other water for injection (WFI) based fluid formularies as used in the medical field. Also available for other purposes are cleaning solvents, prep solutions, alcohol solutions, other product materials and the like. Solutions are used for intravenous therapeutics, parenteral administration, and administration of anesthesia, wound irrigation, irrigation for arthroscopic, endoscopic, laparoscopic procedures, irrigation for urology procedures and many other types of applications. The instant application names additional fluid materials delivered in polypropylene, and high density/low density polyethylene and polyvinyl chloride containers which are all generally high volume manufactured supplies. Such supplies are engaged with the supply chain on a just in time basis or on a vender inventory managed basis or a customer managed basis from procurement to payment. Intravenous solution containers are also used for the distribution/commercialization of these contained materials and products. It is understood the disclosed teaching of the instant case are not limited to sterile liquid distribution/supply containers or the transfer of fluid filled product containers. Other product transfer containers may be suitably integrated with innovation of the instant case, to function, in addition to providing materials, but also with a delivery and waste disposal capacity. Other container such as prep solution containers, alcohol containers, solvent containers, cleaning solution containers and the like may function suitably within the scope of the present system. These teachings are not intended to limit the attached claims. Other product containers may also be used in the instant systems. These product delivery containers are commercialized/distributed to the customer having volume cubic capacity for transferring of waste materials. The instant embodiments reduce the amount of plastic introduced to the waste stream. The instant embodiments reduce the recycling, reprocessing and labor associated with the handling and re-use procedures thereby lowering the associated costs of waste removal. The instant embodiments reduce the supply chain costs from manufacturing to disposal. Collecting fluent waste material in fluid enclosing delivery containers such as open top blow molded, or continuous blow molded containers, intravenous solution containers, irrigation solution containers, closed top blow fill seal containers or form fill seal containers, which have been cost effectively fabricated with thin walls which do not have the strength or construction to resist high vacuum implosion forces, provide various solutions and options for solving the disadvantages and problems of prior art containers. When the methods and systems embodied in the teachings of the instant application are utilized, the instant embodiments at times also provides for reducing the handing, reducing the labor and reducing the costly process of recycling, re-using re-processing sterilizing and or re-sterilizing. Certain product delivery transfer containers are fabricated commercialized and are already present or already in the supply, distribution, inventory and administration chain and/or in the customer facility. Present system conveniently transforms converts and integrates these fluid enclosing transfer delivery containers for their transformation to waste materials collection containers establishing a new type of environmental supply chain. We refer in part to this new novel environmental process as a disposal chain supply system by the deployment of supply chain supplies to collect, remove and dispose of waste material. This defines new supply and disposal chain systems, methods and systems for using fluid enclosing distribution containers, and bottle docking methods, and bottle docking systems, and bottle docking processes methods for processing containers from the clean delivery side of fluid administration/consumption, and transformation and conversion and conditioning of such containers fort the dirty material collection removal and disposal side, integrating the disposal chain and the supply chain with a common container as taught by the instant case, for environmental purposes herein referred to as disposal chain supply systems. Disposal chain supply systems define a novel environmental process. Disposal chain supply systems are defined by transforming distributing containers into collection removal and disposal containers. A disposal and supply container conversion provides an environmentally preferred container transformation method and system. A disposal chain/supply chain container utilizing disposal chain supply chain systems confers options and advantages and is disclosed by the instant case. Disposal supplies are environmentally preferred if transformed as taught by the instant case embodiments. Disposal supplying as taught by the instant case is the environmentally preferred system and method of container conversion.

Difficulties exist with the use of certain containers when integrated into high negative pressure vacuum/suction system. Negative vacuum draw pressures potentially of one atmosphere of negative pressure is common for drawing surgical waste materials from a surgical site into a collection receptacle. One problem is that the common blow molded or blow fill sealed containers are cost effectively manufactured with relatively thin plastic wall formations sometimes having a wall thickness range varying at about 0.025 inches or less and are generally made with a plastic materials such as high density polyethylene, polypropylene, polyvinyl chloride, or other like materials. Thin walled containers are commonly fabricated to reduce the plastic material mass (volume of plastic materials per unit) and hold down production manufacturing material costs and shipping weight. It is common practice of container manufacturing to consume the minimum amount of material used per unit to fabricate each container yet maintain user function for cost effective manufacturing purposes. Common container material durometer comprising containers having such ranges of this wall thickness in these like materials are not generally strong enough to withstand the negative differential pressures of potentially minus one atmosphere of negative pressure as commonly found in a vacuum/suction system, without imploding or deforming. Product fluid enclosing distribution transfer containers are commonly fabricated using processes know by artisans skilled in the arts of blow molding or continuous blow molding of open top containers and/or blow fill sealing of closed top containers, as well as using such manufacturing processes such as thermal lamination of plastic sheets to form cavities/enclosures for the filling and production of intravenous solution containers and other parenteral solution containers and the like.

One solution to the problem of implosion and/or bottle/container deformity which occurs under high vacuum pressure is to integrate a container with a suction collection system whereby container wall is interposed between its inner chamber and an outer space with each space subjected to a negative draw vacuum force/pressure. Such force and pressure is applied on the outside of and on the inside of the container which forms opposing differential pressures with provides reinforcing balances by effecting a similar positive and negative neutralizing net force at the same time on the container wall reducing negative implosion forces on the container wall. This is carried out by the container and canister of the instant case co-acting to contain waste and balance negative draw forces along the composite draw path. This addresses one issue of container deformity. This instant application discloses the neck of the pour bottle as the utilitarian area of the bottle for coupling with a lid of a canister system. The instant application discloses a throat aperture space (pour spout) of a plastic pour bottle as a utilitarian area for egress and ingress of draw forces from and toward a supply container. The instant application discloses the throat space aperture, pour spout as a utilitarian area for coupling of a throat aperture plug. The instant application discloses force egress and force ingress exchanges at a plug for providing force communication between the inside and outside of a container utilized for the administration of a material. The instant application discloses locating an atmospheric air pressure draw exchange at the neck of the container. The present application discloses interposing the container neck (pour spout) annularly between a plug and a lid to seal contain and direct air forces such that said air forces may be egressed from said container, and to contain such drawn air forces such that said air forces may be ingressed into said container. The present system discloses configuring the plastic container throat space in a negative air pressure draw vacuum system whereby a container in draw air force is configured to transfer and deposit medical waste material into the container and an outdraw force is disposed to transfer the differential draw forces. The embodiments of the instant case utilizes the inner chamber of a plastic pour bottle as part of the reduced air pressure vacuum draw path. The present case discloses several embodiments for carrying out the system.

PURPOSE AND METHODS OF THE SYSTEM

One object of the system of realizing a NuChain supply chain and disposal chain system by NuPurposing is to position a liquid transfer fluid enclosing container upstream to a patient delivery sequence, and then placing the container downstream in connection with the flow of a waste material. Another object of the system of creating a NuChain supply chain and disposal chain system by NuPurposing is to convert a liquid container affecting egress of the liquid and then the positioning of the container in flow confining connection downstream to a source of waste material. Another object of the system of creating a NuChain supply chain and disposal chain system by NuPurposing is to egress a solution from a container and then place the container downstream along a vacuum draw path in flow control connection with a suction wand. Another object of the system creating a NuChain supply chain and disposal chain system by NuPurposing is to orient a liquid transfer container upstream to and in vascular access connection with a patient and then position the transfer container downstream in flow control composite connection as a portion of a vacuum draw path.

Another object of the system creating a NuChain supply chain and disposal chain system by NuPurposing is to provide supply chain efficiency whereby the dispensing container is also the receiving receptacle/container. Another object of the system is creating a NuChain supply chain and disposal chain system by NuPurposing is to provide waste reducing processes whereby egress of a fluid from a container upstream from a healthcare patient is subsequently a same or similar container positioned downstream in flow control association with a negative atmospheric pressure draw force, drawing forced air away from said container while in flow confining connection with a suction wand. Another object of the system creating a NuChain supply chain and disposal chain system by NuPurposing is to provide practical steps for internal container handling including a) fabricating a transfer container, b) taking a transfer container and extending a draw path between a vacuum source and a suction wand, c) connecting a fluid enclosing delivery container to the path, d) depositing the waste material into the container. Another object of the system is to provide methods and systems including a) enclosing a fluid in a container at manufacturing and transferring said container and said fluid through distribution and administration for health care consumption, b) consuming at least a portion of the fluid, c) converting the container into a vacuum collection system, d) removing the waste in the container e) disposing the waste. Another object of the system creating a NuChain supply chain and disposal chain system by NuPurposing includes a supply and disposal method comprising a) manufacturing a fluid enclosing container for the distribution, transfer and administration of a fluid product, b) consuming at least a portion of the liquid, c) directing a draw force to and from the container along an intermediate portion of a composite draw path, d) depositing waste material into the container.

Another object of the system establishing a NuChain supply chain and disposal chain system by NuPurposing is to provide a method for reducing supplies comprising, a) providing a container fabricated for the delivery of a product, b) delivering the product, c) connecting the container to a vacuum source system, d) drawing waste material into the container, e) removing the waste material in the container, f) disposing of the waste material. Another object of the system is to provide a method for reducing waste comprising a) transforming a waste receptacle from a container manufactured for enclosing and delivering a fluid, b) connecting the container to a composite waste draw conduit, c) depositing the waste material in the container, d) removing the container from the draw path, e) converting another delivery container into a waste receptacle comprising transformation of a fluid enclosing supply container into a waste collection receptacle. Another object of the system includes providing the methods and a system for the transforming a plurality of supply containers into a plurality of waste containers. Another object of the system includes establishing a NuChain supply chain and disposal chain system by NuPurposing is to enclose a plurality of supply containers having been transferred into a plurality of collection containers within a single enclosure (not shown). Another object of the system establishing a NuChain supply chain and disposal chain system by NuPurposing is to provide methods for transforming supplies into waste receptacles comprising a) constructing a fluid enclosing container, b) taking the container c) extending a draw path between a vacuum source and a suction wand d) connecting a delivery container to the path, e) depositing waste material into the container. Another object of the system creating a NuChain supply chain and disposal chain system by NuPurposing is to provide methods for deriving waste receptacles from supply containers including a) providing a liquid product in a selectively connectable waste receptacle b) disposing the receptacle in a vacuum collection container system, c) drawing a force along a composite draw path between a source of waste material and a vacuum source d) depositing waste in the delivery receptacle. An object of the instant case comprises positing a transfer container upstream in the flow of patient care sequences for liquid dispensing and administration, b) positioning the container downstream in the flow of patient care in a material receiving and receptacle mode. Another object of the embodiments herein creating a NuChain supply chain and disposal chain system by NuPurposing is disclosed whereby the receptacle is positioned on the clean side of the supply and disposal chain for dispensing of it contents and the dispenser is positioned on the dirty side of the supply and disposal chain for receiving waste material as a receptacle, and the receptacle is in receiving structuration with a gravity flow system and or a composite vacuum draw path. Another object of the system creating a NuChain supply chain and disposal chain system by NuPurposing is to provide methods and systems for drawing a negative pressure within a fluid transfer and dispensing container. Another object of the system creating a NuChain supply chain and disposal chain system by NuPurposing is to provide methods for placing the container downstream to a flow control conduit depositing waste into the container under a positive push force, not a negative vacuum force. Another object of the system creating a NuChain supply chain and disposal chain system by NuPurposing is to provide methods and systems in structuration with a draw force including a) enclosing a fluid in a container at fabrication and providing the liquid product in a selectively connectable receptacle, b) disposing the receptacle in a vacuum collection canister system, drawing a force along a composite path along a source of waste, depositing the waste into a delivery receptacle. Another object of the embodiments herein creating a NuChain supply chain and disposal chain system by NuPurposing as disclosed is to provide connect ability to a transfer container and a vacuum canister collection lid. Another object of the system creating a NuChain supply chain and disposal chain system by NuPurposing is to provide a composite negative atmosphere draw path formed at least in part by the interior of a transfer container. Another object of the system creating a NuChain supply chain and disposal chain system by NuPurposing is to provide a draw force directed by a composite draw path in part co-acting to transform a delivery container to dispose waste material. Another object of the system creating a NuChain supply chain and disposal chain system by NuPurposing is to provide a canister in structuration with a fluid enclosing supply transfer container forming at least a portion of a composite draw path interposed between a vacuum source and a site of material waste.

Another object of the system is to combine in association with the novel features cited above, a negative draw path with a material flow path. Another object of the system creating a NuChain supply chain and disposal chain system by NuPurposing is to combine a draw path with the material draw path to dispose material in a transfer container to remove waste material from a site. Another object of the system creating a NuChain supply chain and disposal chain system by NuPurposing is to provide a throat aperture space/plug and seal disposed in a transfer container access/port site forming at least a part of the draw path controlling draw forces to and from a transfer container. Another object of the system creating a NuChain supply chain and disposal chain system by NuPurposing is to provide a receptacle derived from a health care delivery sequence which is converted to co-act with a canister, a lid, a draw force, a composite path, a throat plug to dispose waste. Another aspect of the system creating a NuChain supply chain and disposal chain system by NuPurposing is to provide supply chain efficiency methods comprising a) fabricating liquid enclosing delivery container, b) transferring the liquid to a delivery site, c) administering the liquid and connecting the container in structuration with a waste collection system, d) collecting the waste. Another aspect of the system creating a NuChain supply chain and disposal chain system by NuPurposing is to provide supply chain efficiency methods comprising a) manufacturing a fluid enclosing container for the distribution of a liquid product b) distributing a liquid product, c) consuming at least a portion of the product d) directing a negative suction vacuum draw force to the container, e) connecting the container to a composite draw path having a suction wand at one end thereof, e) placing the suction wand in suctioning wand in relation with waste material and drawing the waste material into the container, f) removing the material in the container, g) disposing the material. Another object of the system creating a NuChain supply chain and disposal chain system by NuPurposing is to a) fabricate a fluid enclosing delivery container for disposal and collection in a waste collection system. Another object of the system creating a NuChain supply chain and disposal chain system by NuPurposing is to provide a method of reducing waste collection comprising a) enclosing a fluid product in a fabricated delivery container, b) egressing the fluid from the container, and connecting the container along a vacuum draw path, drawing waste material into the container, c) removing the material for disposal, disposing the material. Another object of the system creating a NuChain supply chain and disposal chain system by NuPurposing is to provide a method of collecting supplies and transforming them into waste receptacles comprising a) collecting delivery supply containers, b) placing the containers positioned to receive waste in vacuum canisters, c) drawing vacuum, d) controlling the draw force to direct waste material for disposing waste in the transfer container. Another object of the system creating a NuChain supply chain and disposal chain system by NuPurposing is to provide a method of a) converting containers having dispensed at least some container contents, b) converting the container into a vacuum collection system receptive to waste collection and or removal and or disposal. Another object of the aforementioned objects is to provide a method of handling a dispenser and a receptacle wherein the dispenser is the receptacle. Another object of the system creating a NuChain supply chain and disposal chain system by NuPurposing is to provide a delivery collection container system using fluid enclosing bottle fabricated from a blow molding, and or a continuous blow molding process out of previously shaped polymer performs. Another object of the system creating a NuChain supply chain and disposal chain system by NuPurposing is to provide a delivery and collection container fabricated from a fluid enclosing blow fill seal manufacturing process container. Another object of the system creating a NuChain supply chain and disposal chain system by NuPurposing is to provide a suction/vacuum system which renders product distribution/transfer containers receptive to waste materials. Another object of the system creating a NuChain supply chain and disposal chain system by NuPurposing is to provide a collection system for reducing waste that is derived from product delivery. Another object of the system creating a NuChain supply chain and disposal chain system by NuPurposing is to reduce internal/external distribution, internal/external inventory management whether management is carried out by a vender management program or by a customer. Another object of the system creating a NuChain supply chain and disposal chain system by NuPurposing is for the consumer to account for the cubic volumes of incoming fluids and cubic volumes of outgoing waste materials for analysis and matching incoming fluids and container volumes and outgoing waste materials so the number of containers needed to optimize the supply purchasing process may be identified within the scope of the instant case. Another object of the system creating a NuChain supply chain and disposal chain system by NuPurposing is to provide methods and systems for sealing a vacuum draw path and for unsealing a vacuum draw path so that pour bottles, intravenous solution containers, and other types of containers may function to improve supply chain metrics relating to reducing inventory, labor, costs, shipping, and for reducing the overall mass of materials contributed to the waste stream. Another object of the system creating a NuChain supply chain and disposal chain system by NuPurposing is to provide convenient methods and systems for connecting and disconnecting a composite draw path utilizing in part at least one collection container derived from a supply chain matrix involving the commercialization of a fluent material, that but for this system would ordinarily be utilized in such a way as not to confer ecological efficiency. Still a further object of the system creating a NuChain supply chain and disposal chain system by NuPurposing is to provide a system using parts manufactured by single pull injection molding tools. Another object of the system creating a NuChain supply chain and disposal chain system by NuPurposing is to provide a suction canister system that functions as both a bottle docking system and a normal reusable of disposable canister, or a hybrid combination thereof. Another object of the system creating a NuChain supply chain and disposal chain system by NuPurposing is to provide bottle docking capability in a fashion that is ergonomic and easy to use. Another object of the system creating a NuChain supply chain and disposal chain system by NuPurposing is to provide a system embodying few parts for economic cost manufacturing so that if the user does not have bottles available to dock in a canister as collection liners, the system is cost effective and capable of use as a both disposable non-docking and re-usable non-docking canister system. Another object of the system creating a NuChain supply chain and disposal chain system by NuPurposing is to provide permanent autoclavable and re-usable canister systems to reduce the amount of waste entering the waste stream. This Patent Application incorporates by reference herein U.S. Pat. No. 7,185,681. This Patent Application incorporates by reference herein U.S. Provisional patent application Ser. No. 11/787,036.

DEFINITIONS

Bottle dock means a permanent, reusable and/or disposable canister housing systems embodiments of the instant case which is capable of having a fluent material commercialization container transformed and disposed therein for the collection of fluent material waste by the NuPurposing of fluent material commercialization containers into waste collection containers. NuChain means the novel supply chain systems and disposal chain systems created by the NuPurposing of containers such that the transformation and conversion of fluent material delivery containers in collection containers creates a new supply chain and disposal chain systems which links the supply chain of one supply chain and disposal chain systems to the disposal chain of a completely separate supply chain and disposal chain systems. NuPurpose/NuPurposing means the creation of a new purpose for containers such that instead of using a container for an intended purpose and then throwing away such a container realizing no value, the container is utilized for a new purpose like the collection of waste materials, but not limited to that.

BRIEF DESCRIPTION OF THE DRAWINGS

FIG. 2 depicts the transformation of said fluent filled containers from a first condition shown by circled 1-11, being transformed 13 into a waste collection container as shown by circled 2-12, said transformation 13 from condition 1 to condition 2 being carried out within the facility.

FIG. 5 shows the distribution 2, 8 & 5 and receiving of a new empty waste collection container that goes through a facility and/or point of consumption as shown by vector 18 and then leaves the facility and/or point of consumption as a separately produced waste collection container containing waste material.

FIG. 11 give rise to the need for an exchange for users to learn of, access and procure containers for the transformation of, or containers which have been transformed as taught by the instant case, in the event a facility or point of consumption is in the possession of an overabundance of containers. This exchange would allow more containers to be traded, conditioned and transformed and prevent such an overabundance of containers from being discarded and contributed to the waste stream.

FIG. 18 is a top isometric view of a locking, plugging and capping and holding member 27.

FIG. 19 is a top isometric view of a suction canister lid 26 which can also perform as a bottle docking suction canister system lid 26.

FIG. 20 is a top isometric view of a canister 25 which can also perform as a bottle docking suction system canister 25.

FIG. 22 is a side elevation view of blow up of the circle of FIG. 23, showing a canister/lid/plug/bottle seals compression ramp depicting 4 places 26/1, 2, 3, & 4.

FIG. 23 is a side elevation view of lid 26.

FIG. 24 is a bottom plan view of lid 26.

FIG. 31 is a blow up cutaway side elevation view of locking member 27a, lid 26 and canister 25.

FIG. 32 is a blow up cutaway side elevation view of locking member 27a as lid lock hole 26i may be positioned in alignment with any one of canister locking holes 25a1, 2, 3, & 4 in preparation for pressing locking member 27a down to lock the rotation and seal of the canister/lid, and/or the bottle docking assembly.

FIG. 33 is a blow up cutaway view of locking member 27a having been pressed down through lid lock hole 26i and/or any one of canister locking holes 25a1, 2, 3, & 4.

FIG. 37 shows a view of lid 26 And canister 25 and member 27 in a condition sealing lid 26 to canister 25 as well as forming a seal between lid 26, plug 650, bottle 19. FIG. 37 also shows the relationship of lid pillars 26a1, 2, 3, & 4 in physical structuration with canister pillars 25b1, 2, 3, & 4. Each of canister and lid pillar configurations are depicted by the number 28 throughout the drawings defining varying sealing and unsealing juxtaposition relation. FIG. 37 also shows capping member 27 conditioned and positioned so that plug 65 (exemplary plug embodiments may be seen in FIGS. 47-61) is accessible to the suction tip and suction tubing of FIG. 16 (e.g. a conduit) as shown as an exemplary embodiment so that waste materials may be drawn from a source of waste into bottle 19. Lid port 26l is also shown uncapped and available for a connection with a tubing/conduit that is connected at the other end to a source of reduced pressure (not shown).

in FIGS. 40, 44, 42 and 46 show the opposite effect going from the unsealed mode to the sealed mode of operation.

FIG. 44 is a top isometric view of the cutaway of FIG. 43 showing the counter motion between canister 25 and lid 26 to a greater extent operating to seal canister 25 to lid 26 and lid 26 to plug 65 (exemplary plug embodiments may be seen in FIGS. 47-61) with seals having been established to contain and direct a reduced air pressure so that waste material may be drawn into bottle 19 (or canister 25 in the event a bottle is not docked within the system.

FIG. 46 is a top isometric view of cutaway of FIG. 45 depicting canister 25 and lid 26 in a fully sealed orientation.

FIG. 47 is a bottom plan view of an alternative embodiment plug 66 as shown in FIG. 49.

FIG. 48 is a bottom plan view of an alternative embodiment plug 67 as shown in FIG. 50.

FIG. 49 is a side elevation view of a larger reduced pressure aperture of the plug 66 of this view as shown at 66a.

FIG. 50 is a view of a smaller reduced pressure aperture of plug 67 as shown by 67a.

FIG. 51 is a top plan view of plug 66 shown in FIG. 49.

FIG. 52 is a top plan view of plug 67 as shown in FIG. 50.

FIG. 53 shows two side elevation cutaway views of a bottle 19x, plug 71 and cap 23x assembly. The upper view of FIG. 53 shows a plug 71 and cap 23y assembly.

FIG. 54 shows two side elevation cutaway views of a bottle 19y, plug 71 and cap 23y assembly. The upper view shows a cap 23y and plug 71 assembly with the single thread of plug 71 having captured only one lower internal thread of cap 23y.

FIG. 55 shows two side elevation cutaway views of a bottle 19z plug 71b, and cap 23z assembly. The upper view of FIG. 55 shows plug 71 having been removed from cap 23z. These FIGS. 47-55 shows how the single thread of a plug 71 for example may be captured by a cap 23x, 23y and 23z to remove a plug 71 for example that has been inserted into the pour spout of a bottle 19x, 19y and/or 19z. Without such a mechanism, an operator may struggle to remove a plug 71 form a bottle 19x, 19y and/or 19z and the instant case provides the same cap that the bottle was commercialized in as a tool for removal of a plug in such a fashion that the operator is not required to directly touch a contaminated plug.

DETAILED DESCRIPTION OF THE DRAWINGS

Figure 1:
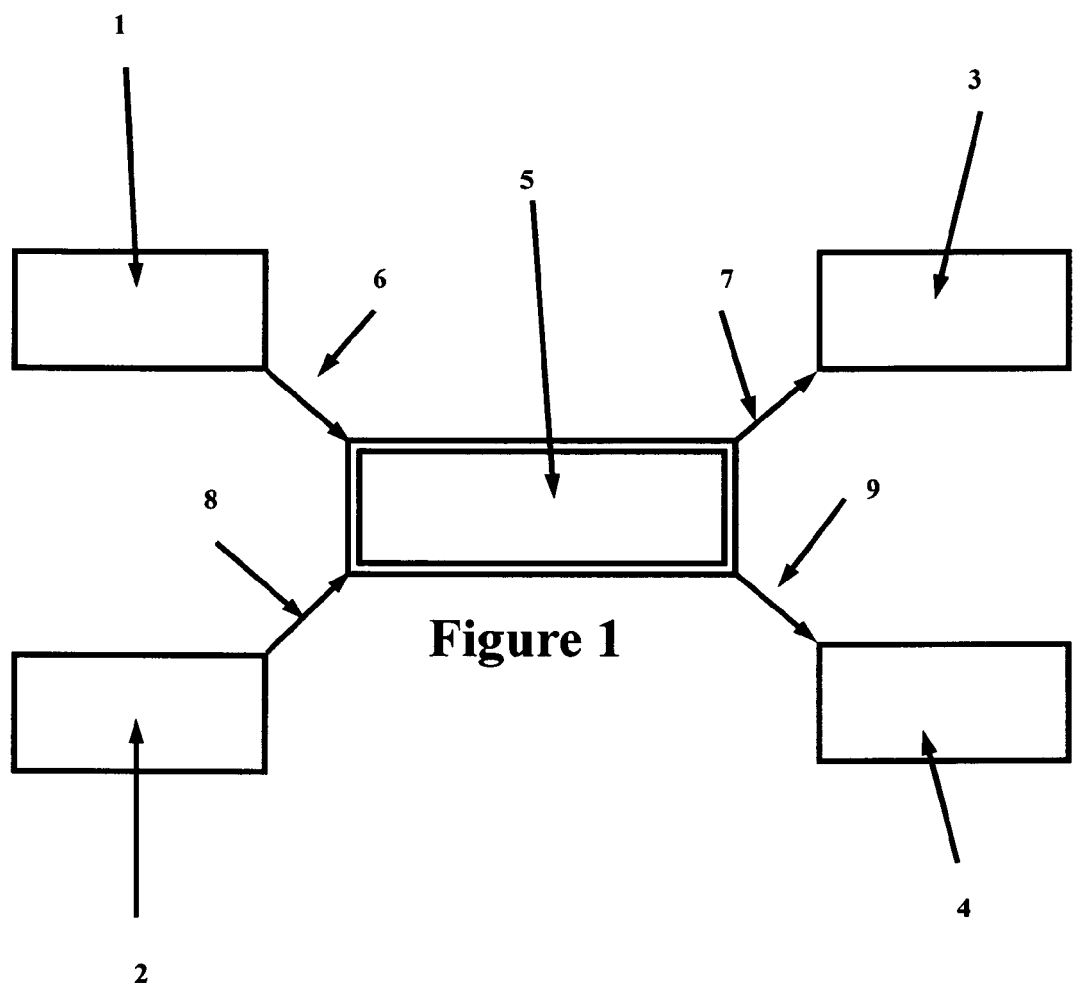
FIG. 1 is a drawing of a prior art supply chain apparatus showing how a fluent material filled container 1 may be distributed to a facility 5 and once the fluent material is used, an empty container 3 is then discarded into the garbage. Similarly, a separately purchased empty container 2 may also be distributed to the facility 5 and when that empty container is used or filled, it goes into a fluent filled waste container disposal chain apparatus 4.

Turning to FIG. 1. FIG. 1 shows two separate prior art supply chain and disposal chain apparatus's. These two prior art supply chain and disposal chain apparatus's FIG. 1 shows a filled container 1 in a new condition. Number 2 shows an empty separately produced prior art collection container in a new condition. Number 3 shows an empty prior art container of container 1 that is being discarded empty as garbage into the waste stream. Number 4 is a used empty prior art collection container of number 2. Number 5 shows a facility and/or point of consumption. Number 6 shows a prior art supply chain transportation vector showing the receiving of container 1 by a facility 5 from manufacturing, or received at a point of consumption. Number 7 is a prior art supply chain transfer vector showing a transfer of empty prior art container 3 from facility 5 to a waste receiving location. Number 8 depicts a prior art supply chain transfer vector showing the receiving of a separately produced prior art empty collection container 2 by facility 5 (or a point of consumption) from manufacturing. Number 9 shows a prior art supply chain apparatus transfer vector of contaminated and used prior art container 2 being transferred from facility 5 to a waste receiving location.

Figure 2:
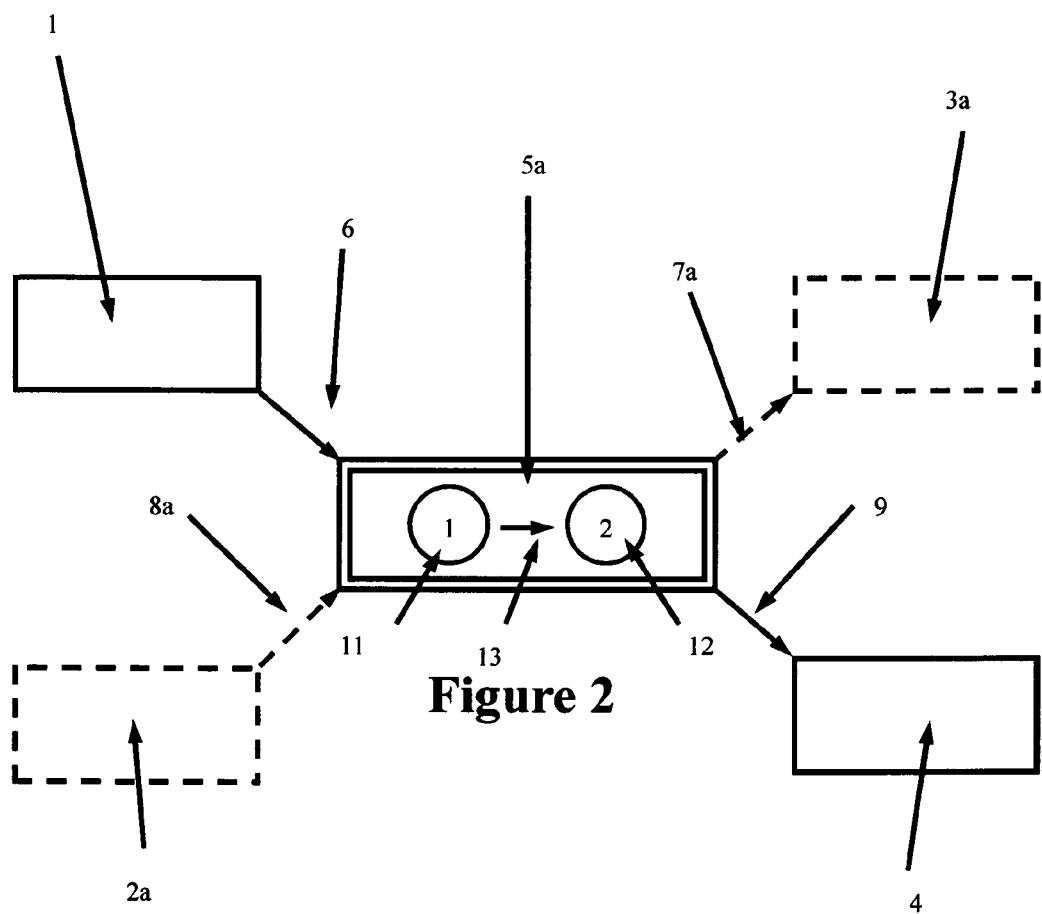
FIG. 2 is a drawing of a NuChain supply chain apparatus showing the elimination of supply chain apparatus 2a and disposal chain apparatus 3a wherein a fluent material container is transformed into a collection container linking the supply apparatus of one supply and disposal chain apparatus 1 with the disposal apparatus of a second supply and disposal chain apparatus 4. This is emphasized by the broken lines depicting the eliminated portions the aforementioned apparatus.

Turing to FIG. 2. FIG. 2 shows in broken lines the elimination of empty prior art waste collection container 2 as depicted by 2a and the elimination of the entire prior art supply chain apparatus of container 2-8a. Number 7a shows the elimination of the prior art supply chain vector apparatus of empty prior art collection container 1 and 3a shows the elimination of prior art supply chain apparatus container 1 as an empty unused prior art supply chain container. Also shown within facility 5a circle one is depicted by 11 which defines container 1 in a first condition. Supply chain apparatus transfer vector 13 represents the conditioning and transformation of container 1 into a different state in so far as it is conditioned for the collection of waste as a collection container.

Figure 3:
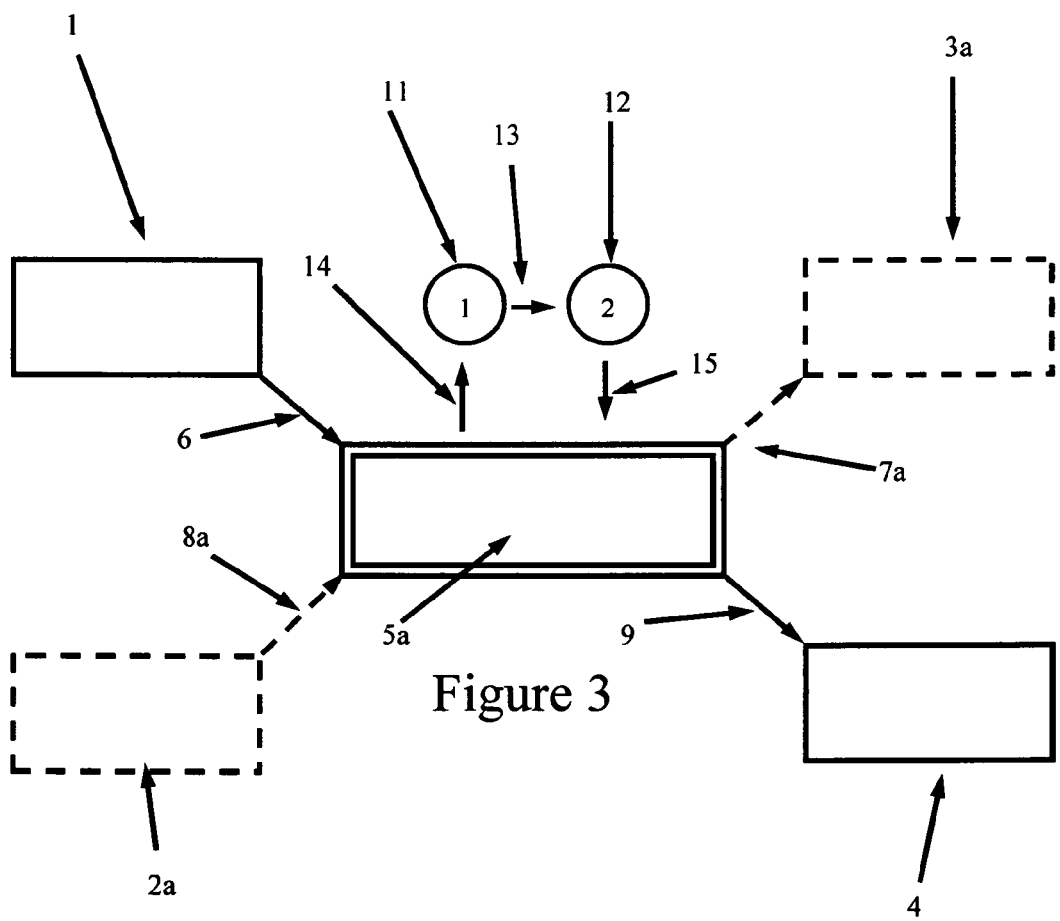
FIG. 3 shows the same drawing as FIG. 2 with the exception that the fluent filled containers circled 1 converts and is transformed 13 from a first condition circled 1-11, to a second condition 2-12 of a waste collection container circled 2-12 as shown by transfer vector 14 leaving the facility 5 and by transfer vector 15 as returning to the facility transformed into a second condition. It is understood that the process shown in FIG. 3 does not depend on the containers described being the same actual physical embodiments in every instance, however in some instances the containers will be the same physical embodiments associated with facility 5 of FIGS. 1 and 5a of FIG. 2 and in other instances the containers shown will be containers derived from separate facilities in that one of the underlying concepts is that NuPurposed containers may be derived from other sources.

Turning to FIG. 3. FIG. 3 shows the supply chain apparatus of FIG. 2 however the conditioning and transformation of container 1 as depicted by 11, 13 and 12 into a different state for collecting contaminated waste materials and conditioning occurs outside of the facility where the point of consumption of container 1 took place. Supply chain apparatus transfer vector 14 defines the container being transferred to a location outside of facility 5a and supply chain apparatus transfer vector 15 shows container 1 being transferred back to facility 5a in its conditioned and transformed state for use in a different state as a contaminated waste collection container inside facility 5a. It is understood that facility 5a may be the same facility or a different facility in that container 1 may be engaged in a NuPurposing exchange (or an online NuPurpose container trading exchange). Container 1 enters facility 5a for egress of its fluent materials and is conditioned and transformed into a waste collection container but then may ingresses fluent waste material at a different facility as a result of having been subject to procurement and acquisition rights of a completely different facility, and/or a completely separate point of consumption in a different department of facility 5a or for a different consumption or different use than facility 5a.

Figure 4:
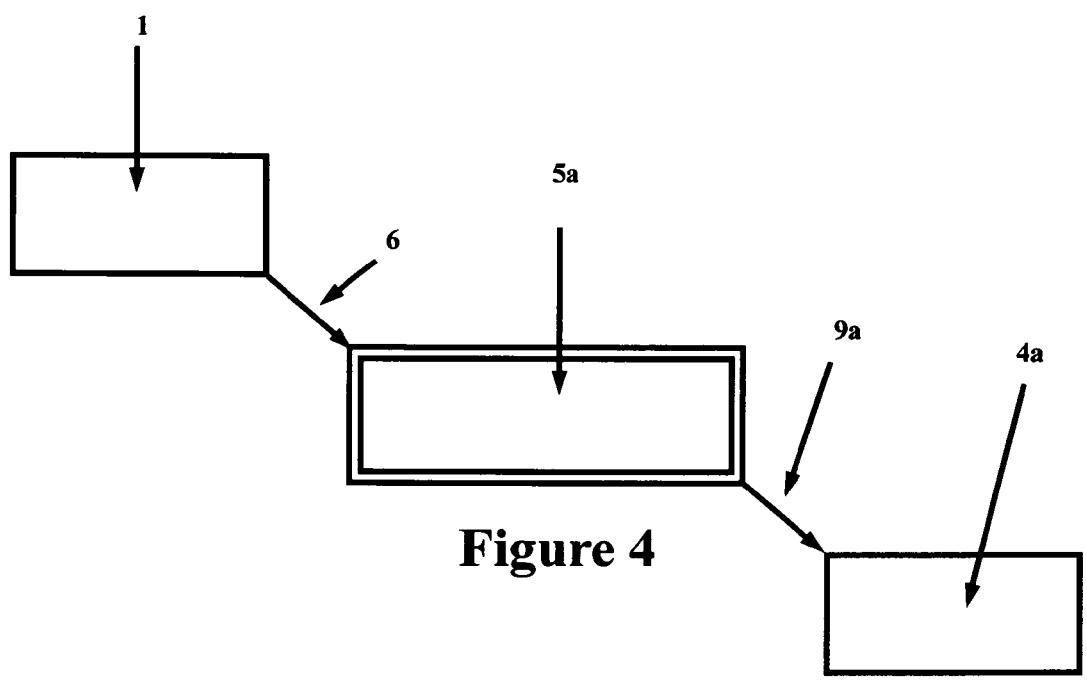
FIG. 4 shows a drawing of a NuChain apparatus wherein the distribution and receiving of empty incoming separately produced waste collection containers of FIGS. 1, 2 and 3 is eliminated, and the disposal of the empty fluent material containers are eliminated and the supply chain apparatus of a first supply chain apparatus 1 is linked to the disposal chain apparatus of a second disposal chain apparatus 4 establishing a NuChain supply chain and disposal chain apparatus.

Turning to FIG. 4. FIG. 4 shows a NuChain supply chain and disposal chain apparatus having eliminated the portions of the supply chain (2a and 8a) apparatus and the disposal chains (7a and 3a) apparatus of FIG. 3. The broken lines of 2a, 8a and 7a and 3a having been eliminated. FIG. 4 shows the NuChain supply chain and disposal chain apparatus being defined as number 1 which defines a fluent material distribution container. Number 6 defines a supply chain apparatus transfer vector toward facility 5a where a point of consumption occurs and a transformation of container 1 into a waste collection container may occur. Number 9a is a supply chain apparatus transfer vector showing a container 1 having waste material contained therein and being transferred away from facility 5a towards a waste receiving location.

Figure 5:
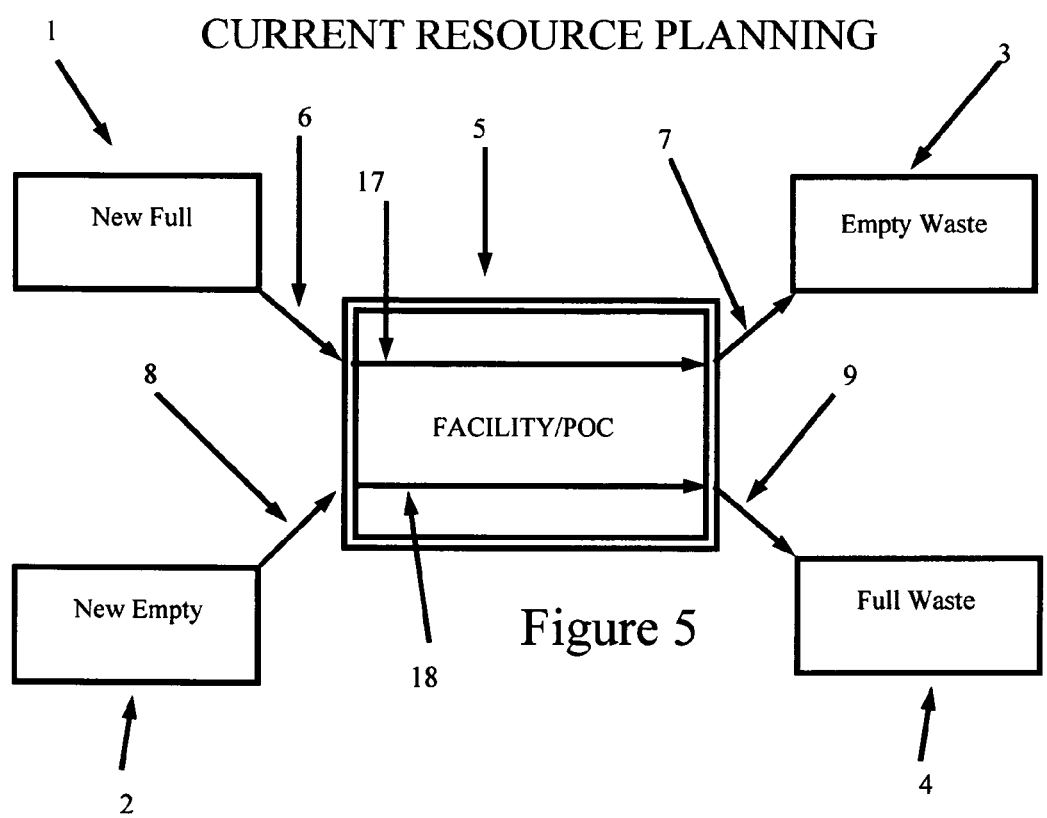
FIG. 5 shows a prior art drawing of a first supply chain and disposal chain apparatus 1, 6, 17, 7 & 3 and a second supply chain and disposal chain apparatus 2, 8, 18, 9 & 4 wherein a fluent material container 1 is processed through a facility and/or toward and away from a point of consumption as shown by transfer vector 17 and then leaves a facility/point of consumption 7 as an empty waste container whereby no container transformation or reconditioning occurs. In addition

Turning to FIG. 5. FIG. 5 shows two separate prior art supply chain and disposal chain apparatus's prior art modes of operation involving current prior art status quo enterprise resource planning showing the supply chain apparatus transfer vectors and container flow of 6, 17 and 7 representing how a new full container is received by a facility 5 and flows through a facility at 17 and then flows away from a facility at 7 wherein the prior art container becomes an empty container 3 as waste/garbage lacking further utility (i.e. not NuPurposed). Also new empty prior art collection container 2 is shown by supply chain apparatus transfer vector 8 as being received by a facility 5 going through the facility and going away 9 from the facility 5 going from a newly procured new empty prior art waste collection container being delivered to a facility in a new condition into a waste collection container for having fluent material waste enclosed therein.

Figure 6:
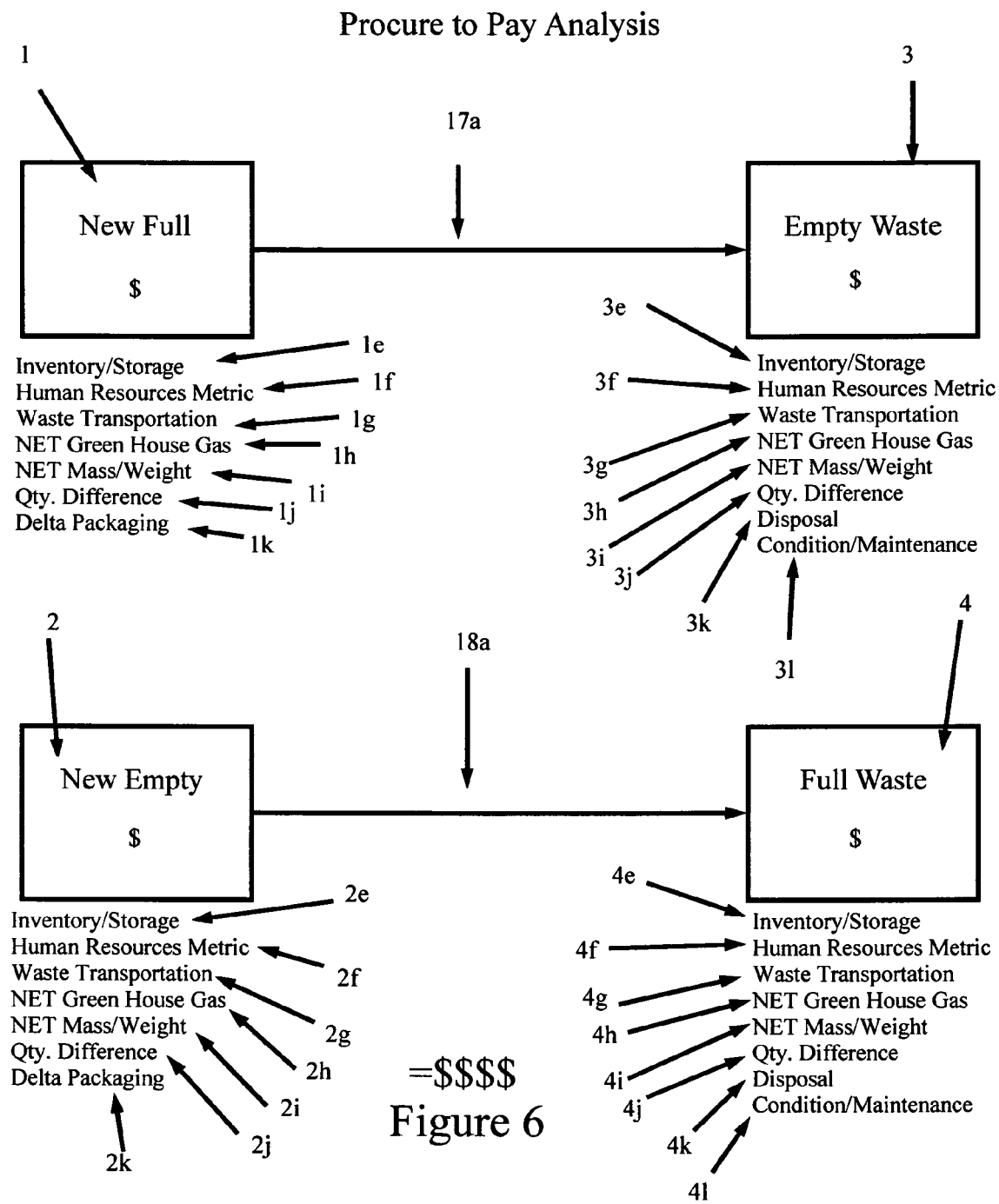
FIG. 6 shows a first prior art supply chain and disposal chain apparatus and a second prior art supply chain and disposal chain apparatus and some of the cost metrics associated with each. On a procure to pay valuation basis certain cost appraisal factors shown, such as 1e-1k, 2e-2k, 3e-3l and 4e-4l as well as other metrics that are appraisable (not shown) may be appraised for each supply chain and disposal chain apparatus that is associated with a container purchasing decision as it relates to a point of consumption and or a facility who obtains economic valuations for each.

Turning to FIG. 6. FIG. 6 shows a prior art supply chain apparatus showing separately and individually on a procure to pay appraisal basis a prior art an enterprise resource planning and management of prior art container 1 and prior art container 2 as they each separately and individually flow along their respective separate supply chain and disposal chain apparatus's pathways as they individually and separately flow through a facility in accordance with the prior art depicted by 17a and 18a. New full prior art container 1 is shown having cost associated with its procurement and use such as inventory/storage 1e, human resource metrics 1f, waste transportation metrics 1g, new green house metrics 1h, net mass/weight metrics 1i, quantity difference 1j, and delta packaging metrics 1k. In addition, prior art container 1 becomes an empty waste container along 17a and has no further value which adds costs associated therewith such as inventor/storage metrics 3e, human resource metrics 3f, waste transportation metrics 3g, net green house gas metrics 3h, net mass/weight metrics 3i, quantity difference metrics 3j, disposal metrics 3k, and condition/maintenance metrics 3l. In addition, newly procured empty prior art waste collection container 2 has associated costs such as inventory/storage metrics 2e, human resource metrics 2f, waste transportation metrics 2g, net green house gas metrics 2h, net mass/weight metrics 2i, quantity difference metrics 2j, and delta packaging metrics 2k. In addition, used waste collection container 4 has associated costs such as inventory/storage metrics 4e, human resource metrics 4f, waste transportation metrics 4g, net green house gas metrics 4h, net mass/weight 4i, quantity difference 4j, disposal metrics 4k and condition/maintenance metrics 4l. This is not meant to be a complete list of costs however the lists associated with containers 1, 2, 3, & 4 of FIG. 6 provides enough of a representative example to teach the appraisal concept for the purposes of appraising the value of NuPurposing.

Figure 7:
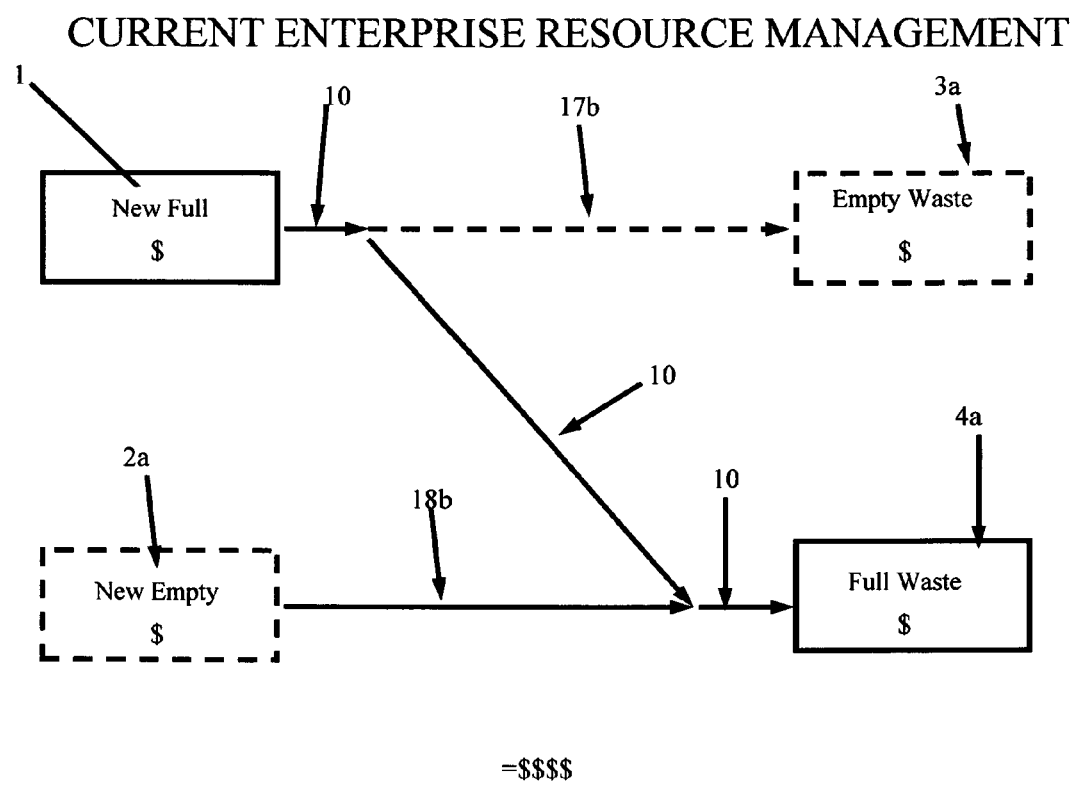
FIG. 7 shows a NuChain enterprise resource planning supply chain and disposal chain apparatus connecting the two (1, 17a, & 3 and 2, 18a & 4) prior art supply chain and disposal chain apparatus of FIG. 6 whereby a fluent material filled product distribution container 1 has transformed (10, 10 & 10) into a waste collection container 4a and creates a new value defined as a NuChain enterprise resource planning process and NuChain supply and disposal chain apparatus.

Turning to FIG. 7. FIG. 7 shows the NuChain enterprise resource planning supply chain and disposal chain system by the elimination of prior art supply chain costs and prior art disposal chain costs by the elimination of new empty collection container procurement as depicted by the broken lines 2a and the associated prior art supply chain apparatus costs at 18b and also defined by the cost savings from elimination of the prior art supply chain apparatus costs 2, 2e, 2f, 2g, 2h, 2i, 2j, 2k of FIG. 6 as is depicted by broken arrow lines 2a and 18b of FIG. 7 and in addition by the elimination of the separate prior art disposal chain apparatus costs of 3, 3e, 3f, 3g, 3h, 3i, 3j, 3k and 3l as depicted by broken lines 17b and 3a in FIG. 6 by eliminating the procurement costs of a new empty prior art collection containers and by eliminating the disposal costs of prior art used containers going into the trash. New full collection container 1 becomes the collection container 4a as a NuPurposed container creating a NuChain supply chain and disposal chain system. Container 1 is transformed and conditioned for the ingress of air under reduced pressure forces and for the ingress of waste material and number 10 is marked in three places of FIG. 7 as the NuChain supply chain apparatus and disposal chain apparatus transfer vector that connects new full container 1 with the disposal chain of fluent waste material as depicted by 4a as created by NuPurposing containers as taught by the instant case.

Figure 8:
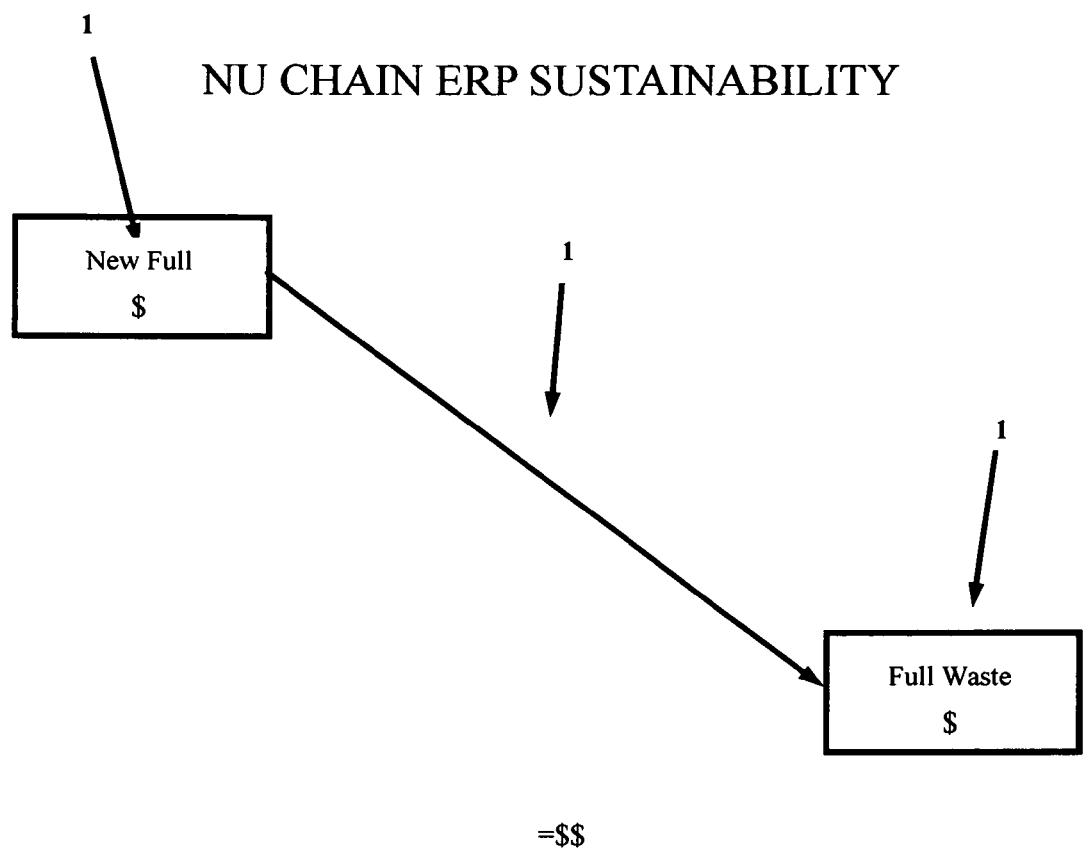
FIG. 8 shows show's a new NuChain Enterprise Resource Planning sustainability and environmentally preferred supply chain and disposal chain apparatus schematic whereby a new filled fluent material container (1 upper left) may be distributed to a facility and/or a point of consumption as such a container is conditioned and transformed to collect waste material (1 lower right).

Turning to FIG. 8. FIG. 8 shows a direct supply transfer chain 1 (center) connecting new full container 1 (upper left) to be conditioned and transformed to ingress waste materials 1 (lower right).

Figure 9:
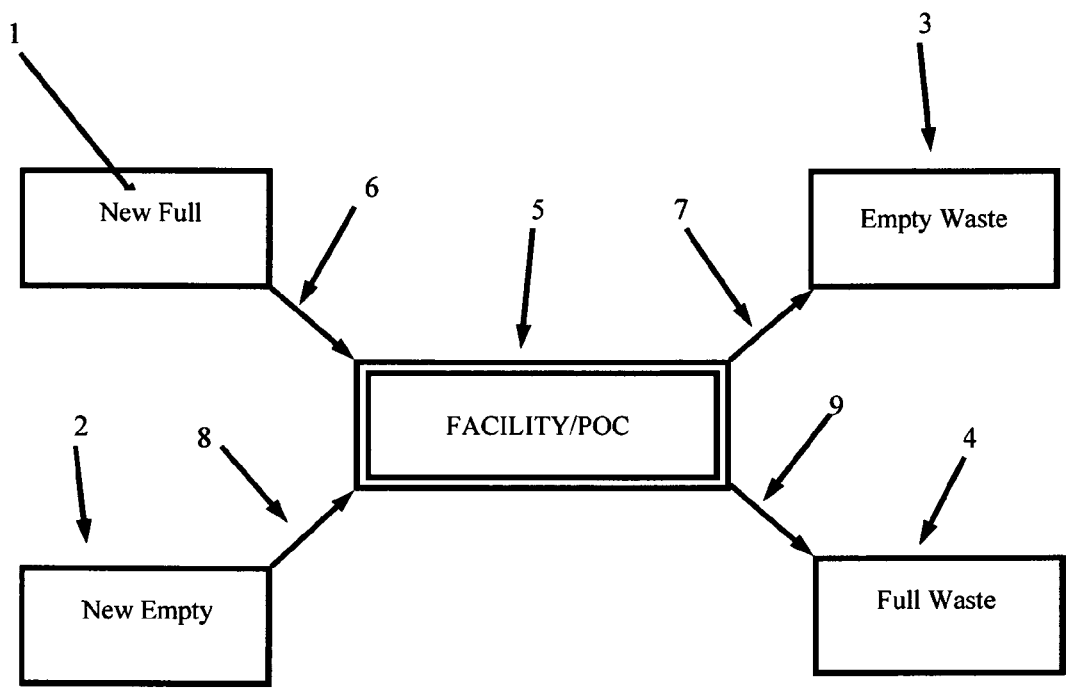
FIG. 9 shows a prior art schematic which shows the prior art supply chain (1, 6, 5, 7 & 3) and disposal chain apparatus (2, 8, 5, 9 & 4) wherein a full fluent material commercialization container and a separate second supply chain and disposal chain apparatus embodying a newly delivered empty collection container 2 which gives rise for the need for a container transformation of the instant case and gives rise for the need for a online container trading exchange so that facilities and points of consumption may benefit from empty fluent material distribution containers which may be exchanged and traded between departments of a facility, between point of consumption associated with various supply chain and disposal chain apparatus, between separate facilities, so that a mechanism exists for users needing access to NuPurposed, transformed and conditioned containers to find and procure from facilities and/or points of consumption where there may be an overabundance of such containers to be NuPurposed and utilized by a user which is not the same user of the first container embodied in the first supply chain and disposal chain apparatus.

Turning to FIG. 9. FIG. 9 shows a prior art schematic of FIG. 1 and gives rise to the need of a NuChain enterprise resource planning and container NuPurposing container trading exchange that would benefit society from by disclosing an overabundance of containers that may not have the need to be NuPurposed in a particular facility.

Figure 10:
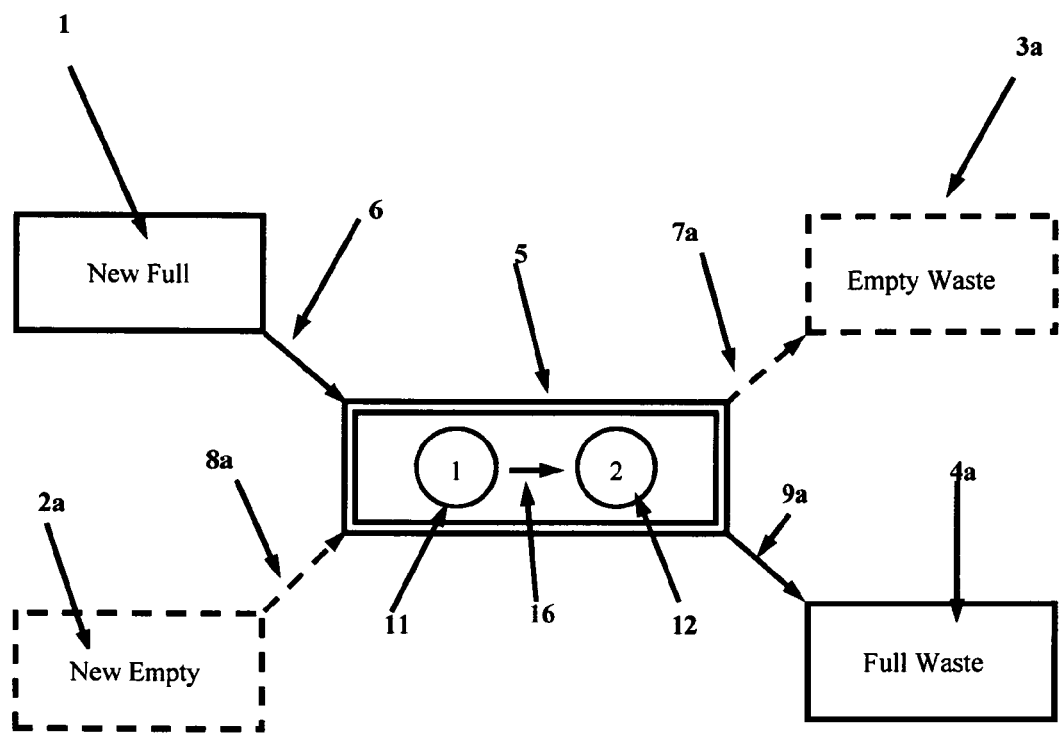
FIG. 10 shows a NuChain supply chain and disposal chain apparatus where the used fluent material distribution container has been transformed from a condition one-circled 1 to a condition two-circled 2 and gives rise to the need for an online exchange in the event there may be an overabundance of containers.

Turning to FIG. 10. FIG. 10 shows the supply chain of FIG. 2 showing the elimination of 2a, 8a, 7a and 3a giving rise for the need of an online container conditioning exchange for the procurement and transformation of containers where there is an overabundance of containers for NuPurposing whereby a particular facility may not have the need to NuPurpose and where another facility may benefit from the procurement of and conditioning and transforming of containers for NuPurposing in their separate facility. These containers may be exchanged between facilities, and/or separate entities for the purposes of transforming containers into a condition for NuPurposing into waste material ingressing containers. In the event that an overabundance of containers exist and may be transformed and conditioned for a new purpose, and online exchange will allow procurers to access and procure such containers.

Figure 11:
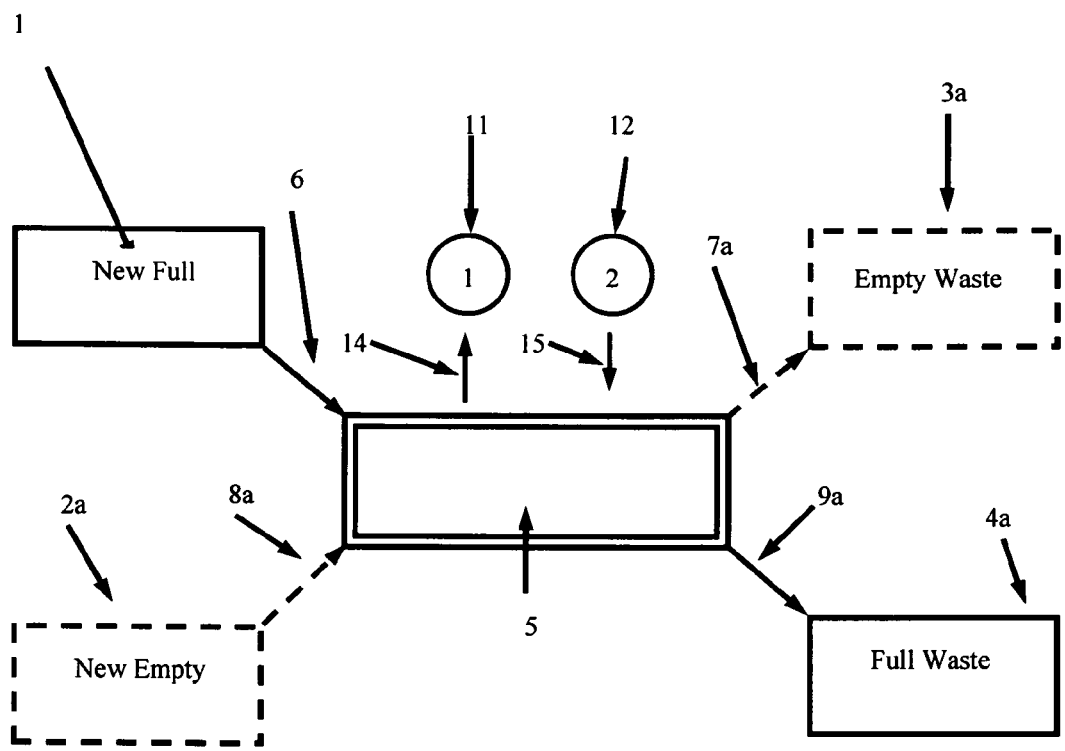
FIG. 11 shows a similar NuChain supply chain apparatus as FIG. 10 however the transformation of the new full commercialization container transforms from condition 1 to condition 2 is a process that occurs outside a facility/point of consumption as shown by transfer vectors 14 and 15.

Turning to FIG. 11. FIG. 11 shows a NuChain supply chain and disposal chain enterprise resource planning model that teaches an online container and trading exchange user what to evaluate when considering a NuChain procurement of containers for NuPurposing in a facility that may need to process containers to condition for transformation into NuPurposed containers. This schematic gives rise to an online NuPurposing container procurement exchange in the event a facility has a overabundance of containers that may be NuPurposed by, or for, another facility or in the event a facility has an inadequate supply of containers for NuPurposing at the volume levels desired and another facility wishes to procure containers for NuPurposing to make up for the inadequate volume. Such an online NuPurpose and/or NuChain container trading exchange may be between different departments of the same facility, different departments of different facilities, between different entities, between different facilities etc. Supply chain apparatus transfer vectors 14 and 15 show that the conditioning and or transformation of containers into a different state may be carried out by a separate facility. An online container conditioning and trading and procurement exchange would allow separate facilities to become aware of and have access to the procurement of NuPurpose collection containers from facilities that have an abundance of collection containers without having to procure separately produced prior art empty collection containers 2a, preventing the expense of the associated costs, as well as the supply chain costs of disposal.

Figure 12:
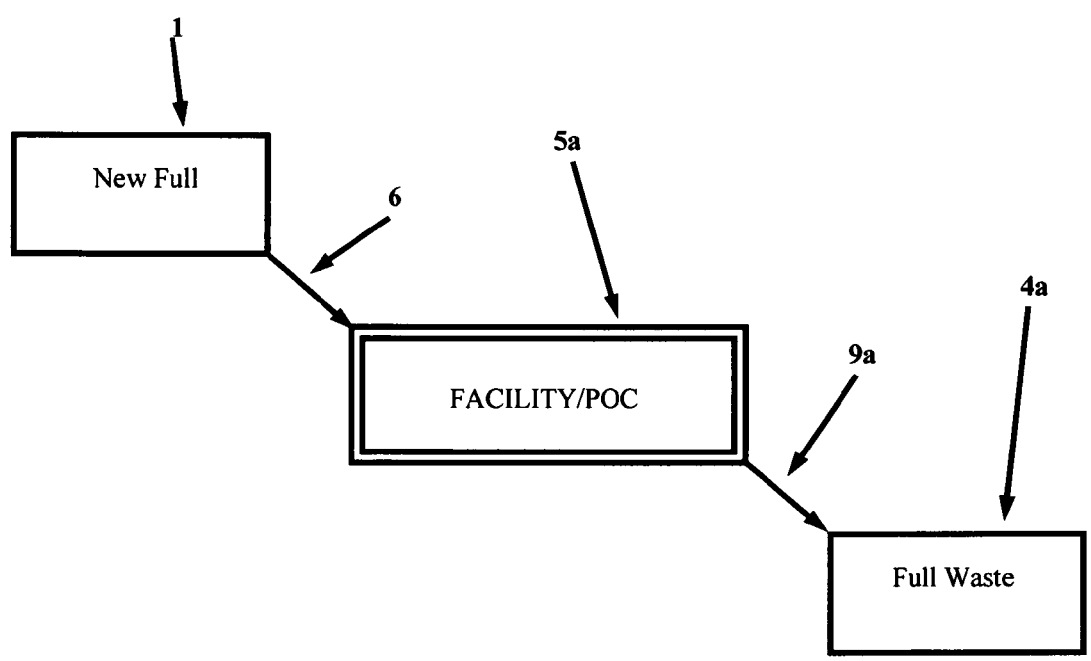
FIG. 12 is a drawing of a NuChain supply chain and disposal chain apparatus which depicts the commercialization, distribution and receiving of a new full fluent material container 1 being received 6 by a facility/point of consumption 5a, being consumed at a point of consumption and then being conditioned for transformation into a waste collection container.

Turning to FIG. 12. FIG. 12 shows the NuChain supply chain system and disposal chain apparatus depicting the connection between the two separate prior art supply and disposal chains as shown in FIGS. 9, 6, 5 and 1. FIG. 12 shows a NuChain that is created by the NuPurposing of containers as taught by the instant case. NuPurposing containers creates a streamlined and cost effective practice for the delivery of new materials and for the collection of waste materials whereby container 1 is received by facility 5a along transfer vector 6 and container 1 having been conditioned and transformed into a collection container by NuPurposing leaving facility 5a as a collection container 4a along transfer vector 9a.

Figures 13, 14, 15:
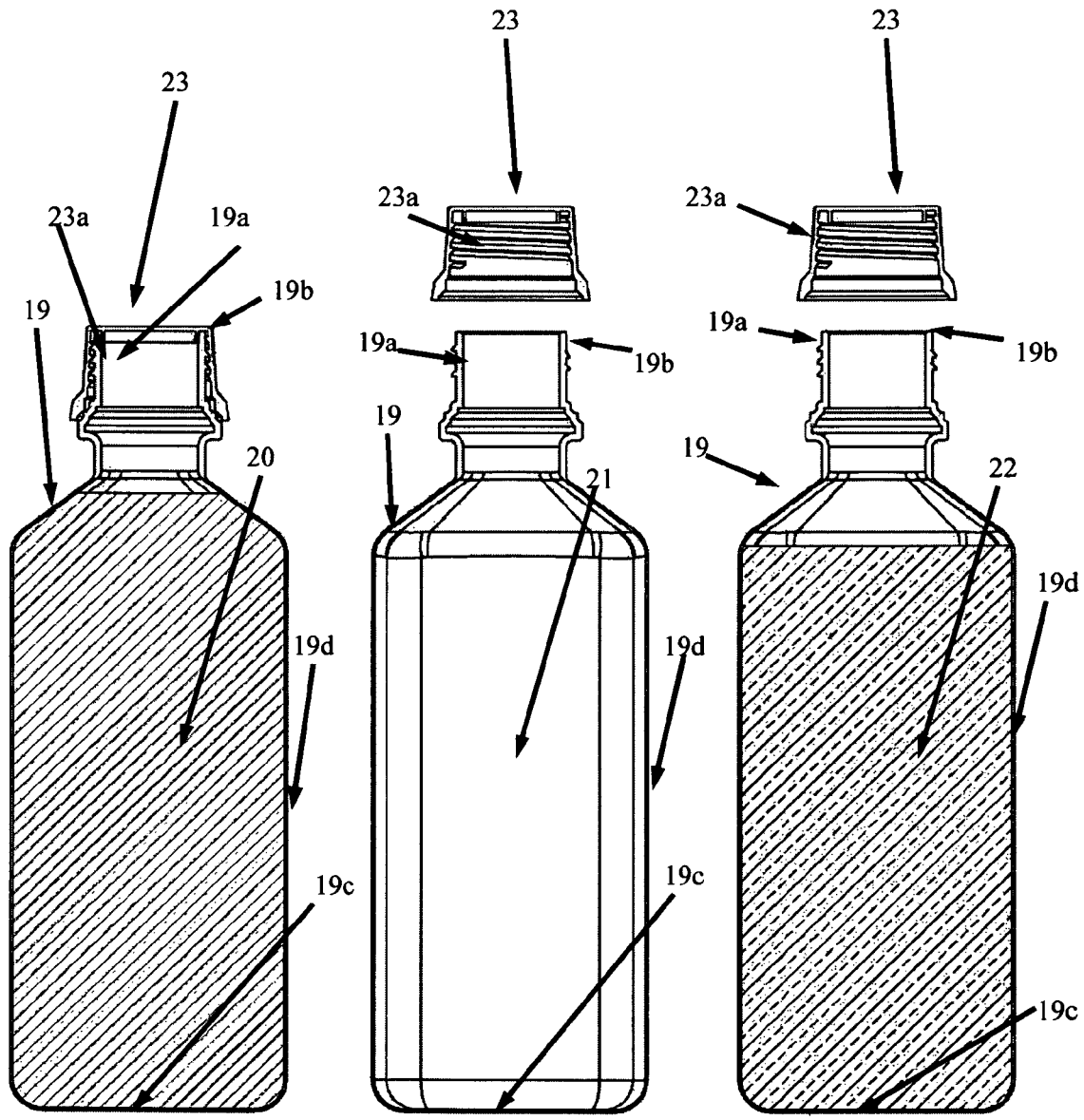
FIG. 13 is a side elevation cutaway view of a newly distributed fluent material commercialization container 19 containing unused fluent material 20.
FIG. 14 is a side elevation cut away view of a fluent material distribution container wherein at least a portion of said fluent material has egress out of said container 19 leaving cubic volume available inside 21 of container 19 for the ingress of waste material. Container 19 in FIG. 14 either has been conditioned or is in a position to be conditioned for the collection of waste materials. Cap 23 of container 19 may be held in abeyance during the conditioning and transformation of container 19.
FIG. 15 is a side elevation cutaway view of container 19 having been conditioned and transformed for the collection of waste material. The waste material 22 is seen in FIG. 15. Cap 23 may be replaced on to container 19 to provide a leak proof seal to prevent waste leakage during a disposal process of a disposal chain apparatus. It is understood that cap 23 of FIGS. 13, 14 and 15 may be the same cap or a different cap whereas many containers are mass produced with the same dimensional specification and will serve the purpose of sealing a waste container 19 of FIG. 15. Alternative seals may be used for sealing container 19 to seal waste 22 inside container 19 as shown in FIG. 15.

Turing to FIG. 13. FIG. 13 side elevation cutaway view showing a bottle 19 in a fluent material distribution condition. Bottle 19 is shown having a new fluent material 20 contained therein by cap 23. Cap 23 has internal threads 23a. Bottle 19 shows threads 19a and a pour spout at 19b. Bottle 19 also has an outside perimeter 19d and a bottom 19c.

Turning to FIG. 14. FIG. 14 is a side elevation cutaway view showing bottle 19 having egressed its fluent material 20 of FIG. 13. Bottle 19 is shown having space inside available in cubic volume to ingress waste material as shown by 21. Bottle 19 is shown having cap 23 removed.

Turning to FIG. 15. FIG. 15 is a side elevation cutaway view showing bottle 19 having ingressed waste material as shown by 22. FIG. 15 shows bottle 19 as having been bottle docked and ingressed waste materials 22.

Figure 16:
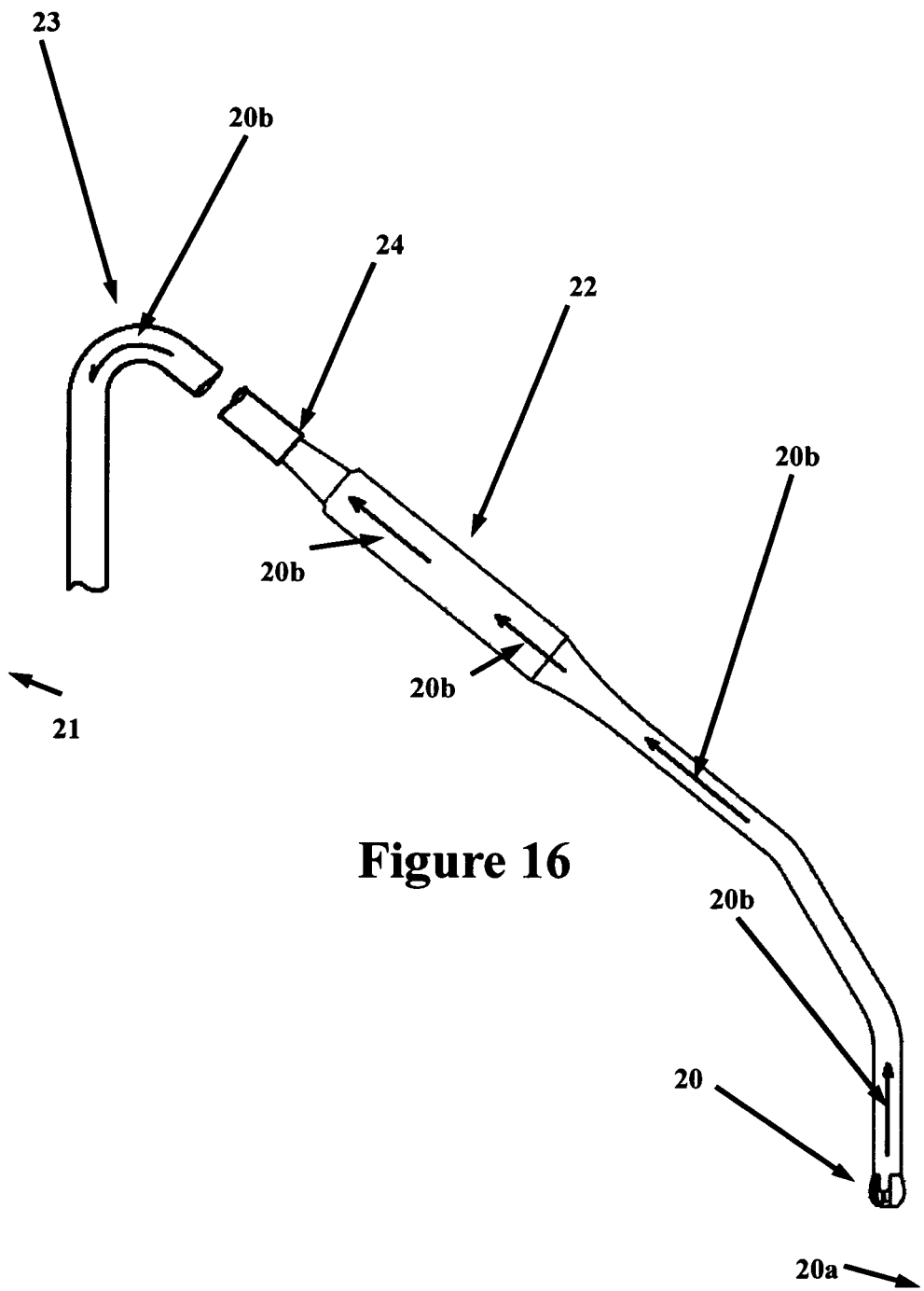
FIG. 16 is a side elevation view of a suction tip 22. Suction tips are commonly referred to as suction wands and may go by other common names such as Argyle Suction tips, Tonsil Suction tips, Pool suction tips, Adson suction tips, Yankauer Suction tips, Pediatric suction tips, Frazier tips etc. etc. The suction tip as shown in connection with a suction tubing 23 are commonly connected to form a conduit for waste material being drawn from a source of waste material into collection container such as container 19 as taught by the instant case. Said conduits are commonly used in many forms of care such as open surgery, and other procedures such as arthroscopic surgery, endoscopic procedures, robotic surgery, minimally invasive procedures, computer assisted surgery as well as such conduits are used in procedures that are performed on all parts of a human or animal.

Turning to FIG. 16. FIG. 16 is a side elevation view showing a suction tip commonly known in the art as a suction wand showing a connection 24 to a suction tubing 23. Number 21 represents a source of reduced pressure which draws negative pressure from external to suction tip 22 at 20 along the arrows 20b shows in five places as the negative draw pressure draws waste material from a source of waste at 20a and along the conduit formed by the tip and tubing as the arrows are depicted in five places of FIG. 16 which passes through the connection 25 and through the suction tubing 20b toward a canister for the deposit of waste material whereby negative draw force at 21 pulls vacuum forces that draw waste materials into canister 25 and or bottle 19 through air passage apertures of exemplary plug embodiments as shown in FIGS. 47-61.

Figure 17:
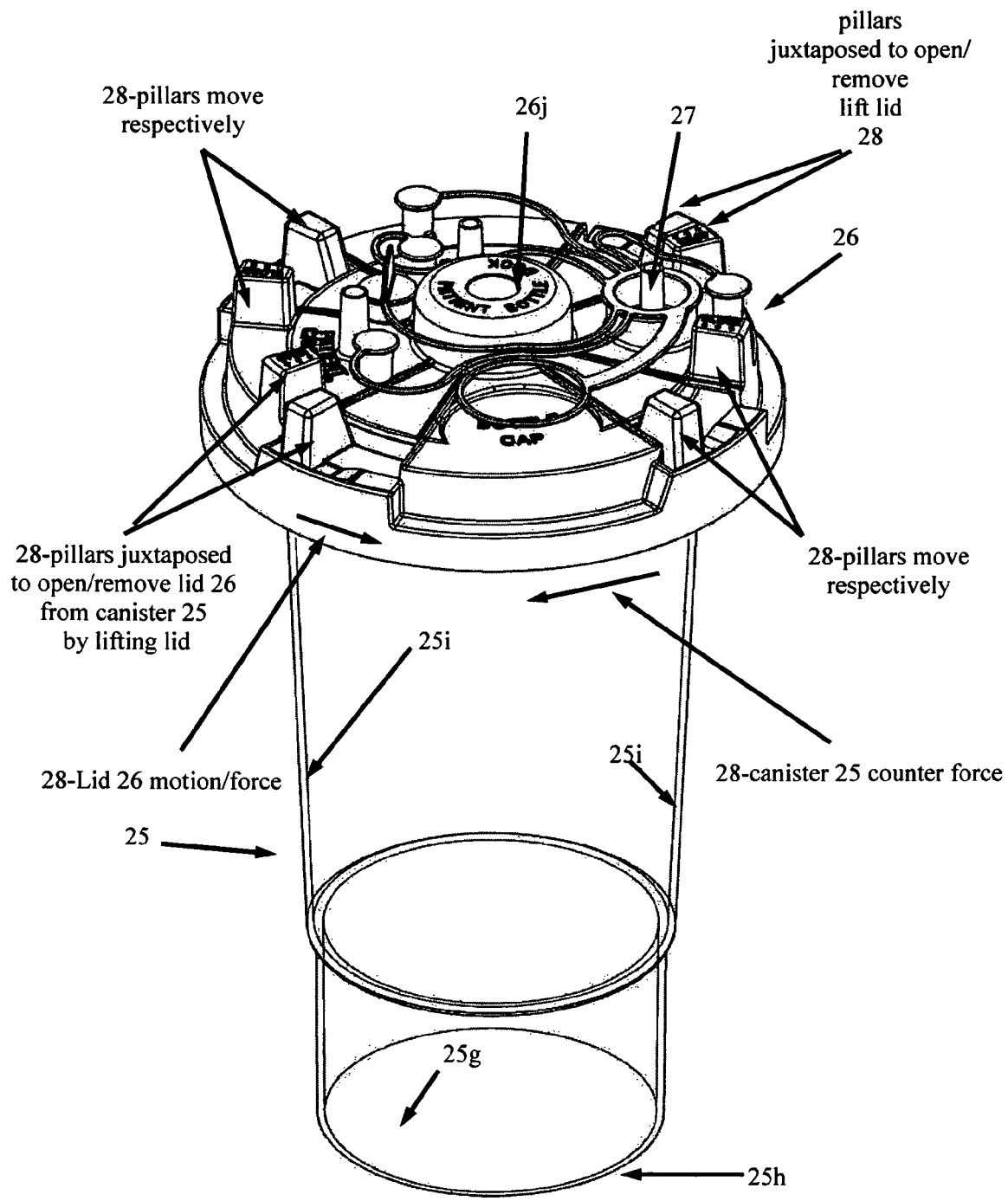
FIG. 17 is a top isometric view of a bottle docking suction canister system conditioned to operate as normal suction canister in the instance where no bottles are available to dock inside the system.

Turning to FIG. 17. FIG. 17 is a top isometric view showing the bottle docking system as taught by the instant case assembled in the operative mode of an ordinary suction canister without bottle docking a bottle 19 inside. Lid 26 is shown in the spatial and temporal process of being assembled to canister 25. Capping member 27 is disposed accordingly on lid 26. Canister pillars 25b1, 2, 3, & 4 of FIG. 25 can be seen projecting up through lid pillar apertures 26h1, 2, 3, & 4 of FIG. 21. Lid aperture 26j is shown unplugged, however during use as an ordinary suction canister lid aperture 26j would be plugged by cap member 27k of FIG. 18. Also cap member 27c of FIG. 18 would be capped. Canister 25 is shown having an outside bottom 25h and an inside bottom 25g. Canister 25 is shown having inside walls in two places at 25i.

Turning to FIG. 18. FIG. 18 is a top isometric view of capping member 27. Capping member 27 comprises cap 27c which caps tubing port 27b of 27. Cap 27 also comprises a plurality of retainers. Retainer 27f positions and retains cap 27c. Retainer 27o positions and retains lid lock 27a. Retainer 27j positions and retains cap 27i. Retainer 27l positions and retains cap 27k. Retainer 27p positions and retains cap 27m. Retainer 27h positions and retains cap bottle cap ring holder 27g. Plug 27b plugs lid pour spout 26p and positions all aspects of cap member 27 with respect to features of lid 26. Plug 27b is sized and shaped to fit and plug lid pour spout 26p of lid 26. Lid lock 27a is retained and positioned for easy depression into lid lock hole 26i of lid 26. Cap 27i is retained and positioned to cap vacuum tubing port 26l of lid 26. Lid plug cap 27k is retained to plug center lid aperture 26j. Cap 27m is retained and positioned to cap patient tubing connection port 26k of lid 26.

Turning to FIG. 19. FIG. 19 is a top isometric view of lid 26 showing the detailed features of lid 26. Lid 26 comprises four lid pillars 26a1, 2, 3, & 4. 26i represents the lid lock hole. 26k comprises the suction tubing connection port for a patient suction tubing. 26l comprises a suction tubing connection port for a source of vacuum. 26p comprises a pour spout. 26j comprises a center aperture for a patient suction tubing to be used during a bottle docking mode of operation by connection to a patient tubing connection on a bottle plug (not shown). 26h1, h4, h3, & h2 each comprise an aperture for acceptance passage and movement of canister pillars 25b1, 2, 3, & 4. 26f1, 2, 3, & 4 comprise an ascending sealing ramp that is positioned to contact the bottom side 25b1e, 2e, 3e & 4e of canister pillars 25b1, 2, 3, & 4. Ultimately when in the fully compressed condition lid contact surfaces 26g1, 2, 3, & 4 engage in contact with canister pillar bottom edge 25b1h, 2h, 3h & 4h as counter rotational motion between canister 25 and lid 26 compresses lid 26 and canister 25 together to form a seal therebetween.

Turning to FIG. 20. FIG. 20 is a top isometric view canister 25. Canister 25 comprises canister pillars 25b1, 2, 3, & 4. 25c1, 2, 3, & 4 comprise the lid lift ramp. 25a1, 2, 3, & 4 comprise canister lock hole. Flat surface 25e marked in four places comprises the top flat contact surface for contact between lid 26 and canister 25. 25d marked in three places shows the canister seal that seals with lid seal 26o as shown in FIG. 24. Canister seal is disposed at the top of the inside rim of canister 25 for sealing canister 25 for sealing with the annular lid seal 26o of lid 26 as shown in FIG. 24.

Figure 21:
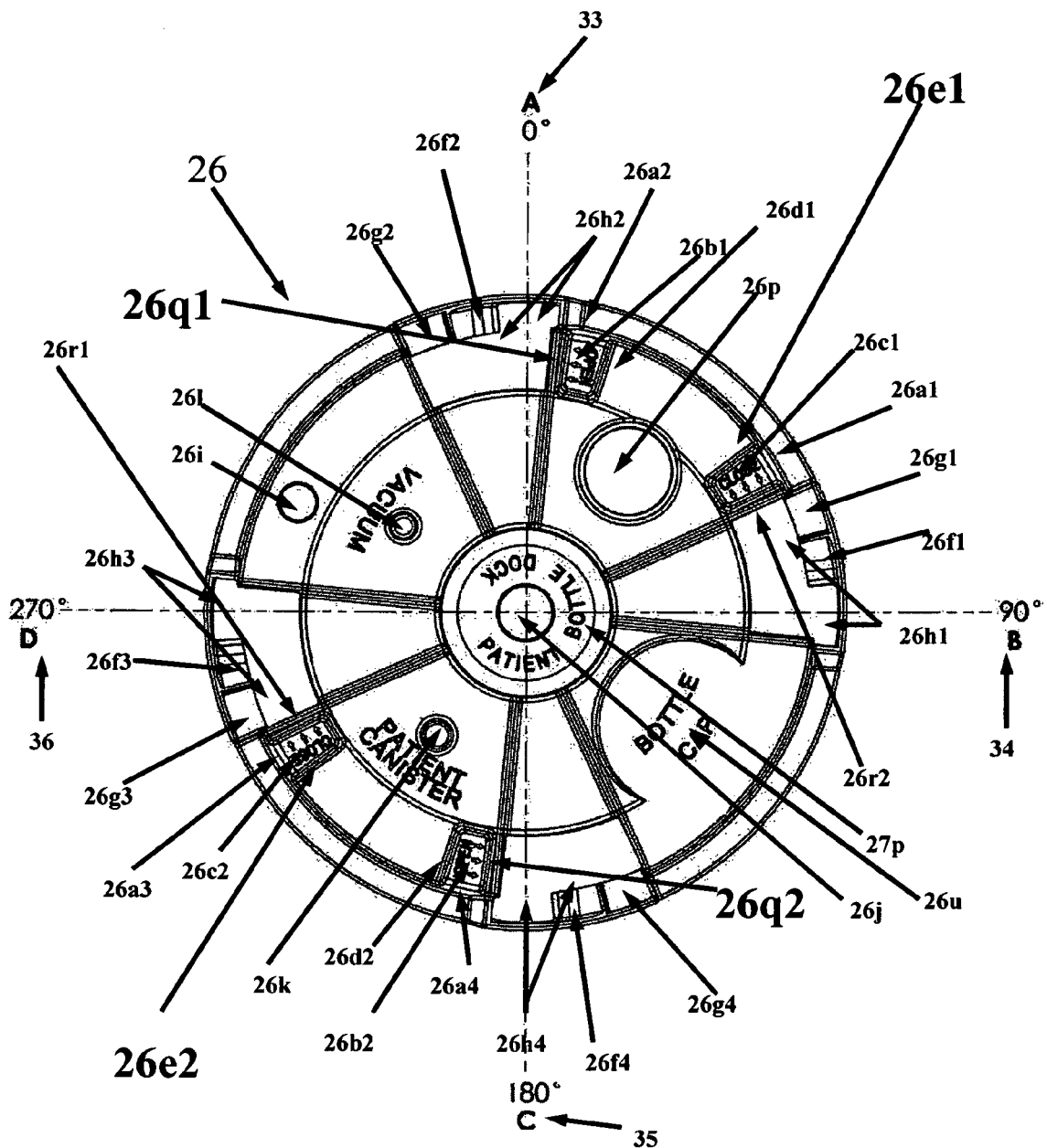
FIG. 21 is a top plan view of lid 26.

Turning to FIG. 21. FIG. 21 is a top plan view of lid 26. FIG. 21 shows coordinates 33 A at 0, 34 B at 90, 35 c at 180 and 36 and D at 270 forming a x-y coordinate plane with cross hairs intersecting the center of lid aperture hole 26j. Lid pillars are shown at 26a1, 2, 3, & 4. Lid locking hole is shown at 26i. Tubing connection port for a source of reduced pressure is shown at 26l. Suction tubing port 26k connection is disposed to draw waste material from a patient and/or source of waste to go into the canister when operating as a canister. The canister pour spout is located at 26p. Canister pillar apertures are shown at 26h1, 2, 3 & 4. Canister bottom sealing surface is shown at 26g1, 2, 3, 4. Canister pillar ascending ramp is shown at 26f1, 2, 3, & 4. Lid pillar indicia at 26c1, 26c2 show the indicia "CLOSED" with each pillar depicting three arrows showing the direction of motion/force in which pressure should be applied on lid pillar sides 26e1 and 26e2 in order to close and seal the lid and canister with respect to the respective pillars to move the pillar according to the indicia on top of the pillars. Indicia shown at 26b1 and 26b2 each depicting the indicia "OPEN" and each having the three arrows on each lid pillar depicting the sides 26d1 and 26d2 of lid pillars 26a2 and 26a4 showing which sides of the lid pillars 26a2 and 26a4 pressure should be applied to open and unseal the canister and lid. 27p shows the upwardly projecting lid boss making clearance for the bottle neck and plug. 26u shows the place on the lid where the bottle cap may be placed and retained by cap retaining ring 27g of capping member 27.

Turning to FIG. 22. FIG. 22 is a side elevation blow up cutaway of the circled portion of FIG. 23 which depicts the ascending canister pillar compression ramps 26f1, 2, 3, & 4. Also shown in this blowup of FIG. 22 is the canister pillar bottom sealing surface 26g1, 2, 3, & 4.

Turning to FIG. 23. FIG. 23 is a side elevation view of lid 26 with the cutaway of the lid ascending sealing ramp 26f1, 2, 3, & 4 and canister pillar bottom sealing surface 26g1, 2, 3, & 4. Also depicted are the annular outside lid skirt 26y marked in two places as well as the upwardly projecting bottle neck/plug 65 clearance boss 27p.

Turning to FIG. 24. FIG. 24 is a bottom plan view of lid 26. As depicted by this bottom plan view, an annular canister sealing surface 26o. Canister struts 26n1, 2, 3, 4, 5, 6, 7, & 8 can be seen in 8 places. Annular lid plug seal can be seen at 26x. Center lid aperture 26j for allowing connection access to plug (exemplary embodiments are shown if FIGS. 47-61) and patient suction tubing connection can be seen at 26j. The lid 26 annular skirt can be seen at 26y. 26s1, 2, 3, & 4 comprise rotational riding rails for each of the canister pillars 25b1, 2, 3, & 4 as the lid is located and placed on canister 25, lid 26 pillars 25b1, 2, 3, & 4 may be rotated contacting lid rails 26s1, 2, 3, & 4 until such relationship exists whereby the lid pillars are under lid pillars aperture spaces 26h1, 2, 3, & 4 whereby the lid drops down onto the canister as the lid pillars 25b1, 2, 3, & 4 pass thorough the lid pillar apertures 26h1, 2, 3 & 4. The canister pillars contact the lid rails and the canister pillars slidably engaged the lid rails and are in contacting engagement until the canister pillars then drop through lid aperture 26h1, 2, 3, & 4 to begin the counter rotational sealing action between lid 26 and canister 25. The upwardly projecting lid bottle neck clearance boss can be seen at 27p. 26l comprises the suction tubing connection port for the source of reduced pressure. Suction tubing connection port for the patient suction tubing (for the canister only mode of operation, e.g. not for a bottle docking mode of operation) can be seen at 26k. Lid lock hole can be seen at 26i. Hydrophobic filter press fit struts can be seen at 26m1, 2, & 3 to hold a hydrophobic filter in order to protect the reduced pressure tubing and negative pressure source system that draws negative pressure into the canister system through tubing connection port 26l. Also shown at a radius center point just inside the perimeter of upwardly projecting bottle neck/plug clearance boss 27p lid struts 26n1, 2, 3, 4, 5, 6, 7, & 8 take an upward projecting angle to act as a funnel guide, or a chamfer guide to create a precision seal fit between annular plug seal 26x and bottle plug, an example of which may be seen as 66i of plug 66 in FIG. 49.

Figure 25:
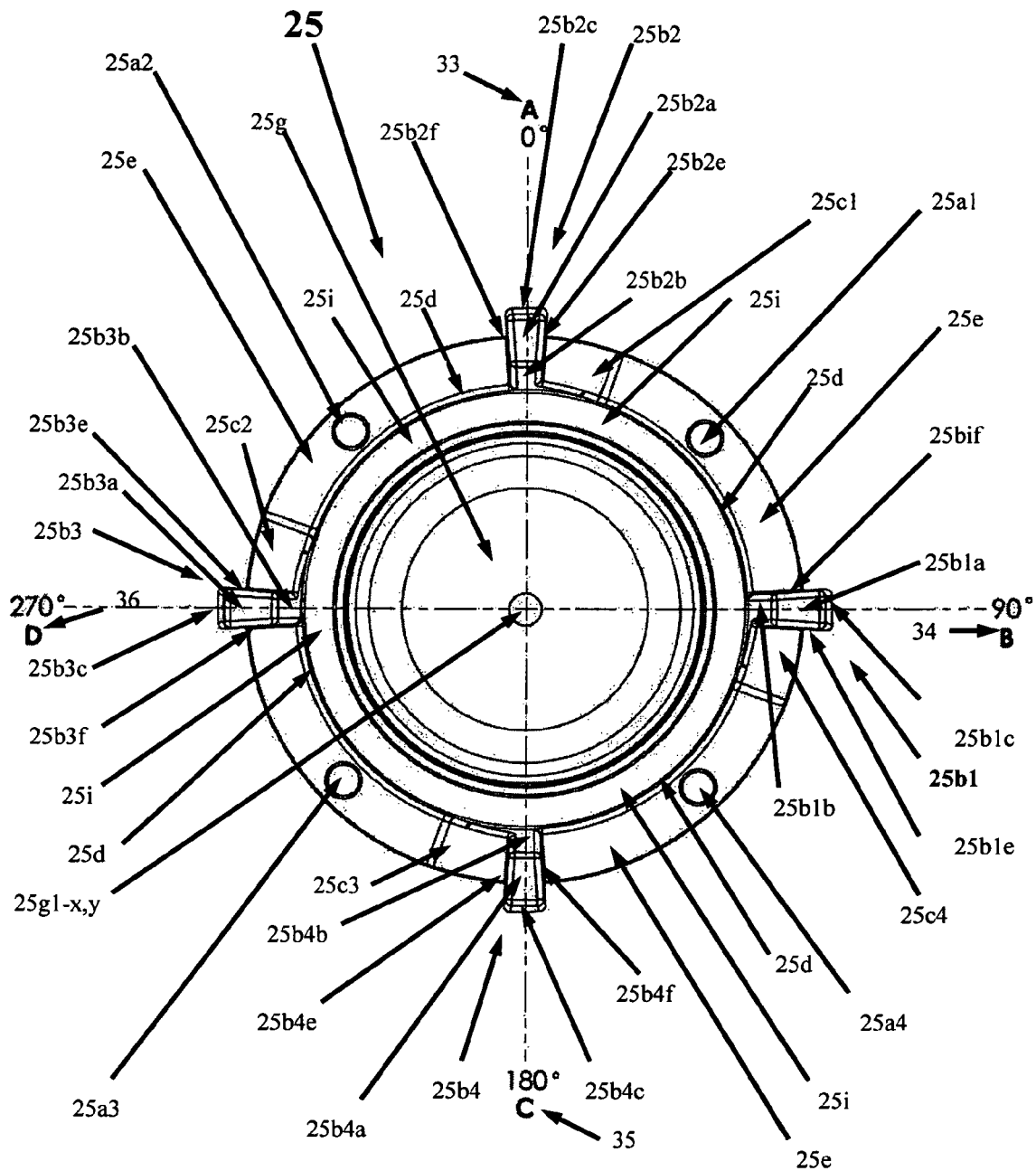
FIG. 25 is a top plan view of canister 25.

Turning to FIG. 25. FIG. 25 is a top plan view of canister 25. Canister pillars are shown at 25b1, 2, 3, & 4. Canister locking holes are shown at 25a1, 2, 3, & 4. Canister sealing surface is show at 25d in four places. An x,y coordinate plane is shown by 33 A at 0 degrees, 34 B at 90 degrees, 35 C at 180 degrees, and 36 D at 270 degrees. The lines a-c and d-b intersect at cross hairs in the center of canister 25 as shown by 25g1-x,y. The inside wall of canister 25 is marked at 25i in four places. Canister top sealing surface at 25e is shown in four places. The canister unsealing ramp is shown at 25c1, 2, 3, & 4. Canister pillar top is shown at 25b1a, 2a, 3a & 4a. It is the top of these canister pillars shown at the outside portion of 25b1a, 2a, 3a & b4a of canister pillars 25b1, 2, 3, & 4 that make slidably engagement contact with and ride on the composite annular sliding rails as shown in the lid bottom plan view of FIG. 24 at 26s1, 2, 3, & 4. The canister pillar inside angle is shown at 25b1b, b2b, b3b & b4b. Canister pillar outside angle is shown at 25b1c, 25b2c, 25b3c and 25b4c. Canister pillar side 25b1e, 25b2e, 25b3e and 25b4e are intended for force being applied thereon against canister pillar 25b1, b2, b3 and b34 in one direction. Canister pillar side 25b1f, 2f, 3f and 4f are intended to have force placed thereon in the opposite rotation. The inside bottom of canister 25 is shown at 25g.

Figure 26:
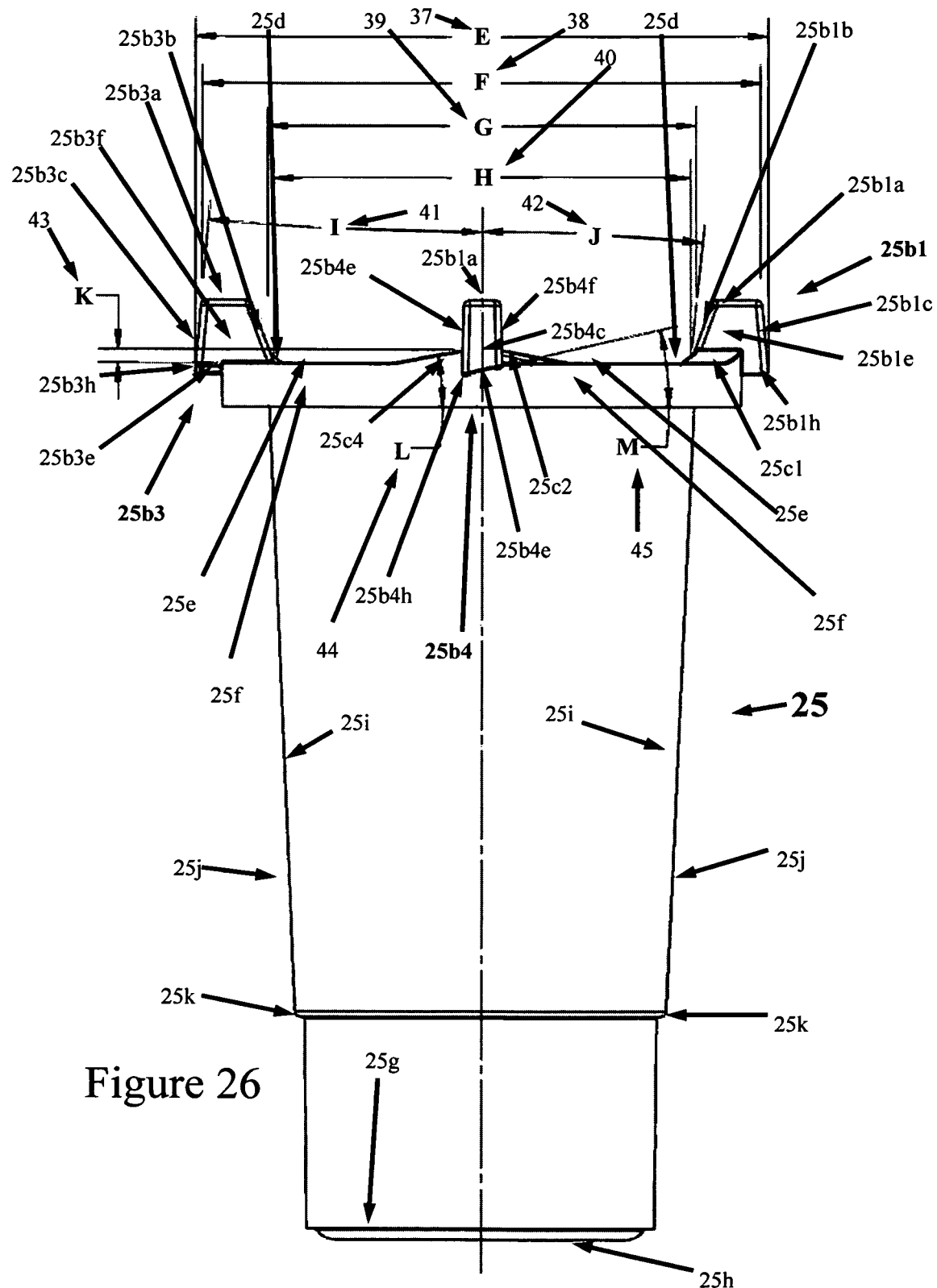
FIG. 26 is a side elevation view of canister 25.

Turning to FIG. 26. FIG. 26 is a side elevation view of canister 25. The outside bottom canister 25 is shown at 25h. The inside bottom of canister 25 is shown at 25g. The stacking separation ridge is shown at the outside of the canister at 25k at two places. The outside ascending wall of canister 25 is marked at 25j in two places. The inside ascending wall of canister 25 is marked at 25i in two places. The top sealing lid surface of canister 25 is marked at 25e in two places. The annular lid sealing surface of canister 25 is marked at 25d in two places. Canister pillars 25b1, 25b3 and 25b4 are shown. Canister pillar 25b2 is hidden behind canister 25b4. Canister pillar top is shown at 25b1a, 25b3a, 25b4a. Canister pillar top 25b2a is hidden behind canister pillar 25b4. Canister pillar inside angle 25b1b and 25b3b are marked in two places and are represented by canister pillar bottom compression ramp 25b4e and 25b3e and are marked in two places and are represented by angle M at 45. Canister pillar outside angle 25b1c and 25b3c and 25b4c are marked at three places and are represented at angle L at 41. Canister lid sealing surface 25d is shown as an annular top inside rim surface of the inside of canister 25 and is represented by angle J at 42. Canister pillar side pressure surfaces can be seen at 25b3f and 25b4f. Canister side pressure surfaces are shown at 25b1e and 25b4e. Lid unsealing, lowering and sealing registration ramp is shown at 25c1, 25c2 and 25c4 and are represented by angle L at 44. Lid unsealing, lowering and sealing registration ramp 25c3 is hidden on the back side of canister pillar 25b3. Canister pillar bottom lid contact sealing surface 25b1h, 25b3h and 25b4h can be seen at three places. Downwardly projecting annular canister skirt can be seen at 25f. The height of lid unsealing, lowering and sealing registration ramp is shown at 25b3h. The distance between the outermost lower portion of outside pillar angle of 25b1 and 25b3 can be seen as E at 37. The uppermost portion of the outside angle of canister pillar 25b1, 25b3 can be seen at F at 38. The lower portion of canister pillar inside angle of canister pillar 25b1 and 25b3 can be seen as G at 39. The diameter of annular lid sealing surface 25d of canister 25 can be seen as measurement H at 40.

Figure 27:
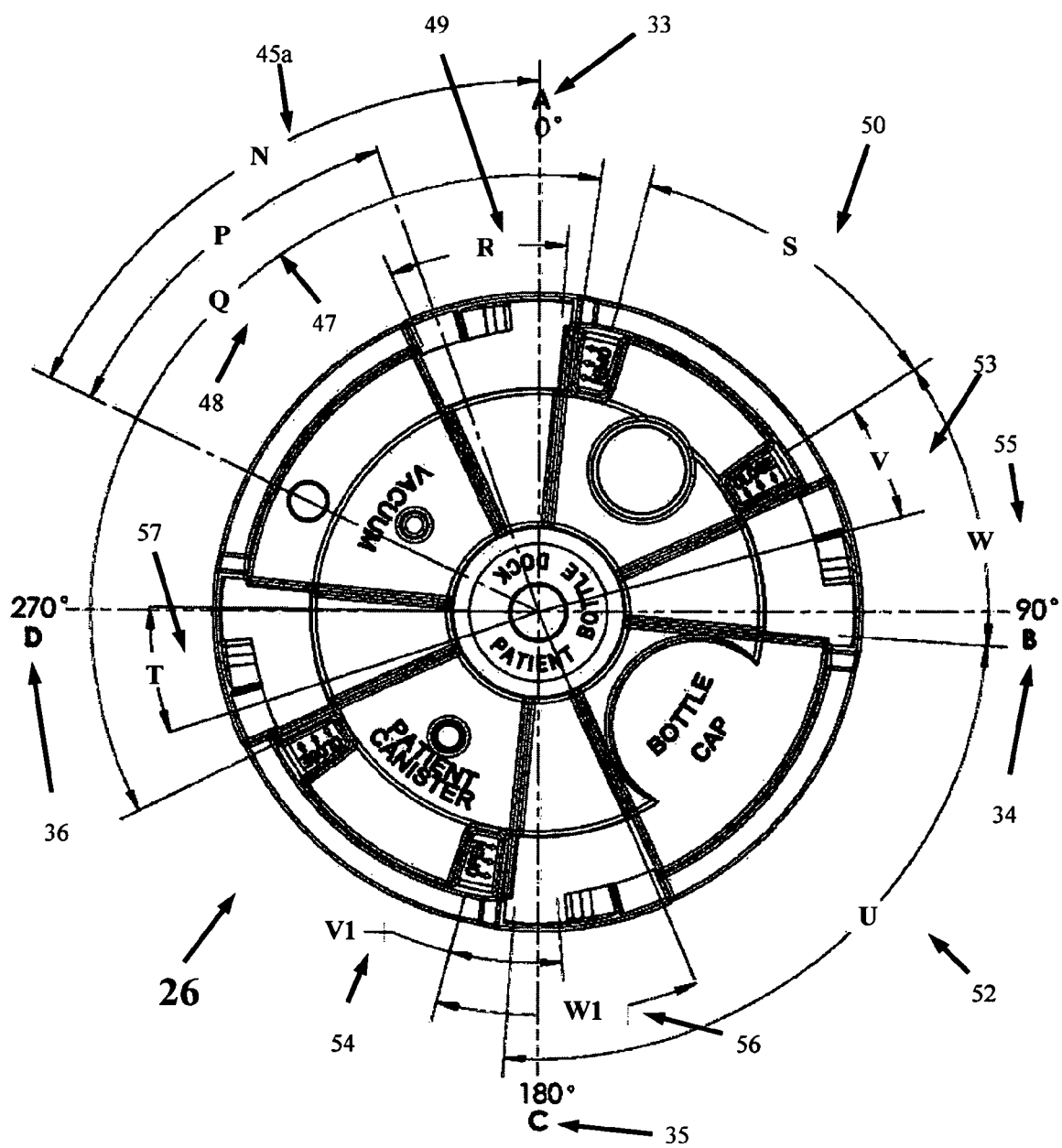
FIG. 27 is a top plan view of lid 26 showing the various features of lid 26 and where such features are arranged with respect to arcs and radians that may form a 360 degree circle. The spatial and temporal arrangements of lid 26 and canister 25 are operated by the sealing and unsealing of lid 26 and canister 25 based on the arrangements of said features.

Turning to FIG. 27. FIG. 27 is a top plan view of lid 26. It understood arcs of FIG. 27 may be in plurality with respect to lid 26. FIG. 27 shows an x,y coordinate plane system and A defines degrees shown at 33, B defines 90 degrees shown at 34, C defines 180 degrees shown at 35 and D defines 270 degrees shown at 36. S defines an arc shown at 50 which represents an arc that begins substantially at the center of lid pillar 26a1 and extends substantially to the center of lid pillar 26a2. Letter V defines an arc which is shown at 53 which represents an arc that begins substantially at the center of lid pillar 26a1 and extends substantially to the opposite end of canister pillar bottom seal surface 26g1. Letter W defines an arc shown at 55 which represents an arc beginning at one end of canister pillar pass through aperture 26h1 and extends substantially to the center of lid pillar 26a1. Letter U defines an arc shown at 52 which begins substantially at one end of canister pillar pass through aperture 26a and extends substantially to canister pillar aperture 26h4. The clockwise facing sides of 26h1 and 26h4 are shown. Letter W1 defines an arc shown at 56 which begins substantially at the center of lid pillar 26h4 and extends substantially at the end of the counterclockwise facing end of lid aperture 26h4. Letter V1 defines an arc beginning at one end of an intermediate portion of lid pillar 26b2 and extends substantially to the other end of the counterclockwise facing end of ascending lid ramp 26f4. Letter R defines and arc shown at 49 which begins substantially at the clockwise facing side of canister pillar aperture 26h2 and extends substantially to the counterclockwise facing side of canister pillar aperture 26h2. Letter N defines an arc shown at 45a beginning at the center of lid locking hole 26i and extends substantially to letter a-zero degrees shown at 33. Letter P defines an arc shown at 47 which begins substantially at the center of lid lock hole 26i and extends substantially to an intermediate point along lid pillar bottom sealing surface 26g2. Letter Q defines an arc shown at 48 which begins substantially at the center of lid lock hole 26i and extends substantially to counterclockwise facing surface lid pillar side 26q1. Letter T defines an arc shown at 57 begins substantially at D 270 degrees shown at 36 and extends substantially along an intermediate portion of the surface of lid pillar bottom sealing surface 26g3.

Figure 28:
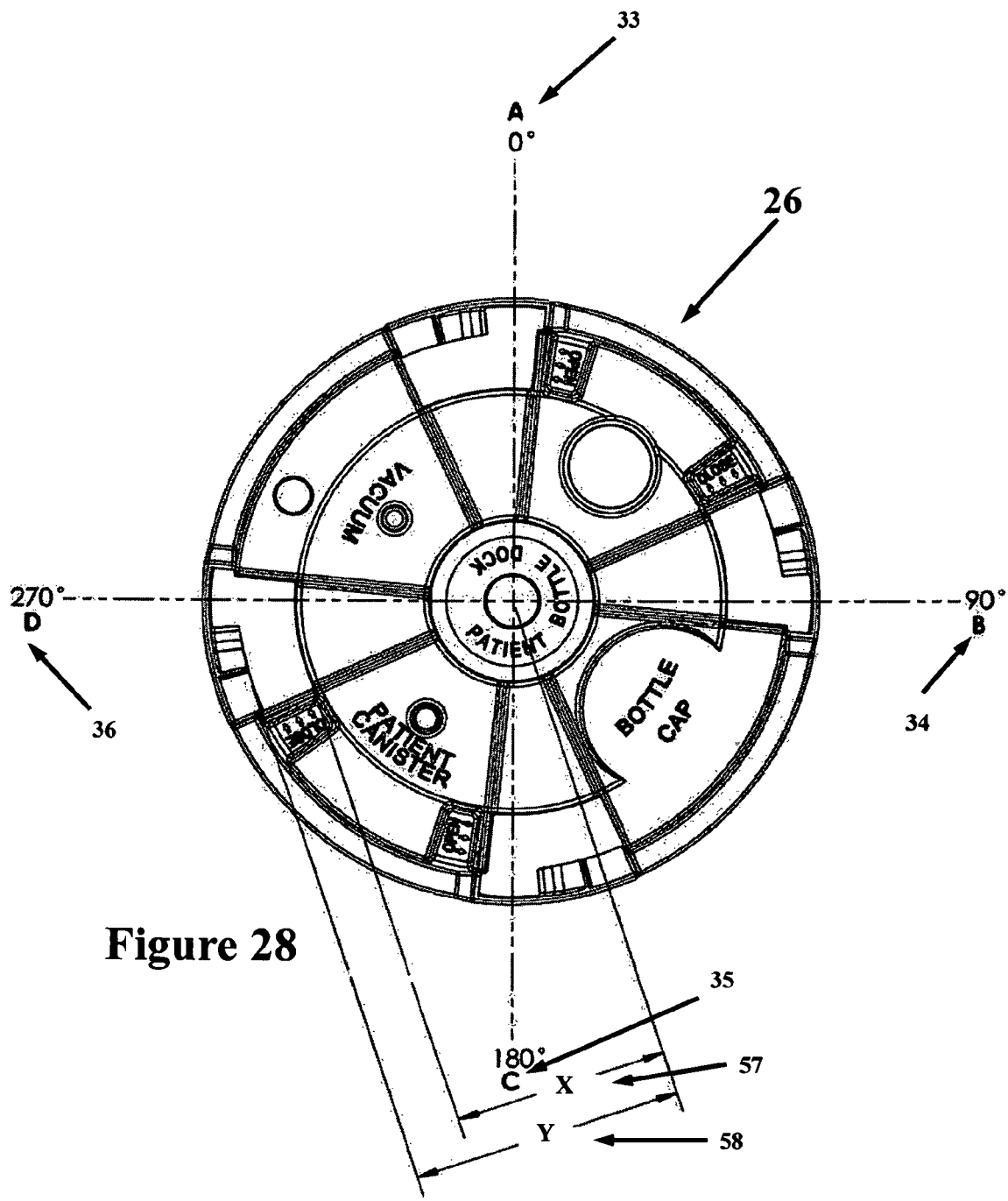
FIG. 28 is a top plan view of lid 26 showing the locations of lid pillars which define moment lever distances relative to other features of lid 26 and canister 25.

Turning to FIG. 28. FIG. 28 is a top plan view of lid 26. Letter Y is shown at 58 which defines a dimension beginning at the cross hairs where line AC and line BD are shown crossing substantially at the center of lid aperture 26j and extends substantially to the outside surface of lid pillar 26a1, 26a2, 26a3 and 26a4. Letter X shown at 57 defines a dimension beginning at the cross hairs where line AC and line BD cross substantially at the center of lid aperture 26j and extends substantially to the inside facing surface lid pillars 25a1, 25a2, 25a3 and 25a4. It is understood that arcs of FIG. 28 may be in plurality with respect to lid 26.

Figure 29:
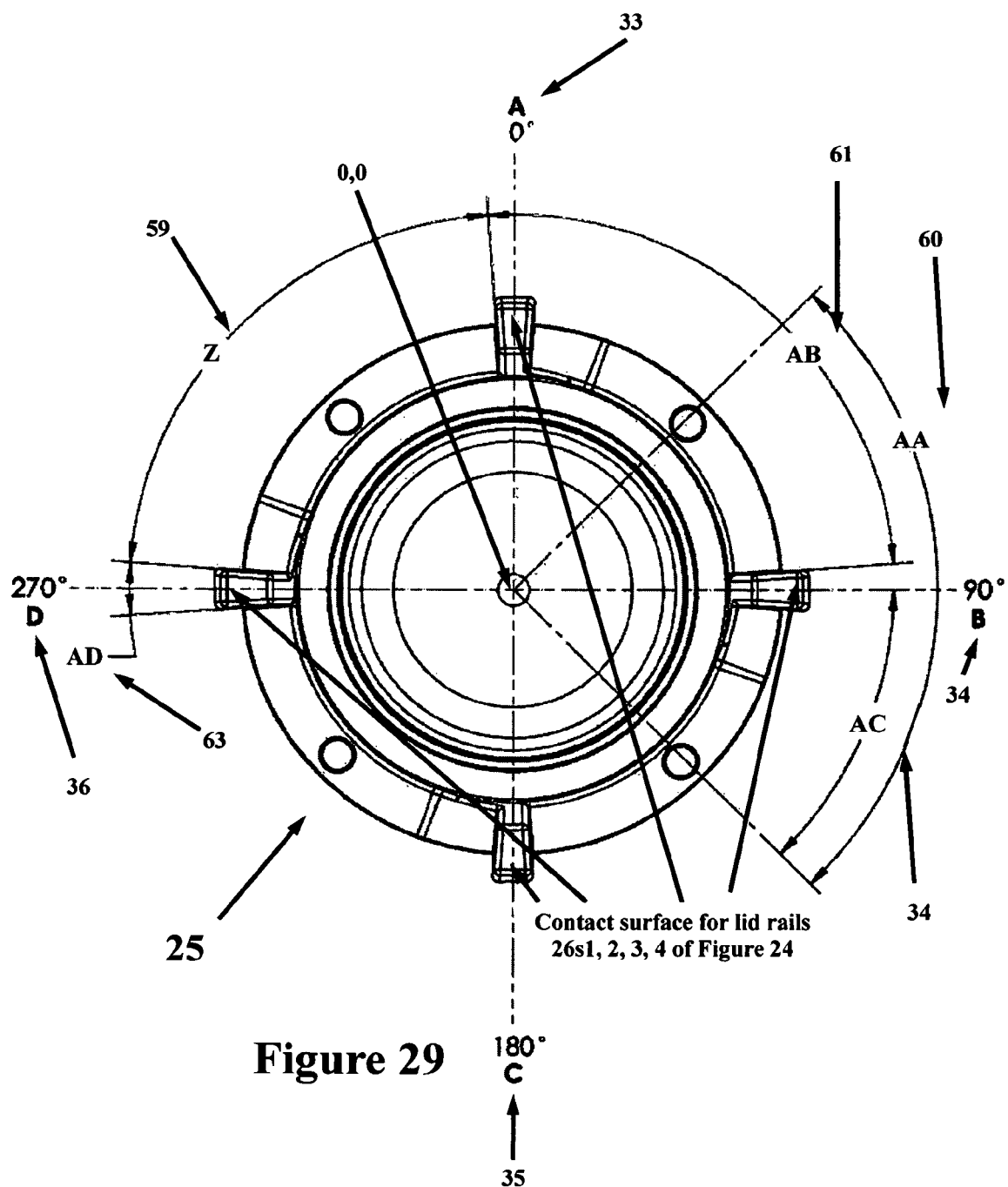
FIG. 29 is a top plan view of canister 25 showing radiuses and arcs of various features of canister 25 depicting the structural arrangements of canister 25 features that interface with lid 26. Said features operate to form a seal between lid 26 and canister 25. During the bottle docking mode of operation, said features also operate to form a seal between a bottle, a bottle plug 65 (as examples may be seen in FIGS. 47-61) and lid 26.

Turning to FIG. 29. FIG. 29 is a top plan view of canister 25. It is understood that arcs of FIG. 29 may be in plurality with respect to canister 25. Letter A references zero degrees shown at 33. Letter B references 90 degrees shown at 34. Letter C references 180 degrees shown at 35. Letter D references 270 degrees shown at 36. O,O reference the x,y coordinate plan defining the cross hairs where line AC and line BD cross located substantially at the center of canister 25. Letters AB defines an arc shown at 61 which begins substantially at the center of canister lock hole 25a1 and extends substantially to clockwise facing side of canister pillar 25b1f of canister pillar 25b1 of canister 25. Letters AA shown at 60 defines an arc shown at 69 which begins substantially at the center of canister lid lock hole and extends substantially to the center of an adjacent canister lid lock hole. Letters AC defines an arc shown at 34 and begins substantially passing through the center of canister pillar 25b1 and extends substantially to the center of canister lid lock hole 25a4. Letter Z defines an arc shown at 59 and begins substantially at the clockwise facing side of canister pillar 25b2f and extends substantially to the counterclockwise facing side of canister pillar 25b3e of canister pillar 25b3 of canister 25. Letters AD defines an arc shown at 63 which begins substantially at the counterclockwise facing side of canister pillar 25b3e and extends substantially at the clockwise facing side of 25b3f of canister pillar 25b3 of canister 25. It is understood that the features shown associated with the values of the distances, angles, arcs and radians of FIGS. 26, 27, 28 & 29 may be modified without departing from the scope of the attached claims.

Figure 30:
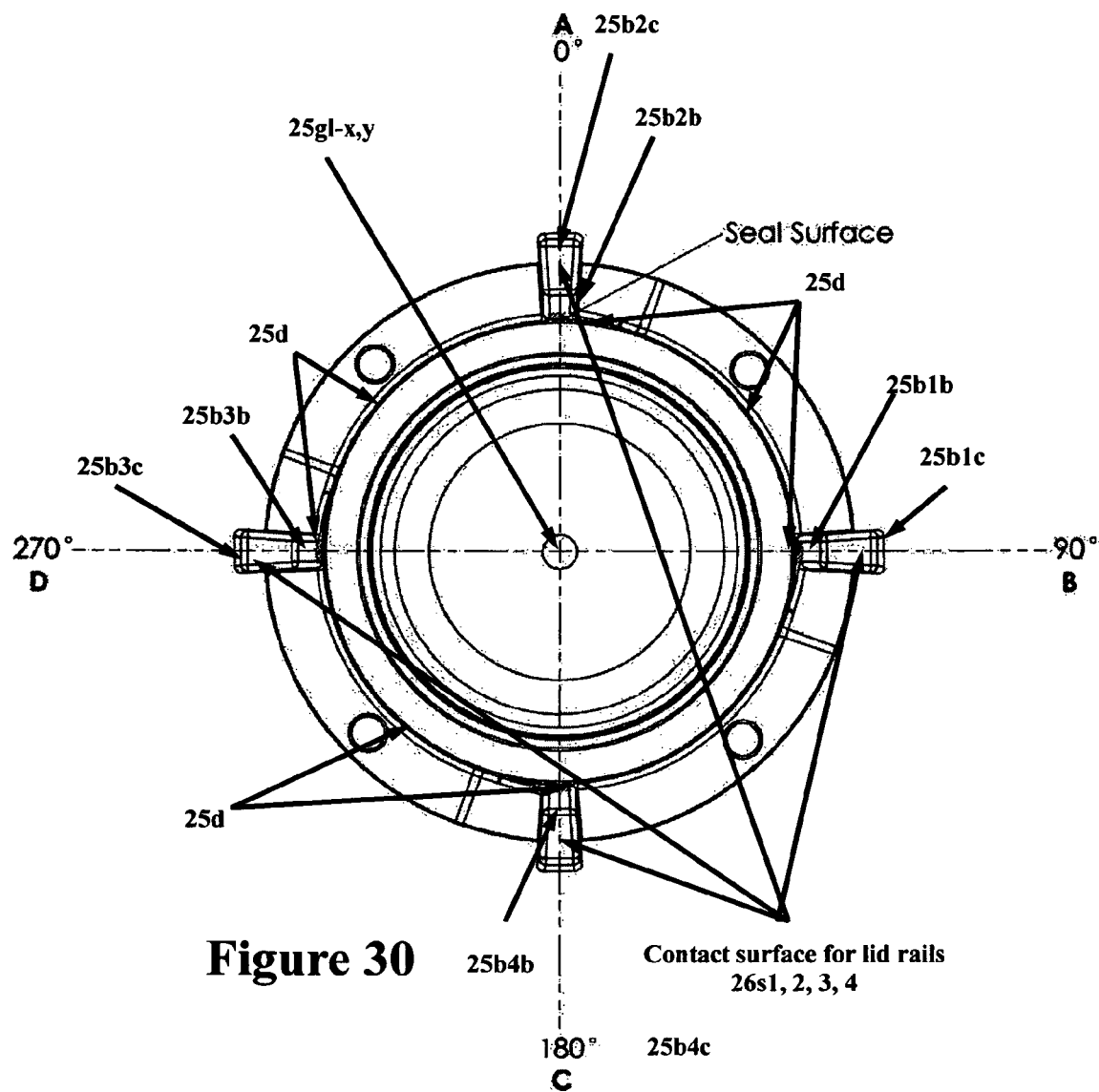
FIG. 30 is a top plan view of canister 25 showing structural arrangement of features of canister 25 which interface for the formation of seals between lid 26 and canister 25. During the bottle docking mode of operation, the said features of canister 25 also operate to form seals between a bottle, a bottle plug 65 (as examples may be seen in FIGS. 47-61) and lid 26 and lid 26.

Turning to FIG. 30. FIG. 30 is a top plan view of canister 25 and depicts annular sealing surface 25d marked by seven arrows and how the lid sealing surface 25d annularly relates to the center of canister 25 as shown at 25g1-x,y in so far as an x,y coordinate plane line AC crosses line BD at substantially the center of canister 25. This view also depicts how the inside angle of canister pillars 25b1b, 25b2b, 25b3b and 25b4b may function as a chamfer guide for guiding lid 26 and the inside edge of lid apertures 26h1, 26h2, 26h3 and 26h4 to assist registration of lid 26 and canister 25 to properly seal canister sealing surface 25d with lid seal 26o. In addition canister pillar outside surface angle 25b1c, 25b2c, 25b3c and 25b4c of canister pillars 25b1, 25b2, 25b3 and 25b4 also function as outwardly facing chamfer guides to assist with registration of lid 26 and canister 25 whereas the said outwardly facing chamfer guides interface with the outside edges of lid apertures 26h1, 26h2, 26h3 and 26h4 to guide and register lid 26 and canister 25. It is also contemplated that canister seal 25d and lid seal 26o are properly registered and aligned for sealing. Both horizontal and vertical registration between lid 26 and canister 25 are assisted so that alignment and sealing of lid seal 26o of lid 26 and canister seal 25d of canister 25 are engaged in such smooth alignment and registration.

Turning to FIG. 31. FIG. 31 is a side elevation blow up cutaway view of the top plan view of the assembly of lid 26 and canister 25 along the cutaway arrows shown at the left of FIG. 31, to depict the manner in which locking cap 27a may reside within lid 26 through lid lock hole 26i to contact canister 25. In this view the rotational relationship between lid 26 and canister 25 is such that lid lock hole 26i is not centered over canister lock holes 25a1, 2, 3, or 4. This structuration occurs while canister 25 and lid 26 are not in a fully sealed and operational relationship.

Turning to FIG. 32. FIG. 32 is a side elevation blow up cutaway view of the top plan view of the assembly of lid 26 and canister 25 along the cutaway arrows shown at the left of FIG. 32 whereby the rotational relationship between lid 26 and canister 25 is in a fully sealed position which aligns lid lock hole 26i with at least one of the four canister lid lock holes 25a1, 2, 3, or 4 such that lid lock cap 27a may be directed downwardly through the centered holes in that lid 26 and canister 25 may be rotationally locked by interference of cap 27a.

Turning to FIG. 33. FIG. 33 is a side elevation blow up view of the top plan view of the assembly of lid 26 and canister 25 along the cutaway arrows shown to the left of FIG. 33 which is the same disclosure as FIG. 32 with the modification that cap 27a is shown pressed down through lid lock hole 26i and at least one of canister lid lock holes 25a1, 2, 3 or 4. This rotationally stabilizes lid 26 and canister 25 by interference with cap 27a extending through holes in lid 26 and canister 25.

Figure 34:
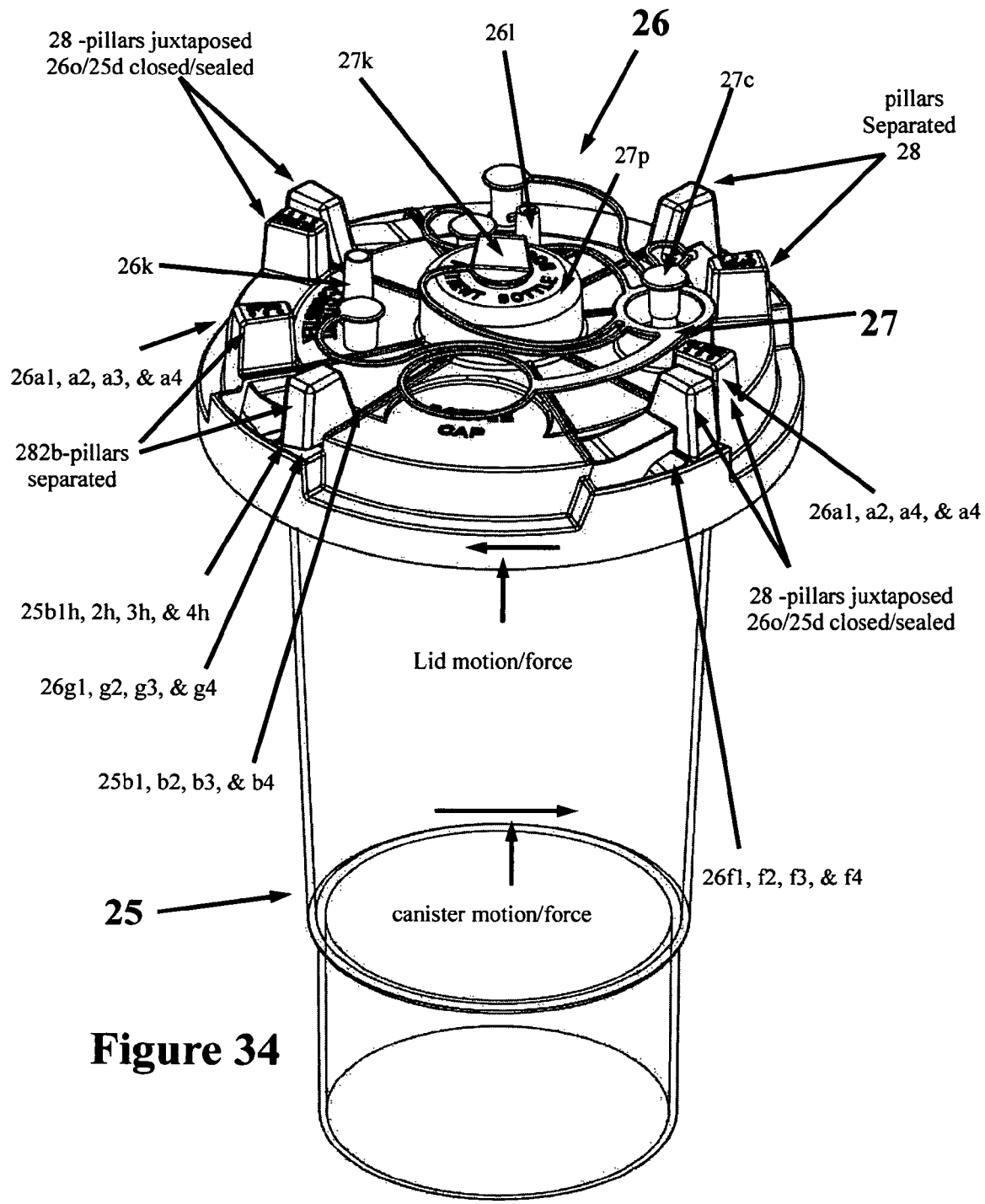
FIG. 34 is a top isometric view of a suction canister assembly of canister 25, lid 26 and member 27 in the mode of operation where bottle docking is not taking place because, for example a bottle is not available for docking. Lid port 26k is uncapped and open for connection to a patient suction tubing. Lid port 26l is uncapped and open and is available for connection to a conduit that is connected to a source of negative pressure. Lid port 26j is covered shown by member 27k. In this configuration, the suction canister system is in structuration of functioning as a non bottle docking system. The system is in a condition to draw waste under reduced pressure through a conduit and into the system as shown in FIG. 34. Also member 27b of capping member as shown in FIG. 18 is also shown plugging pour spout 26p of lid 26.

Turning to FIG. 34. FIG. 34 is a top isometric view of the non-bottle docking mode of the assembly of canister 25, lid 26 and cap member 27 in a sealed structuration. Canister 25 of this Figure is shown without a bottle docking capability whereas one feature of the system is that system of the instant case operates a both a normal waste collection canister system when no bottles are desired to be docked and also operates as a waste collection bottle docking system. This system is functional as both a normal suction canister system and a bottle docking system. The canister in FIG. 34 remains useful in a facility in the event that the facility does not have an inventory of bottles for transformation into waste ingressing collection receptacles within the canister systems as shown in the instant case, which bottles are shown docked in the embodiments of the instant case showing bottle docking capability. FIG. 34 shows at 28 depicted in a plurality of places, lid pillars and canister pillars are shown separated as depicted in two places and also in two places lid pillars and canister pillars are juxtaposed in two places to provide such that lid seal 26o and canister seal 25d are properly aligned, registered and sealed. Also shown are directional arrows depicting the clockwise motion potential of lid 26 and the counterclockwise motion potential of canister 25. The operation of sealing annular lid seal 26o with annular canister seal 25d is the operation of simply squeezing the lid pillars and canister pillars. The canister pillars and lid pillars are intended to be squeezed to seal lid 26 at 26o and canister 25 at 25d. An operator is to place lid 26 onto canister 25 and simply squeeze or pinch the corresponding lid pillars having indicia "CLOSED" on 26c1 and 26c2 together with the canister pillars located in the direction of the arrows defined by the indicia "CLOSED". Similarly, when in this structuration lid pillar surface tops 26b1, 26b2 show indicia "OPEN" and to unseal seals 26o and 25d the process of squeezing lid pillars 26a2 and 26b2 together with the canister pillars shown in the direction of the "OPEN" arrows on the surfaces of lid pillars 26b2 and 26a2. The operation of unsealing canister seal 25d from lid seal 26o is to squeeze together lid pillars and canister pillars shown as separated depicted by 28 marked twice in FIG. 34. The squeezing together of lid pillars and canister pillars as depicted twice as 28 cause the effect of canister pillar outside bottom surface 25bih, 25b2h, 25b3h and 25b4h to ascend upwardly with respect to lid 26 and to ride up the lid/canister compression and sealing ramp of 26f1, 26f2, 26f3 and 26f4 to the extent that 25b1h, 25b2h, 25b3h and 25b4h ride up to and onto the canister pillar sealing surfaces 26g1, 26g2, 26g3 and 26g4. The squeezing of pillars depicted at 28 causes the sealing between lid 26 at 26o and canister 25 at 25d. Also seen in FIG. 34 is the lid pillars 26a1, a2, a3 and a4 as well as canister pillars 25b1, b2, b3 and b4. Also shown in this view at 26k is a suction tubing connection port for the connection of a patient suction wand and or a suction tip as defined in the instant case for the purposes of drawing waste material into canister 25 under reduced pressure, but not limited to that. Also shown in this view is a vacuum tubing connection port 26l for the connection to a source of reduced pressure. A conduit connects the canister system to a source of waste material. It is understood that for example, pillars 26a1 and 25b1 are opposite pillars 26a3 and 25b3 and each of these pairs of pillars may be squeezed by one hand singularly to operate the system or they may be both squeezed simultaneously by two hands to operate the canister system. The same exists for the other opposing pillars. Pillars 26a2 and 25b2 are opposite pillars 26a4 and 25b4 and each of these pairs of pillars may be squeezed together by one hand singularly to operate the system or they may be both squeezed together simultaneously to operate the system. The forces required to operate the system may be confined to the offsetting counter rotational forces and do not operate to move the entire system. This is important whereas canister systems are often on wheels, or on IV poles which are on wheels, or are mounted on other non stationary equipment which is on wheels, or other moving and non stationary base support substrates and the counter opposing forces directed rotationally between the lid 26 and the canister 25 are designed offset and neutralize laterally directed forces which may move the substrate holding devices. The instant case embodiments are designed to the extent that the counterclockwise and clockwise forces used to operate the systems of the instant case reduce unwanted laterally generated forces when lid 26 and canister 25 are properly operated. This keeps the canister system and whatever holds the canister system within a desired footprint spatially within in the environment for which it is used. The design of the instant case also prevents the undesired rotation of the entire system as a result of the counter forces placed on the lid and canister pillars simultaneously. Also shown in this view are how capping member 27k caps and seals the lid 26 center aperture 26j whereas there is no bottle to be docked in this embodiment whereas the tubing connector of bottle plug (examples of plugs may be seen in FIGS. 467-61) not shown is not necessarily to be activated in this scenario because there no bottle being docked in this embodiment scenario of FIG. 34. FIG. 34 shows the systems of the instant case being employed as a non-bottle docking canister system yet embodying novel operating and system sealing features.

Figure 35:
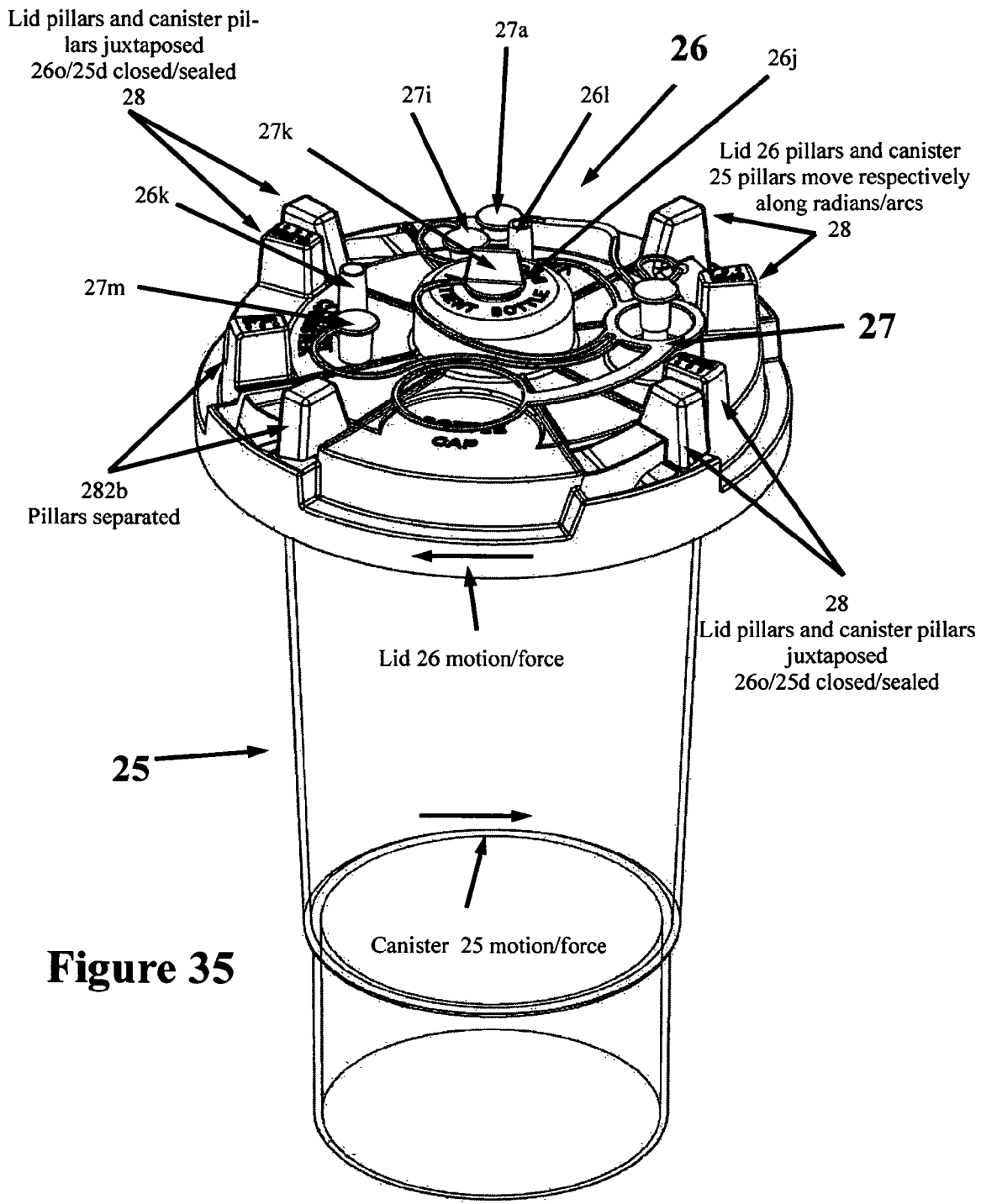
FIG. 35 is a top isometric view of FIG. 34 with locking member 27a pressed down locking the canister 25 and lid 26 into rotational security as shown in FIG. 33. This is accomplished by alignment of lid lock hole 26i of lid 26 and one of canister 25 lid locking holes 25a1, 2, 3, & 4 as shown in FIG. 33.

Turning to FIG. 35. FIG. 35 is a top isometric view which is similar to FIG. 34 except that locking cap member 27a is pressed down through lid lock hole 26i of lid 26 and canister locking hole 25a1, a2, a3 and or a4 of canister 25 as depicted in FIG. 33.

Figure 36:
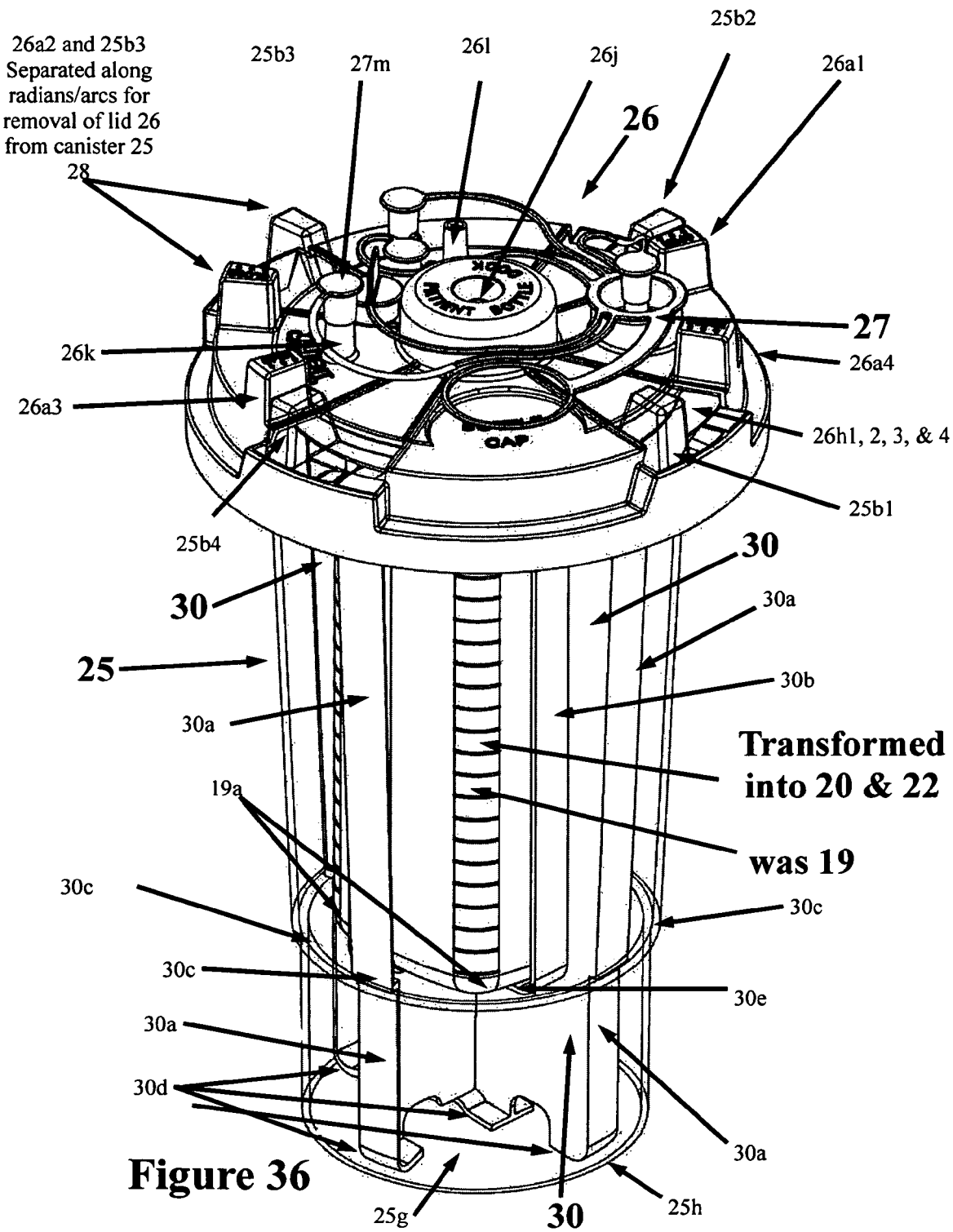
FIG. 36 is a top isometric view of the bottle docking mode of operation whereby bottle 19 is disposed in canister 25. Bottle 19 is supported by a stand 30. Bottle neck retains a plug 65 (exemplary plug embodiments may be seen in FIGS. 47-61).

Turning to FIG. 36. FIG. 36 is a top isomeric view of bottle docking system showing canister 25, lid 26, capping member 27, with the transformed bottle 19 shown and depicted as bottle 19 may be transformed in 20 and 22 transformed into 20 and 22 as shown in FIGS. 13, 14 and 15. Bottle 20 is conditioned for transformation into a waste ingressing receptacle and ultimately will dispose of waste material in a condition as shown in FIG. 15 being re-capped and sealed for the transfer of waste. Also it is shown at 25b1, 25b2, 25b3 and 25b4 that these canister pillars of canister 25 are projecting upwardly through lid apertures 26h1, 26h2, 26h3 and 26h4 for the placement of lid 26 onto canister 25 for the application of the counter rotational forces on lid pillars and canister pillars to seal lid seal 26o with canister seal 25d and to seal lid seal 26x with bottle plug 65 (not shown) (examples of plugs maybe be seen in FIGS. 47-61). Also seen in FIG. 36 is bottle holder 30. Bottle holder 30 is shown with a bottle resting surface 30e, a first indicia surface 30b for showing markings that represent how much collected material has been ingressed into bottle 19 which has been conditioned and transformed in preparation to become 20 and 22. Bottle holder 30 also shows surface 30a which is the surface closer to inside wall of canister 25. Surface 30a of bottle holder 30 is a surface which may have indicia markings for showing how much collection material has been ingressed into both the bottle 22 and the canister 25. Also shown in FIG. 36 is bottle holder 30 having bottoms depicted at 30d which rest inside canister 25 on its bottom surface 25g. 30c shows the stepped portion of the upright standards of bottle holder 30 which are located at the same location of the stepped portions along the annular wall of canister 25. Also shown in FIG. 36 is bottle bottom 19a which rests on bottle holder at 30e. It is understood that as lid pillars and canister pillars are urged for the purposes of sealing the bottle docking system, and as the canister pillars ascend up the lid ramps resulting in compression of lid 26 and canister 25 together, there is also a compression of the components of the bottle docking system such that canister inside bottom 25g and lid holder bottom 30d move together causing compression between the two, and, bottle 20 and holder surface 30e are moved together causing compression between the two, plug 65 and bottle 20 are moved together causing compression between the two, and lid 26 and canister are moved together ultimately resulting in 1) sealing of canister 25 and lid 26, 2) sealing of lid 26 and bottle plug (not shown) 65 (examples of plugs may be seen in FIGS. 47-61), sealing of bottle 20 and plug 65 (not shown) (examples of plugs may be seen in FIG. 47-61). It is also noted that the height of lid ramps 26f1, 2, 3, & 4 is great enough so that all of the manufacturing stack up tolerances of the canister 25, lid 26, bottle 20 (in the conditioned and transformed assembly), and bottle holder 30, will all function to provide seals sufficient to contain and direct reduced pressure of a vacuum draw path such that collection material may be ingressed into bottle 20/21. Similarly, when unsealing the system for disassembly, the height of unsealing ramps 25c1, 25c2, 25c3 and 25c4 as shown in FIG. 26 are sufficient to unseal canister 25 and lid 26. FIG. 36 also shows 26a2 and 25b3 separated along radians/arcs for removal of lid 26 from canister 25.

Figure 37:
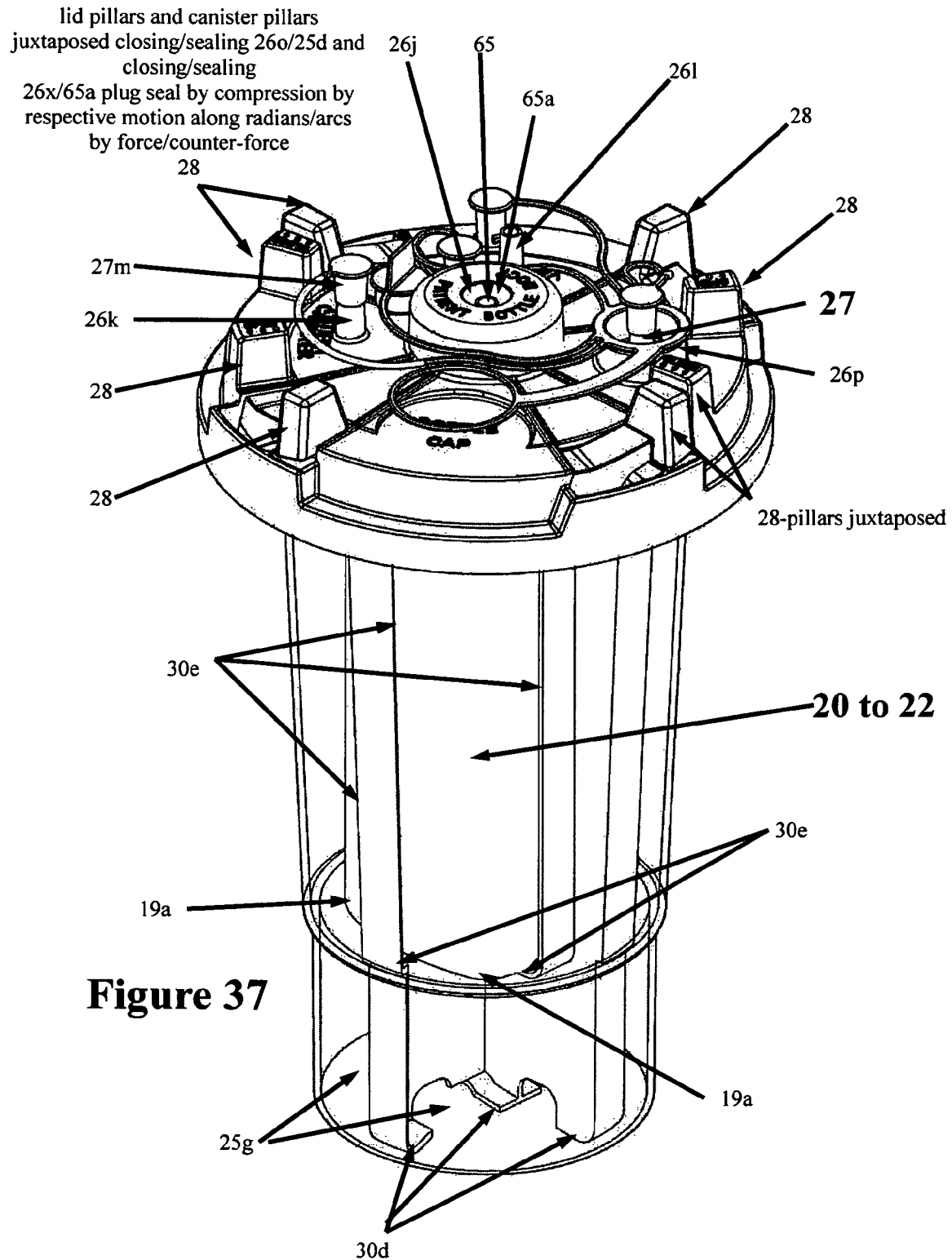
FIG. 37 is a top isometric view of the collection system in a bottle docking mode of operation.

Turning to FIG. 37. FIG. 37 is a top isometric view showing lid pillars ad canister pillars juxtaposed closing/sealing lid seal 26o with canister seal 25d and closing/sealing lid seal 26x with bottle plug seal 65 (not shown) (FIGS. 47-61). Compression of the plug 65 (FIGS. 47-61 provide examples of plugs), lid 26, canister 25, bottle 20, bottle holder 30 has been accomplished to the extent sufficient to contain reduced pressure and form a vacuum draw path which is capable of ingressing drawn waste material from a source of collection material into bottle 20 conditioning and transforming bottle 20 into a waste ingressing container. FIG. 37 also shows lid pillars and canister pillars juxtaposed closing/sealing 26o and 25d and closing and sealing 26x and 65a (not shown) (FIGS. 47-61) by compression by respective motion along radians/arcs by force counter-force. FIG. 37 also shows juxtaposed lid and canister pillars.

Figure 38:
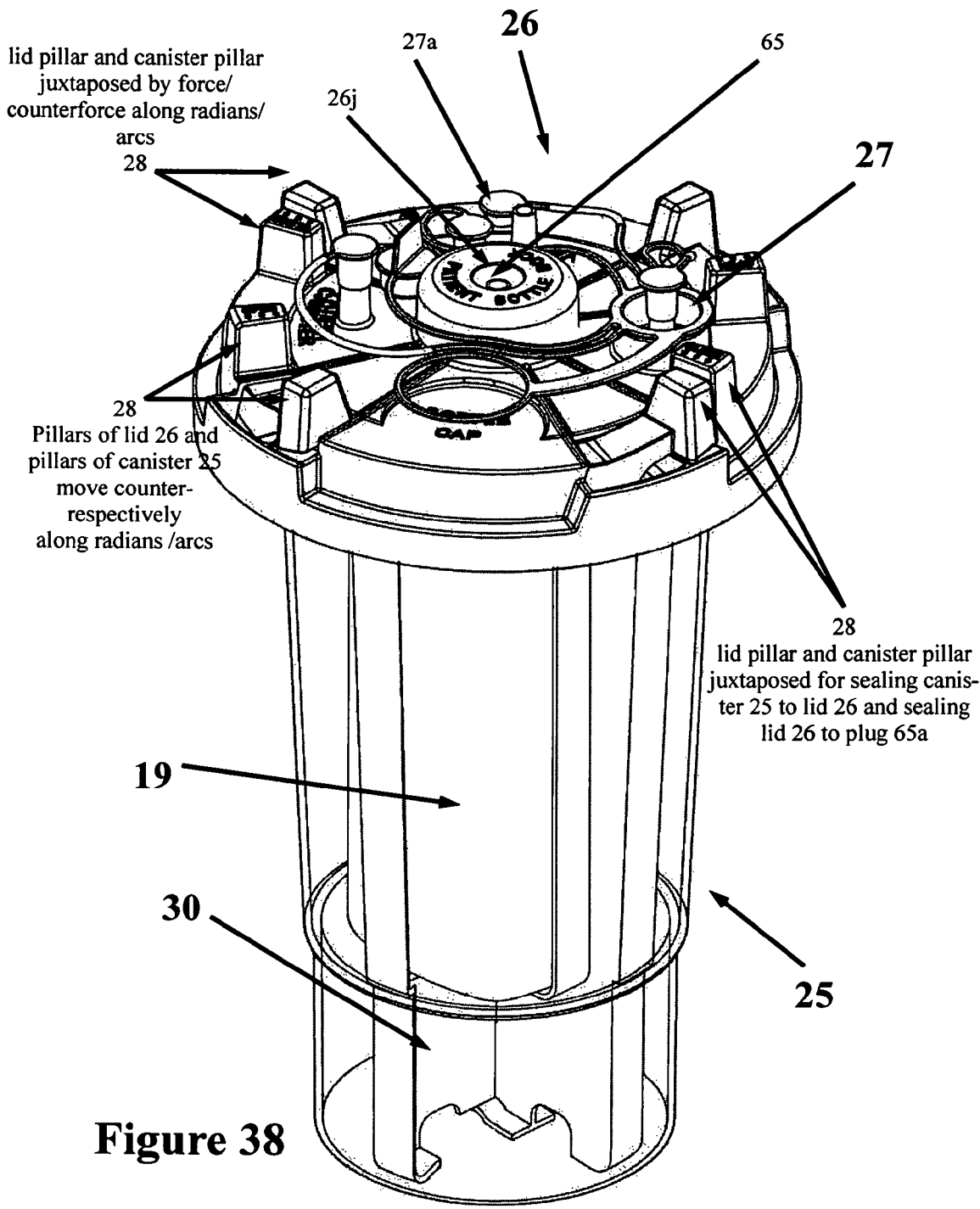
FIG. 38 is a top isometric view showing a bottle docking canister system wherein waste material has been drawn into bottle 19 as shown by number 21. Canister 25 and lid 26 are shown in a fully sealed and locked position.

Turning to FIG. 38. FIG. 38 is a top isometric view of a bottle docking embodiment system showing cap 27a pressed down in a locking rotational movement between canister 25 and lid 26. Also seen at 65 showing the plug suction tubing connection for creating a conduit flow control connection between a source of material to be collected and the ingressing of material to be drawn into bottle 20/22. FIG. 38 shows lid pillars and canister pillars juxtaposed by force/counter-force along radians/arcs. FIG. 38 also shows pillars of lid 26 and pillars of canister 25 move counter-respectively rotationally along radians/arcs. FIG. 38 also shows lid pillars and canister pillars juxtaposed for sealing canister 25 to lid 26 and sealing lid 26 to plug 65a (not shown)(examples of plugs may be seen in FIGS. 47-61).

Figure 39:
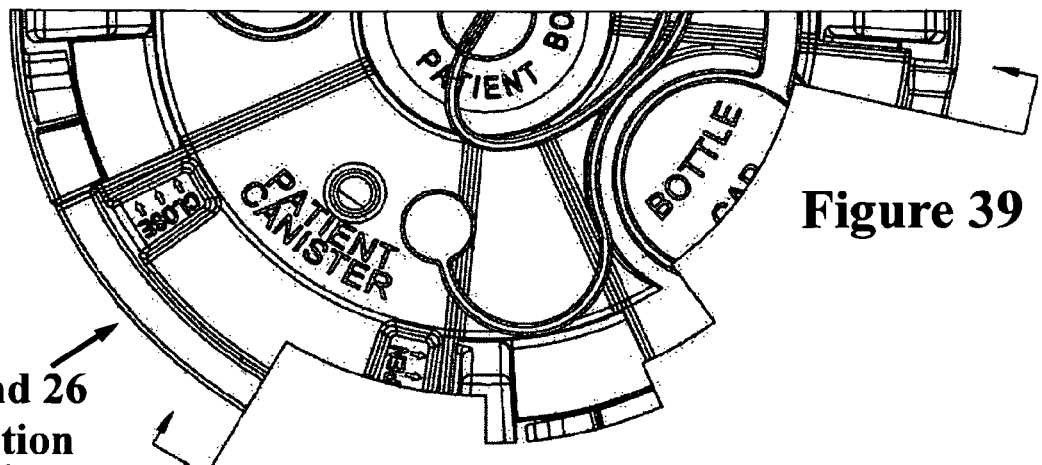
FIG. 39 is a top plan cutaway view of the sealing/closing assembly of lid 26 and canister 25 as depicted along the broken arrows.

Turning to FIG. 39. FIG. 39 is a top plan cutaway view along the arrows of lid 26 and canister 25 operating at a certain rotational orientation as depicted in FIG. 40.

Figure 40:
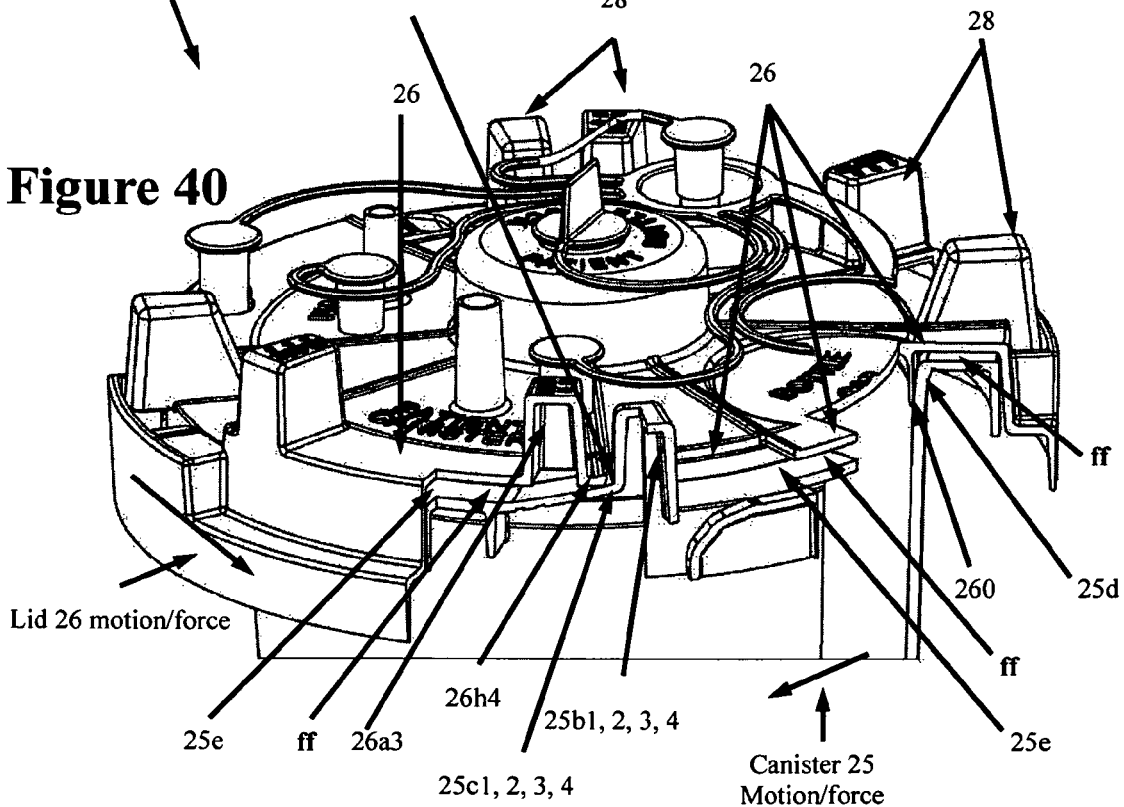
FIG. 40 is a top isometric cutaway view of FIG. 39 showing the relationship of canister 25 and lid 26 during its unsealing counter rotation. Canister 25 and lid 26 relationship 28 is marked in two places depicting the physical juxtaposition of the canister 25 and lid 26 pillar structuration, motion, and configurations.

Turning to FIG. 40. FIG. 40 is a top isometric view of the cutaway of canister 25 and lid 26 assembly of FIG. 39. Lid 26 motion force is shown in the counterclockwise direction. Canister 25 motion force is shown in the clockwise direction. ff defines a space/gap between lid 25 and canister 25 based on the rotational orientation between lid 26 and canister 25. Lid pillar 26a3 is shown rotationally abutted up against the counterclockwise facing side of canister pillar 25b3 and canister pillar 25b3 is abutted up against the clockwise facing edge of lid aperture 26h1 at 26e1. It is understood that lid 26 and canister 25 may be rotationally oriented in at least four separate initial orientation ranges leaving the orientations of lid 26 and canister 25 features available to be in up to four possible initial spatial rotational range arrangements. Also shown is lid aperture counterclockwise facing edges 26r1 and 26r2 have has been urged up canister ramps 25c1, 2, 3, and/or 4 to effect ramp height as seen in FIG. 26 for unsealing the vacuum draw path that has contained the reduced pressure forces. The orientation of lid 26 and canister 25 in FIG. 40 produces a gap between lid 26 and canister 25 as shown by ff. Also shown is the orientation of lid seal 26o and canister seal 25d. FIG. 40 also shows lid pillars and canister pillars counter rotationally urges along radians/arcs. FIG. 40 also shows lid pillars and canister pillars allowed to separate counter-rotationally along radians/arcs.

Figure 41:
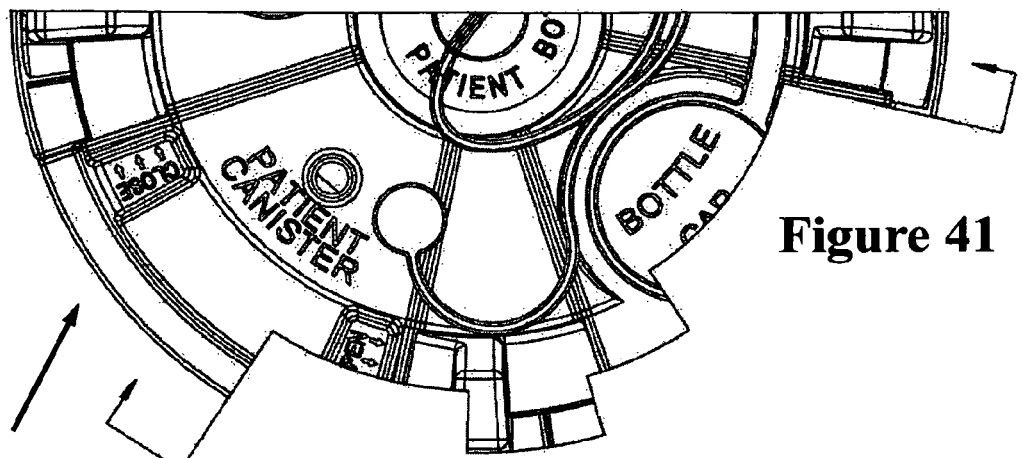
FIG. 41 is a top plan cutaway view of unsealing/opening of canister 25 and lid 26 as shown along the arrows.

Turning to FIG. 41. FIG. 41 is a top plan cutaway view along the arrows of lid 26 and canister 25 showing operation at certain rotational orientations respectively between lid 26 and canister 25 as depicted in FIG. 42.

Figure 42:
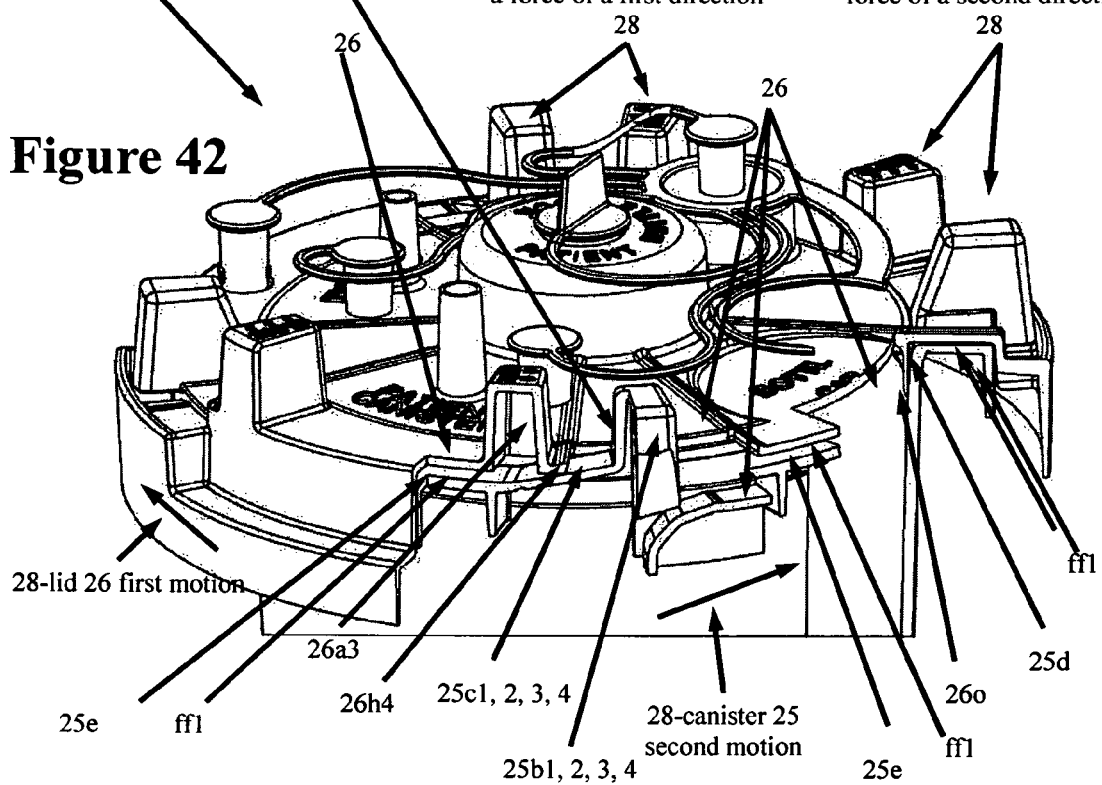
FIG. 42 is a top plan cutaway view of FIG. 41 showing the relationship of canister 25 and lid 26. The progression of the relationship between lid 26 and canister 25 are shown going in FIGS. 46, 44, 42 and 40 depicting going from the sealed mode to the unsealed mode of lid 26 and canister 25. The progression of the relationship between lid 26 and canister 25 is shown in the reverse process, e.g.

Turning to FIG. 42. FIG. 42 is a top isometric cutaway along the arrows shown in FIG. 41 depicting the orientation of lid 26 and canister 25. Lid 26 is shown moving in a clockwise orientation and canister 25 is shown respectively resisting such a clockwise motion. Space/gap ff1 is shown as smaller than space/gap ff of FIG. 40 whereas the rotational orientation between lid 26 and canister 25 shows counterclockwise facing lid aperture edge at the bottom of lid pillar surfaces 26q1 and 26q2 are located at an intermediate portion of canister ramps 25c1, 2, 3, and or 4. FIG. 42 shows lid pillars and canister pillars allowed to separate counter-rotationally along radians/arcs by a force of a first direction. FIG. 42 also shows lid pillars and canister pillars counter-rotationally urged closer along radians/arcs by a force of a second direction.

Figure 43:
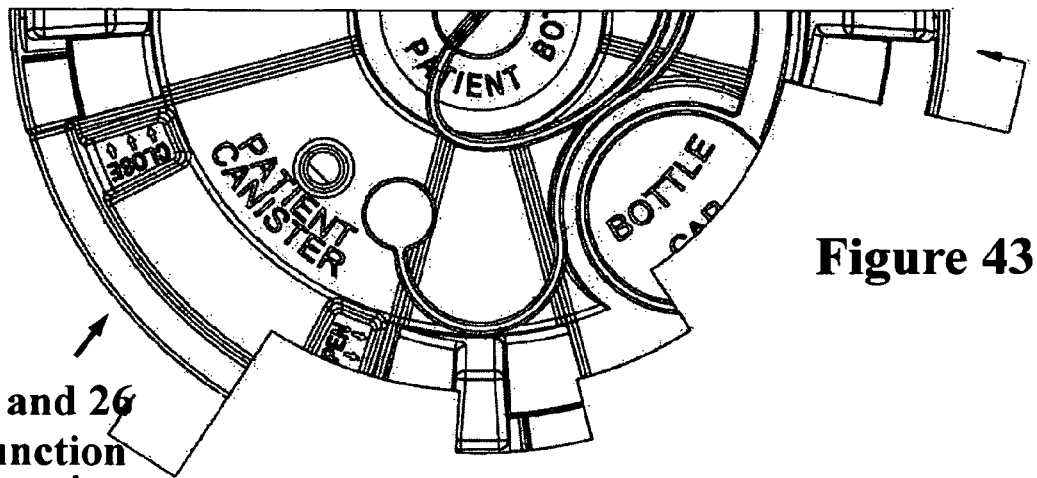
FIG. 43 is a top plan view of a cutaway of canister 25 and lid 26 as shown in FIG. 44 depicted by the arrows.

Turning to FIG. 43. FIG. 43 is a top plan cutaway view along the arrows of lid 26 and canister 25 showing operation at certain rotational orientation respectively between lid 26 and canister 25 as depicted in FIG. 44.

Figure 44:
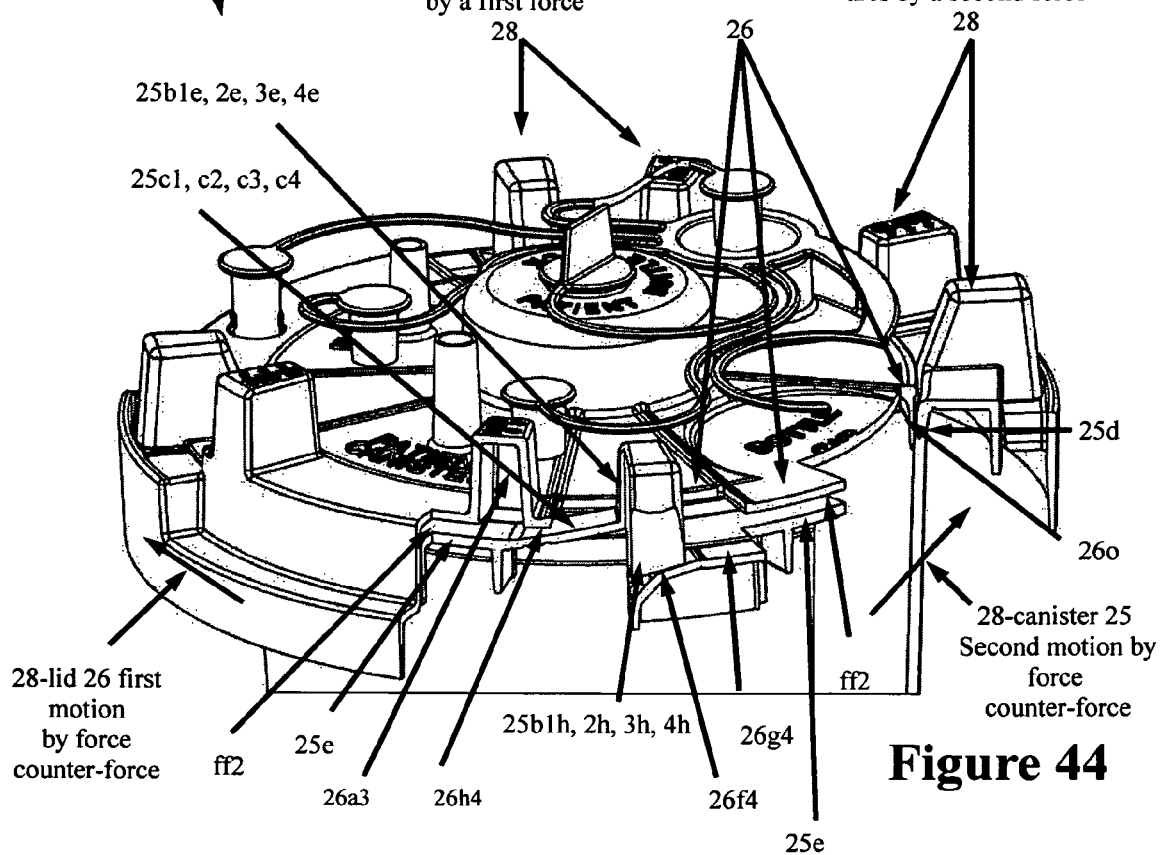

Turning to FIG. 44. FIG. 44 is a top isometric cutaway view of lid 26 and canister 25 operation as seen in FIG. 43. FIG. 44 shows space/gap ff2 being smaller than that of ff1 as shown in FIG. 42. Canister seal 25d and lid seal 26o are shown sealed to a greater extend that that shown in FIG. 42. The bottom of lid pillar surface 26q1 and 26q2 as may be seen in FIG. 21 which represent the counter clockwise facing edge of lid apertures 26h4, and 26h2 are seen further down the canister ramps 25c1, 25c2, 25c3 and or 25c4 than as shown in FIG. 42, depending upon which rotational orientation the lid 26 and canister 25 are oriented in with respect to each other. FIG. 44 also shows lid pillars ad canister pillars are allowed to separate counter-rotationally along radians/arcs by a first force. FIG. 44 also shows lid pillars and canister pillars counter-rotationally urges closer together along radians/arcs by a second force. FIG. 44 also shows lid 26 in first motion which is a motion opposed to a counter force. FIG. 44 also shows canister 25 in second motion which is a motion opposed to a separate counter force.

Figure 45:
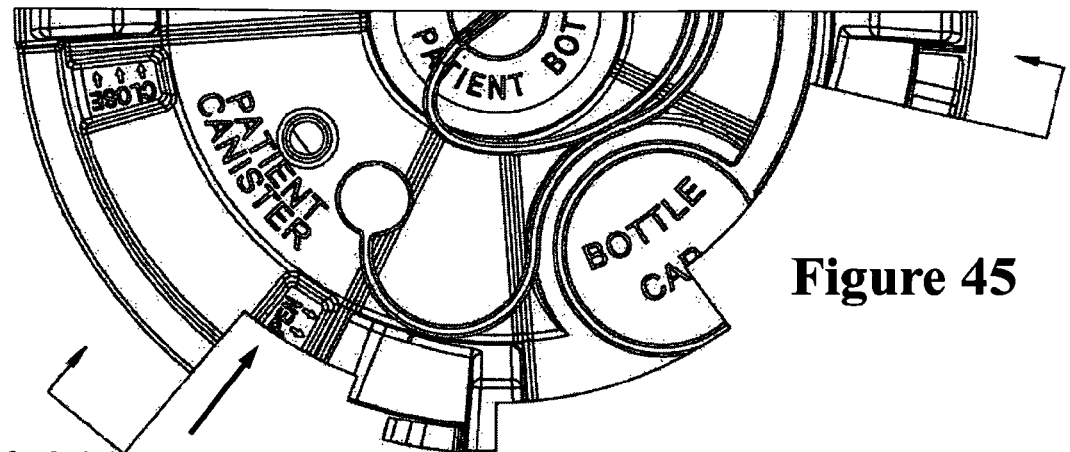
FIG. 45 is a top plan view of canister 25 and lid 26 relationship showing a cutaway of canister 25 and lid 26 along the arrows.

Turning to FIG. 45. FIG. 45 is a top plan cutaway view along the arrows of lid 26 and canister 25 showing operation of certain rotational orientation respectively between lid 26 and canister 25 as depicted in FIG. 46.

Figure 46:
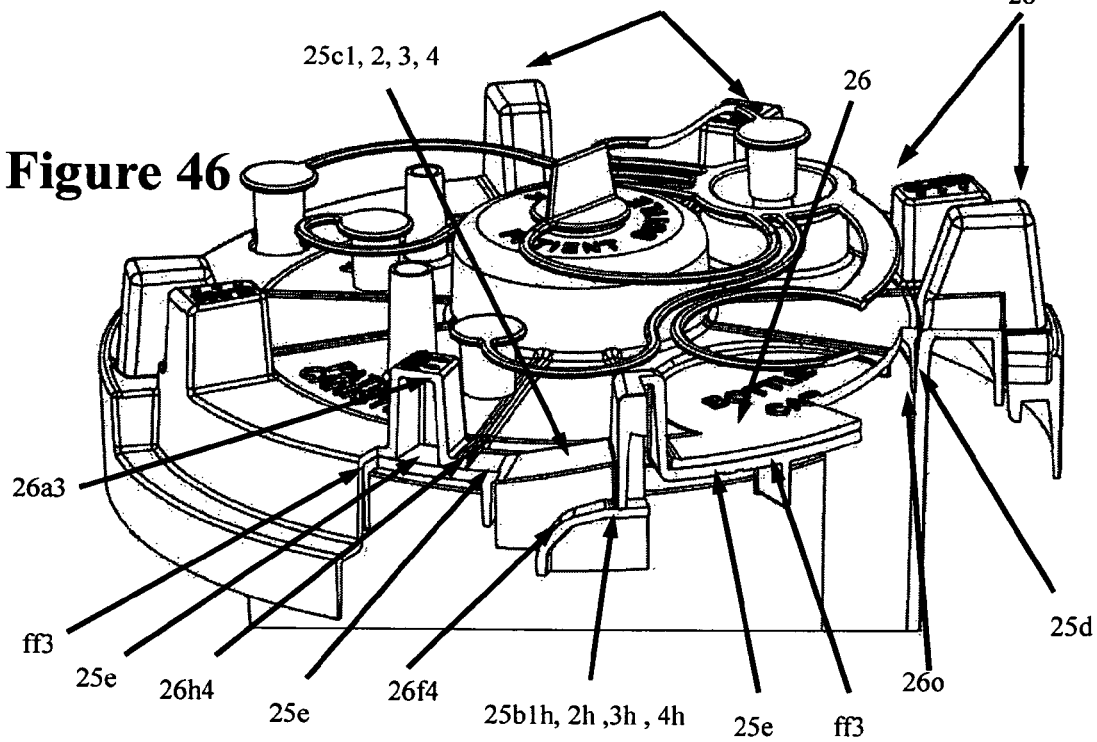

Turning to FIG. 46. FIG. 46 is a top isometric cutaway view along the arrows shown in FIG. 45. FIG. 46 shows space/gap ff3 as being closed between lid 26 and canister 25 which results in lid seal 26o and canister seal 25d fully sealed by rotational orientation between lid 26 and canister 25. FIG. 46 shows separated lid pillars 26 and canister pillars 25 may be move respectively along radians/arcs. FIG. 46 also shows juxtaposed lid pillars 26 and canister pillars 25 may be moved respectively along radians/arcs. FIG. 46 also shows canister pillar bottoms 25b1h, 25b2h, 25b3h and 25b4h are positioned on lid ramps 26g1, 26g2, 26g3 and 26g4.

Turning to FIG. 47. FIG. 47 is a bottom plan view of alternative embodiment plug 66 as show in FIG. 49 and FIG. 51. As shown in FIG. 47, 66i shows a reduced pressure aperture. 66b represents the thread as shown as 66b in FIG. 49. 66e shows the internal structural struts of plug 66 as can be seen in 6 places.

Turning to FIG. 48. FIG. 48 is a bottom plan view of alternative plug 67 as shown in FIGS. 50 and 52. 67i shows a reduced pressure aperture. 67e shows one of six internal structural struts. Plug 67 is similar to that of plug 66 of FIG. 47 except that plug 67 has a reduced diameter reduced pressure aperture 67i.

Turning to FIG. 49. FIG. 49 is a side elevation view of alternative embodiment plug 66. 66a shows a patient suction tubing port connection. 66c shows the top sealing surface of plug 66. 66b shows a single thread circumscribing the top outer diameter of plug 66 by just less than 360 degrees. This facilitates the cost effective manufacturing of a plug embodying a single plug retaining cap and plug removal thread being produced with a single pull injection molding tool. 66h shows the break in the single cap retaining thread. 66f is a first diameter of plug 66. 66g is a second diameter of plug 66. 66h is a third diameter of plug 66.

Turning to FIG. 50. FIG. 50 is a side elevation view of alternative plug embodiment 67. 67a shows a patient tubing connection port. 67c shows the top sealing surface of plug 67. 67b shows a single retaining thread that circles the outside diameter of plug 67. 67h shows a break in the retaining thread 67b. This break is for the same purposes recited regarding FIG. 49. 67f is a first plug diameter. 67g is a second diameter of plug 67g. 67i is a third diameter of plug 67g.

Turning to FIG. 51. FIG. 51 is a top plan view of plug 66 as shown in FIGS. 47 and 49. 66a represents a reduced pressure aperture and looking down from the top plan view depicts the patient suction tubing connection port. 66c shows the top sealing surface of plug 66. 66b shows the single retaining thread. 66d shows the struts between the outside rim of plug 66 and the internal structure of plug 66. 66h shows the break in the single retaining thread of 66b. 66j shows one of six reduced pressure apertures broken into six annularly separated apertures. 66i shows the lid top sealing surface of plug 66.

Turning to FIG. 52. FIG. 52 is a top plan view of plug 67 in FIG. 50. FIG. 52 shows essentially the same features as FIG. 51 however reduced pressure aperture 67a is smaller than the reduced pressure aperture of 66a of FIG. 51.

Turning to FIG. 53. FIG. 53 is a side elevation cutaway of an alternative bottle embodiment 19x, plug 71 and bottle cap 23x. The top view of FIG. 53 is a side elevation cutaway showing the relationship between plug 71 and bottle cap 23x whereby the single retaining thread of plug 71 has been completely threaded into cap 23x. 28x1 shows where cap 23 seals against the top sealing surface of plug 71.

Turning to FIG. 54. FIG. 54 is a side elevation cutaway of an alternative bottle 19y and cap 23y. The upper view of FIG. 54 is a side elevation cutaway view of alternative plug embodiment 71, bottle cap 23y and showing the relationship of the single retaining thread being retained by the first outwardly positioned inside thread of cap 23y shown at 28x1. 29x1 shows that only a single thread of capture is necessary to retain the plug 71 with the cap 23y thereby using cap 23y as a tool to remove plug 71 from bottle 19y when desired. It is noted that cap 23 may be threaded all the way down to seal cap 23y to the top sealing surface of plug 71 as shown at 28x1 in FIG. 53, and as shown at 28x1 of FIG. 54. This provides a leak resistant seal for disposal of any potential fluid collected in bottle 19, 20, 22, 19x, 19y & 19z as was depicted also in FIGS. 13, 14, 15, 53, 54, & 55.

Turning to FIG. 55. FIG. 55 is a side elevation view of an alternative embodiment bottle 19z having plug 71 disposed in the pour spout as seen in FIG. 55 with cap 23z threaded onto bottle 19z sealing bottle plug 71 and cap 23z with a leak resistant seal. The upper view of FIG. 55 cap 23z can be seen with internal threads 69 terminating in thread 23xa, ya, za, representing the outermost inside threads of caps 23x, 23y and 23z. Each of these caps internal threads have the potential to capture and retain plug thread 71b in FIGS. 54, 54, and 55 as depicted at 28x1 of FIG. 54.

Figure 56:
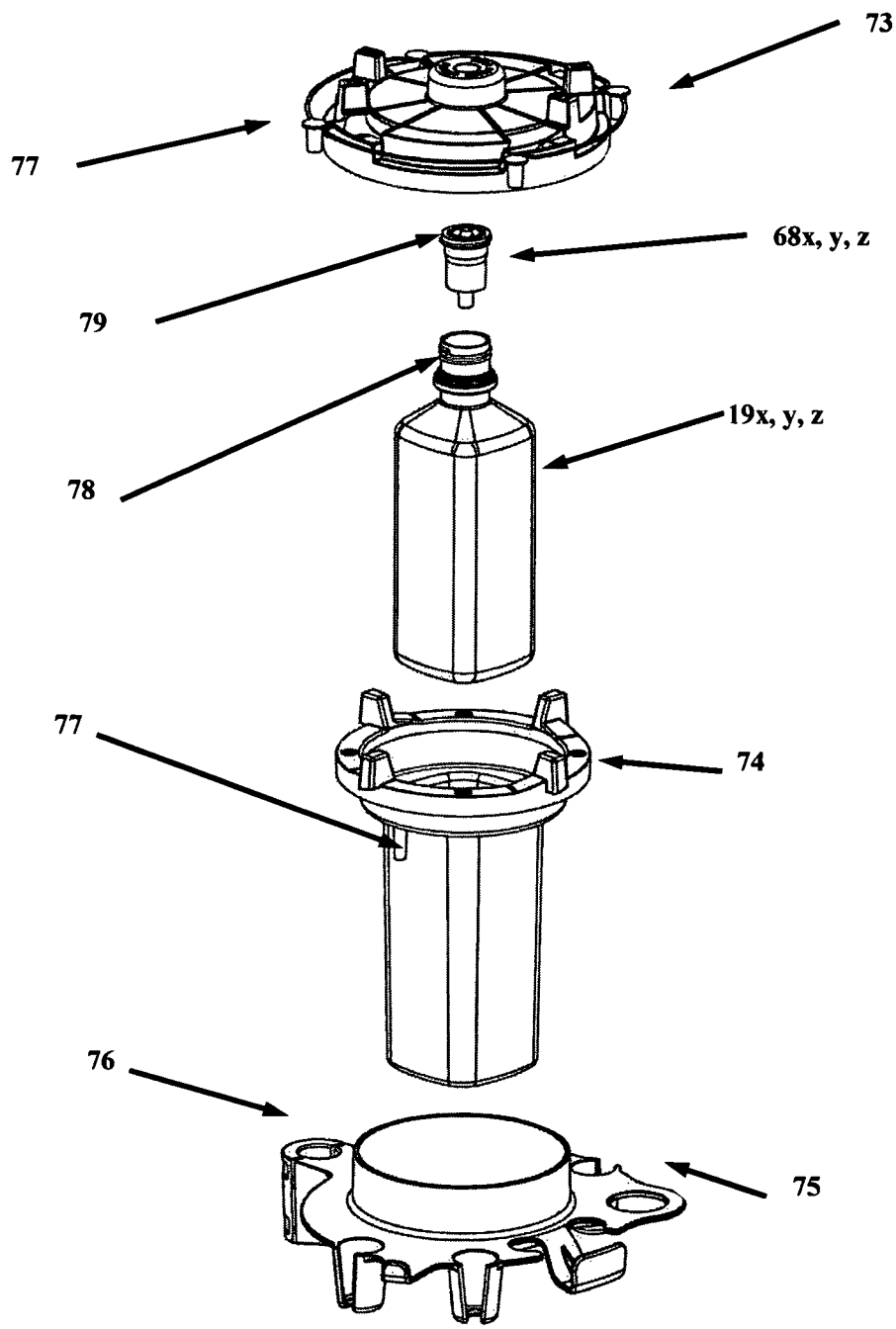
FIG. 56 is a top isometric exploded view of an alternative embodiment lid 73, plug 79, bottle 19x, y, z, alternative embodiment canister 74 and canister holder 75.

Turning to FIG. 56. FIG. 56 is a top isometric exploded view of alternative lid embodiment 73, plug 65, alternative bottle embodiments 19x, y, and z. Alternative simplified embodiment canister body 74 and canister holder 75. Also shown is plug thread 79, bottle thread 78 reduced pressure vacuum hose connection portal 77 disposed and facing in a downward orientation on canister 74. Also shown is canister pole mount 76 associated with holder 75. Also shown at 77a is lid 73 having port caps retained by retainer which have been injection molded unitary with lid 73 in the same tool during the same shot as lid 73.

Figure 57:
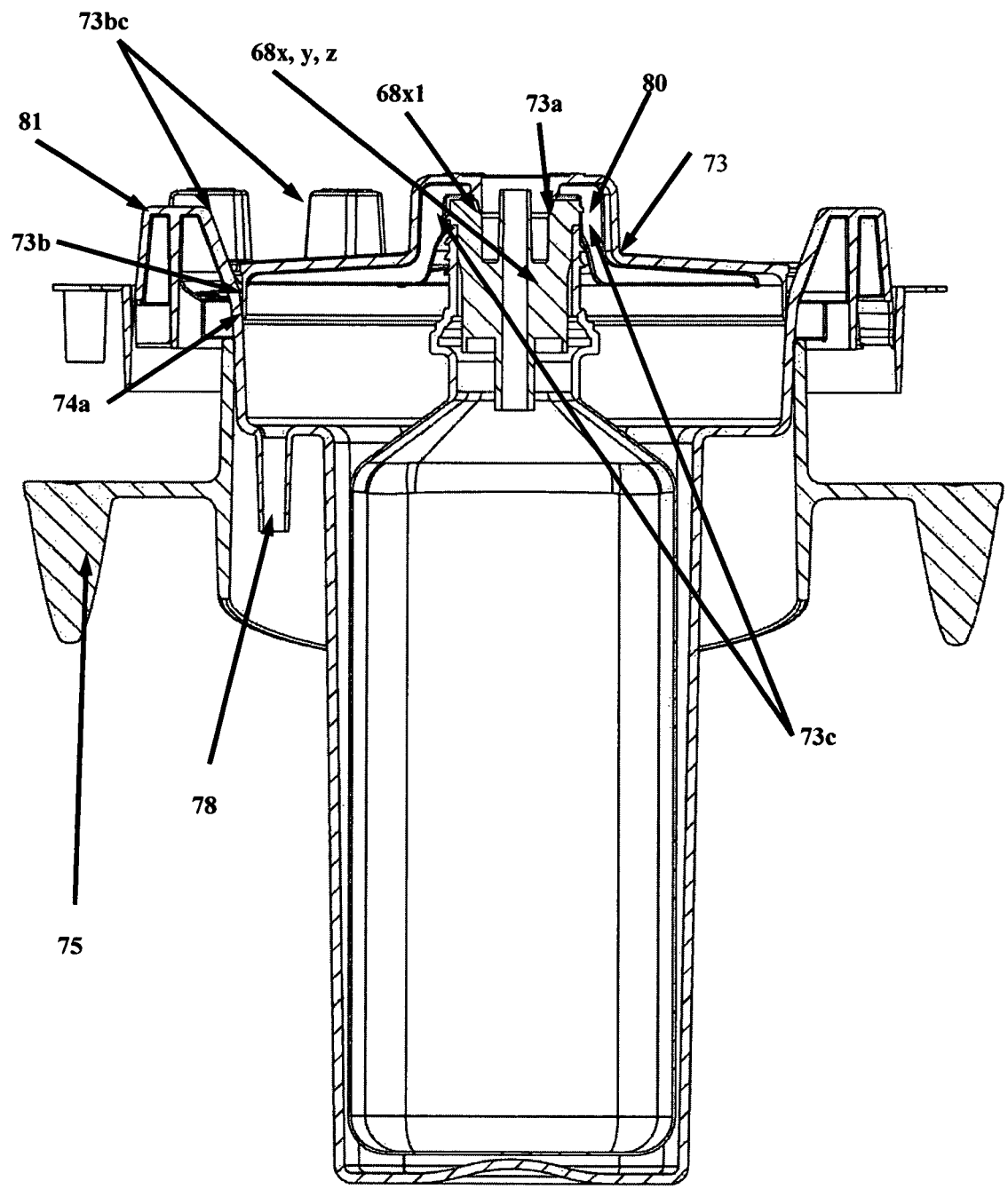
FIG. 57 is a side elevation cutaway assembly view of the elements of FIG. 56.

Turning to FIG. 57. FIG. 57 is a side elevation cutaway of an alternative embodiment assembly of the parts shown in the exploded view of FIG. 56. Canister 75 can be seen in sealed orientation with lid 73 and annular canister seal 74a can be seen sealed with annular lid seal 73b. Plug 65 (as referred to in FIGS. 23, 29, 30, 35, 36, 37, 38, 44, 56) is similar to plug 68x, y, x of FIG. 56 which is similar to plugs 66 and 67 of FIGS. 47-52. Sealing surface 68x1 in FIG. 57 comprises the lid (73a) sealing surface of plug 68x, y, x, (shown in FIG. 56) and is similar to: 1) sealing surface 66l of FIG. 51 comprising the Lid (73a) sealing surface of plug 66: 2) sealing surface 67l of FIG. 52 comprising the lid (73a) sealing surface of plug 67: 3) which are also similar to lid sealing surface 65a (not shown and referred to in the detailed descriptions of FIGS. 37, 38 & 57). Plug 65 and plug sealing surface feature 65a (the lid 73a sealing surface of plug 65) are referred to many times in the instant case with plug 65a sealing surface referenced as not shown in the detailed descriptions of FIGS. 37 and 38. This means that the features and functions of plug 65a sealing surface are not shown in those particular drawings and views. The spatial, structural, performance and functional relationships of how plug 65 engages lid 26 and bottle 19 in FIGS. 36, 37, 38, are shown by the features of the plug bottle and lid relationships of this FIG. 57. Plug features 65a lid 73 also embodies plug/bottle alignment registration guides as in 8 places as seen in FIG. 24, however this view of the registration guides 73c of FIG. 57 more clearly depicts the funnel shape and action of guiding the bottle and plug into sealing engagement with plug seal 68x1 of plug 65. Canister pillars 81, which are similar to the canister pillars 25b1, 2, 3, & 4 of canister 25 as shown in FIGS. 17, 20, 25, 26, 29, 30 are shown at 81. Lid pillars 73bc are similar to the lid pillars of lid 26 as shown in FIGS. 17, 20, 21, 22, 27, 26, 28, 29, 30, 31, 32, 33, & 34.

Figure 58:
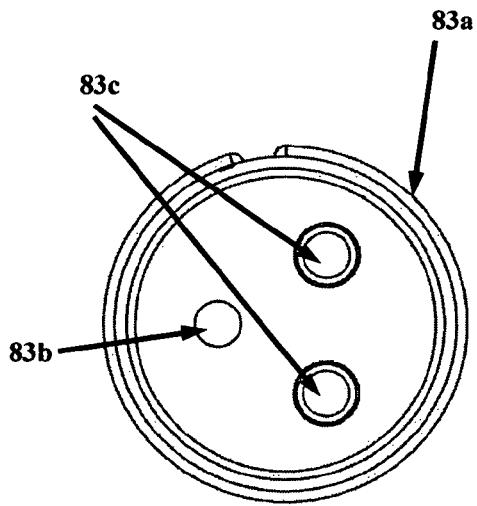
FIG. 58 is a bottom plan view of plug 83 as shown in FIG. 60.

Turning to FIG. 58. FIG. 58 shows an alternative plug embodiment 83a having three reduced pressure apertures. The plug embodiment 83 is useful where a scenario requires one hose connector 83b for egressing reduced pressure and two reduced pressure apertures 83c for ingressing reduced pressure forces. FIG. 58 is a bottom plan view of plug 83 as seen in FIG. 60.

Figure 59:
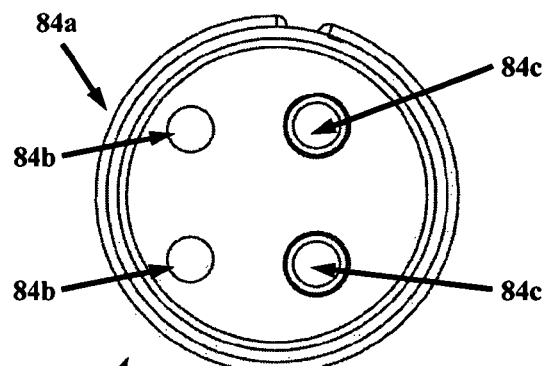
FIG. 59 is a bottom plan view of plug 84 as shown in FIG. 61.
Figure 61:
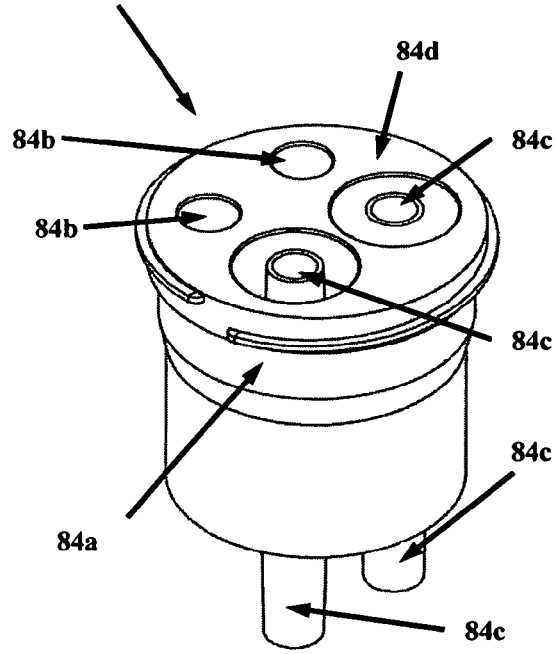
FIG. 61 is a top isometric view of plug 84 which shows four reduced pressure egress and/or ingress apertures.

Turning to FIG. 59. FIG. 59 is a bottom plan view of the plug 84 as shown in FIG. 61. FIG. 59 shows the bottom plan view of plug 84 having four reduced pressure apertures. Two reduced pressure apertures 84b may be used to connect to two separate conduits for egressing reduced pressure in two places and two reduced pressure apertures 84c may be connected to two conduits and used for ingressing reduced pressure in two places.

Figure 60:
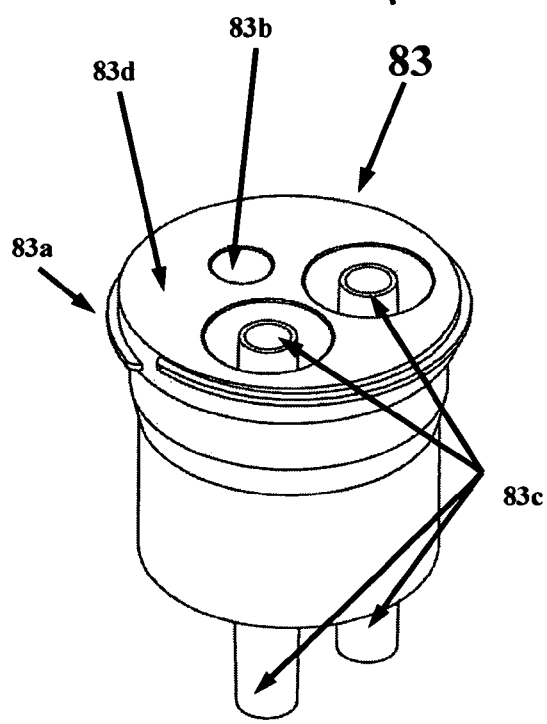
FIG. 60 is a top isometric view of plug 83 which shows three reduced pressure egress and/or ingress apertures.

Turning to FIG. 60. FIG. 60 is a top isometric view of plug 83 as seen in FIG. 58 which has three reduced pressure apertures as shown in FIG. 58 at 83b and 83c as well as a cap retaining thread 83a.

Turning to FIG. 61. FIG. 61 is a top isometric view of the plug as seen in FIG. 59. Plug 84 is seen with four reduced pressure apertures. Plug 84 can be seen having cap retaining thread 84a and two reduced pressure apertures 84b and two reduced pressure apertures 84 and a plug top sealing surface 84d. The plug 84 of FIGS. 59 and 61 provide the user with options to connect two in and out pathways, or three in and one out passageways, or three out and one in passageways. The instant case is not meant to limit the number of reduced pressure apertures associated with any particular plug embodiment plug. It is understood that the number of bottle plug apertures would best be determined by the end user based on the different 5 requirements of the reduced pressure collection marketplace.

What is claimed is:

1. A supply chain method comprising,
    a) egressing a material from a container,
    b) retaining said container inside a housing, said container configured having a plug inserted into a material egress opening of said container within a portion of a vacuum draw path, said vacuum draw path configured to connect a first space inside and a second space outside said container during said retention,
    c) applying vacuum forces to said path configured to provide vacuum flow through said second space at least in part by a seal between said plug and said housing,
    d) egressing said vacuum flow out of said container and into said second space through at least one plug port located outside said seal.

2. A supply chain method comprising,
    a) egressing a material from a container,
    b) retaining said container inside a housing, said container configured having a plug inserted into at least one opening in said container during said retention while inside a portion of a vacuum draw path,
    c) applying vacuum forces to said path, said path configured at least in part by a first seal between said plug and a lid, and a second seal between said lid and said housing,
    d) drawing waste material into said container, drawing waste material from said container into a space between said container and said housing through at least one plug port located outside said first seal.

3. A method of claim 1 wherein said material includes a medicament.

4. A method of claim 1 wherein said material includes a pharmaceutical preparation.

5. A method of claim 1 wherein said material includes a formulary.

6. A method of claim 1 wherein said material includes agents provided during the practice of anesthesia.

7. A method of claim 1 wherein said material is combined with a drug.

8. A method of claim 1 wherein said container is blow fill seal manufactured.

9. A method of claim 1 wherein said container is blow mold manufactured.

10. A method of claim 1 wherein said container provides a material.

11. A method of claim 1 wherein said material is provided with a drug.

12. A method of claim 2 wherein said material includes a medicament.

13. A method of claim 2 wherein said material includes a pharmaceutical preparation.

14. A method of claim 2 wherein said material includes a formulary.

15. A method of claim 2 wherein said material includes agents provided during the practice of anesthesia.

16. A method of claim 2 wherein said material is combined with a drug.

17. A method of claim 2 wherein said container is blow fill seal manufactured.

18. A method of claim 2 wherein said container is blow mold manufactured.

19. A method of claim 2 wherein said container provides a material.

20. A method of claim 2 wherein said material is provided with a drug.

* * * * *

UNITED STATES PATENT AND TRADEMARK OFFICE
CERTIFICATE OF CORRECTION

PATENT NO.         : 8,920,396 B2
APPLICATION NO.    : 13/958606
DATED              : December 30, 2014
INVENTOR(S)        : Jack W Romano and Adam L. Smith It is certified that error appears in the above-identified patent and that said Letters Patent is hereby corrected as shown below:

In the Specification

1) Column 2, line 54: delete "require" and insert --requiring-- to read "management requiring"...
2) Column 2, line 67: delete "time" and insert --times-- to read "many times the"...
3) Column 3, line 54: delete "are" to read "volumes sometimes"...
4) Column 3, line 56: delete "by" to read "whereby seems"...
5) Column 4, lines 13-14: delete "plus" to read "maintenance requires"...
6) Column 4, line 17: delete "An other" and insert --Another-- to read "operations. Another disadvantage"...
7) Column 4, line 18: delete "which" to read "canister requires"...
8) Column 4, line 32: delete "use with out" and insert --used without-- to read "cannot be used without the"...
9) Column 4, line 52: insert --a-- between -such- and -stackable- to read "such a stackable"...
10) Column 4, line 65: delete "of" and insert --or-- to read "easily or effortlessly"...
11) Column 5, line 11: delete "contents" and insert --contends-- to read "applicant contends that"...
12) Column 5, line 40: delete "by" and insert --of-- to read "manufacturing of"...
13) Column 5, lines 55-56: insert --to-- at the beginning of line 56 to read "up to potentially"...
14) Column 5, line 66: insert --of-- between -collection- and -waste- to read "collection of waste"...
15) Column 6, line 11: delete "the" at the beginning of line 11 to read "waste collection"...
16) Column 6, line 22: delete "the" and insert --then-- to read "and then collecting"...
17) Column 6, line 23-24: delete "the applicable to" to read "applicable to the instant case"...
18) Column 6, line 54: delete the second "the" to read "the unnecessary need for separate"...
19) Column 6, line 63: delete "container" and insert --containers-- to read "Such containers are"...
20) Column 7, lines 1-2: delete "containers" at the beginning of line 2 to read "containers, made of laminated"...
21) Column 7, line 5: add a "," between -solution- and -intravenous- to read "solutions, intravenous"...
22) Column 7, lines 29-30: delete "container" and insert --containers-- to read "Other containers such"...
23) Column 8, line 6: delete "fort" and insert --for-- to read "containers for the"...

Signed and Sealed this
Twelfth Day of May, 2015

Michelle K. Lee
*Director of the United States Patent and Trademark Office*

CERTIFICATE OF CORRECTION (continued)
U.S. Pat. No. 8,920,396 B2

24) Column 8, line 49: delete "know" and insert --known-- to read "processes known by"...
25) Column 9, line 59: delete "is" and insert --of-- to read "system of creating"...
26) Column 10, line 61: delete "positing" and insert --positioning-- to read "positioning a transfer"...
27) Column 11, line 45: insert --of-- between -dispose- and -material- to read "dispose of material"...
28) Column 11, line 59: insert --a-- between -fabricating- and -liquid- to read "fabricating a liquid"...
29) Column 12, line 4: delete "in" to read "wand relation"...
30) Column 15, line 3: delete "show's" to read "FIG. 8 shows a new"...
31) Column 15, line 18: delete "a" and insert --an-- to read "for an online"...
32) Column 15, line 43: delete "give" and insert --gives-- to read "gives rise to"...
33) Column 17, line 47: delete "650" and insert --65-- to read "plug 65, bottle"...
34) Column 18, line 28: add ')' at the end of the line to read "system.)"...
35) Column 18, line 32: delete "view of cutaway" and insert --cutaway view-- to read "isometric cutaway view of"...
36) Column 20, line 1: delete "of" and insert --or-- to read "department or facility"...
37) Column 20, line 38: delete "an" and insert --and-- to read "prior art and enterprise resource"...
38) Column 23, line 52: delete "35 c" and insert --35 C-- to read ", 35 C at"...
39) Column 23, line 53: delete the second "and" to read "and 36 D at 270"...
40) Column 24, line 62: delete "show" and insert --shown-- to read "is shown at"...
41) Column 25, line 12: delete "b34" and insert --b4-- to read "b3 and b4 in"...
42) Column 26, lines 44-45: delete "plan" and insert --plane-- to read "coordinate plane defining"...
43) Column 28, line 1: insert --as-- between -28- and -depicted- to read "at 28 as depicted"...
44) Column 28, line 2: delete "are" and insert --as-- to read "pillars as shown"...
45) Column 28, line 60: insert --to-- between -designed- and -off- to read "designed to off set"...
46) Column 30, line 57: delete "oflid" and insert --of lid-- to read "orientations of lid 26"...
47) Column 30, lines 60-61: delete "have has" at lines 60-61 and insert --having-- to read "26r2 having been urged"...
48) Column 31, line 1: delete "urges" and insert --urged-- to read "urged along"...
49) Column 31, line 33: delete "are" and insert --as-- to read "26h2 as seen"...
50) Column 31, line 40: delete "urges" and insert --urged-- to read "rotationally urged closer"...
51) Column 34, line 11: delete "plug" between -embodiment- and -It- to read "embodiment. It is"...
52) Column 34, line 13: delete "5" between -different- and -requirements- to read "different requirements"...